(12) United States Patent
Mandal

(10) Patent No.: US 11,905,559 B2
(45) Date of Patent: Feb. 20, 2024

(54) MATERIALS AND METHODS FOR CONTROLLING GENE EXPRESSION

(71) Applicant: Maumita Mandal, Pittsburgh, PA (US)

(72) Inventor: Maumita Mandal, Pittsburgh, PA (US)

(73) Assignee: Maumita Mandal, Pittsburgh, PA (US)

(*) Notice: Subject to any disclaimer, the term of this patent is extended or adjusted under 35 U.S.C. 154(b) by 668 days.

(21) Appl. No.: 16/325,857

(22) PCT Filed: Aug. 2, 2017

(86) PCT No.: PCT/US2017/045100
§ 371 (c)(1),
(2) Date: Feb. 15, 2019

(87) PCT Pub. No.: WO2018/034843
PCT Pub. Date: Feb. 22, 2018

(65) Prior Publication Data
US 2019/0177793 A1     Jun. 13, 2019

Related U.S. Application Data

(60) Provisional application No. 62/432,160, filed on Dec. 9, 2016, provisional application No. 62/432,077, filed on Dec. 9, 2016, provisional application No. 62/376,328, filed on Aug. 17, 2016, provisional application No. 62/376,325, filed on Aug. 17, 2016.

(51) Int. Cl.
*C12N 15/115* (2010.01)
*C12Q 1/6876* (2018.01)
*C12Q 1/68* (2018.01)
*G01N 33/53* (2006.01)

(52) U.S. Cl.
CPC .......... *C12Q 1/6876* (2013.01); *C12N 15/115* (2013.01); *C12Q 1/68* (2013.01); *G01N 33/5308* (2013.01); *C12N 2310/16* (2013.01)

(58) Field of Classification Search
CPC .......................... C12N 15/115; C12N 2310/16
See application file for complete search history.

(56) References Cited

U.S. PATENT DOCUMENTS

2008/0269258 A1*  10/2008  Breaker ............... C07H 21/04
                                                  435/375
2011/0124713 A1*   5/2011  Batey .................. C12N 15/111
                                                  536/23.1

FOREIGN PATENT DOCUMENTS

WO    WO2006042143 A2    4/2006
WO    WO2007100412 A2    9/2007
WO    WO2015071385 A2    5/2015

OTHER PUBLICATIONS

Chandra et al. Nature Chemical Biology 13, 194-201 (Year: 2017).*
Edwards et al. J. Mol. Biol. 23:385:938-948 (Year: 2009).*
Edwards et al. Nature Education 3(9):9, pp. 1-6 (Year: 2010).*
Kaiser et al. Nucleic Acids Research vol. 49, 3661-3671 (Year: 2021).*
Jain et al. Biochemistry 49, 3703-3714 (Year: 2010).*
International Search Report and Written Opinion for Application No. PCT/US2017/045100, dated Nov. 9, 2017 (21 pages).
Lynch et al: "A High-Throughput Screen for Synthetic Riboswitches Reveals Mechanistic Insights into Their Function", Chemistry and Biol, Current Biology, London, GB, vol. 14, No. 2, Feb. 23, 2007 (Feb. 23, 2007), pp. 73-184, XP005896375, ISSN: 1074-5521, DOI: 10.1016/J.CHEMBIOL.2006.12.008.
Ogawa et al: "Aptazyme-based ri boswi tches as label-free and detector-free sensors for cofactors", Bioorganic & Medicinal Chemistry Letters, Pergamon, Amsterdam, NL, vol. 17, No. 11, May 10, 2007 (May 10, 2007), pp. 3156-3160, XP022068412, ISSN: 0960-894X, DOI: 10.1016/J.BMCL.2007.03.033.
Jayasena, Sumedha D.: "Aptamers: an emerging class of molecules that rival antibodies in diagnostics", Clinical Chemistry, American Association for Clinical Chemistry, Washington, DC, vol. 45, Jan. 1, 1999 (Jan. 1, 1999), pp. 1628-1650, XP008156390, ISSN: 0009-9147.
Topp, Shana et al.: "Emerging Applications of Riboswitches in Chemical Biology", ACS Chemical Biology, vol. 5, No. 1, Jan. 15, 2010 (Jan. 15, 2010), pp. 139-148, XP055108283, ISSN: 1554-8929, DOI: 10.1021/cb900278x.

* cited by examiner

*Primary Examiner* — Brian Whiteman
(74) *Attorney, Agent, or Firm* — K&L Gates LLP

(57) ABSTRACT

A high-resolution dual-beam counter propagating optical-tweezers instrument was designed that can measure forces at <1 pN and one nanometer distance at a temporal resolution of 25 µs with high accuracy and precision. Using the high-resolution optical-tweezers, time-dependent conformational switching and structural rearrangements in a single-molecule of the guanine aptamer were identified that follow a modified induced-fit model, where guanine remodels multiple barriers and triggers the receptor conformation rapidly to synchronize with the elongating transcriptional machinery for controlling gene regulation.

2 Claims, 68 Drawing Sheets

Specification includes a Sequence Listing.

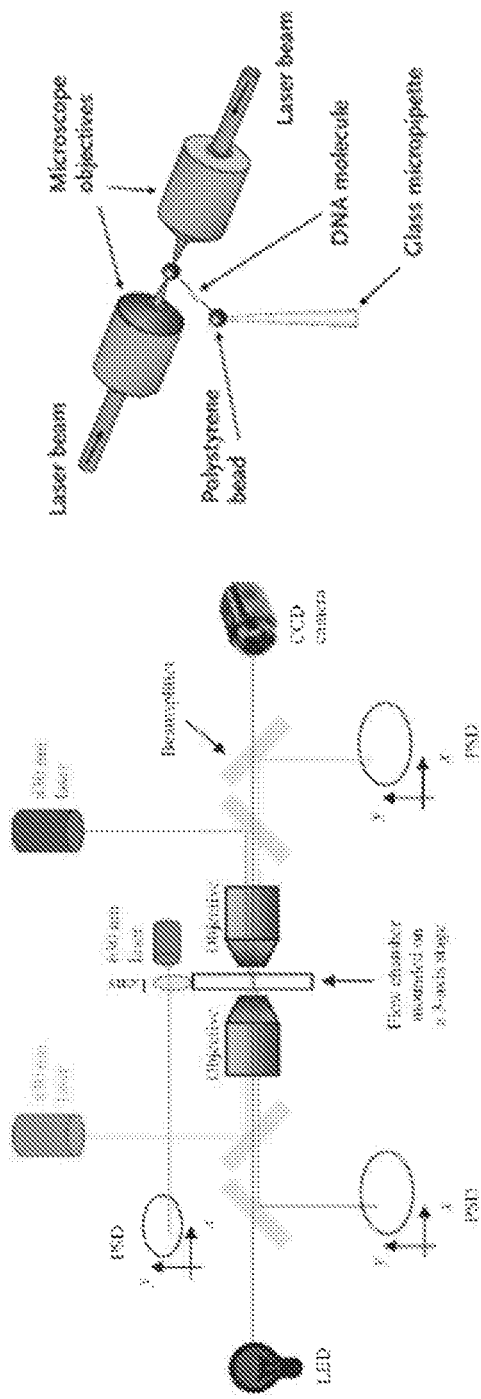

G-aptamer RNA wt

*m4 RNA* altered P3 stem with $G^{59}$-$C^{67}$ base pair

*m5 RNA*

Long P1 helix is introduced

FIGURE 8C

| RNA | $K_D$ (nM) | ΔH (kcal/mol) | ΔS (cal/mol/deg) | ΔG (kcal/mol) |
|---|---|---|---|---|
| wt | 4.2 ± 0.6 | -63.7 ± 1.1 | -171.7 ± 3.2 | -11.63 ± 0.20 |
| m1 | 149 ± 53 | -74.4 ± 3.2 | -214 ± 11 | -9.52 ± 0.22 |
| m2 | 36 ± 0.2 | -74.6 ± 4.5 | -212 ± 16 | -10.37 ± 0.16 |
| m3 | 73.6 ± 2.9 | -81.6 ± 1.7 | -237 ± 5.7 | -9.85 ± 0.08 |
| m4 | 3.59 ± 0.05 | -69.0 ± 1.8 | -189 ± 5.7 | -11.67 ± 0.10 |
| m6 | 6.7 ± 0.6 | -65.7 ± 0.8 | -181 ± 3.2 | -11.32 ± 0.05 |
| m7 | 16.9 ± 1 | -66.8 ± 6.1 | -185 ± 20 | -10.73 ± 0.06 |

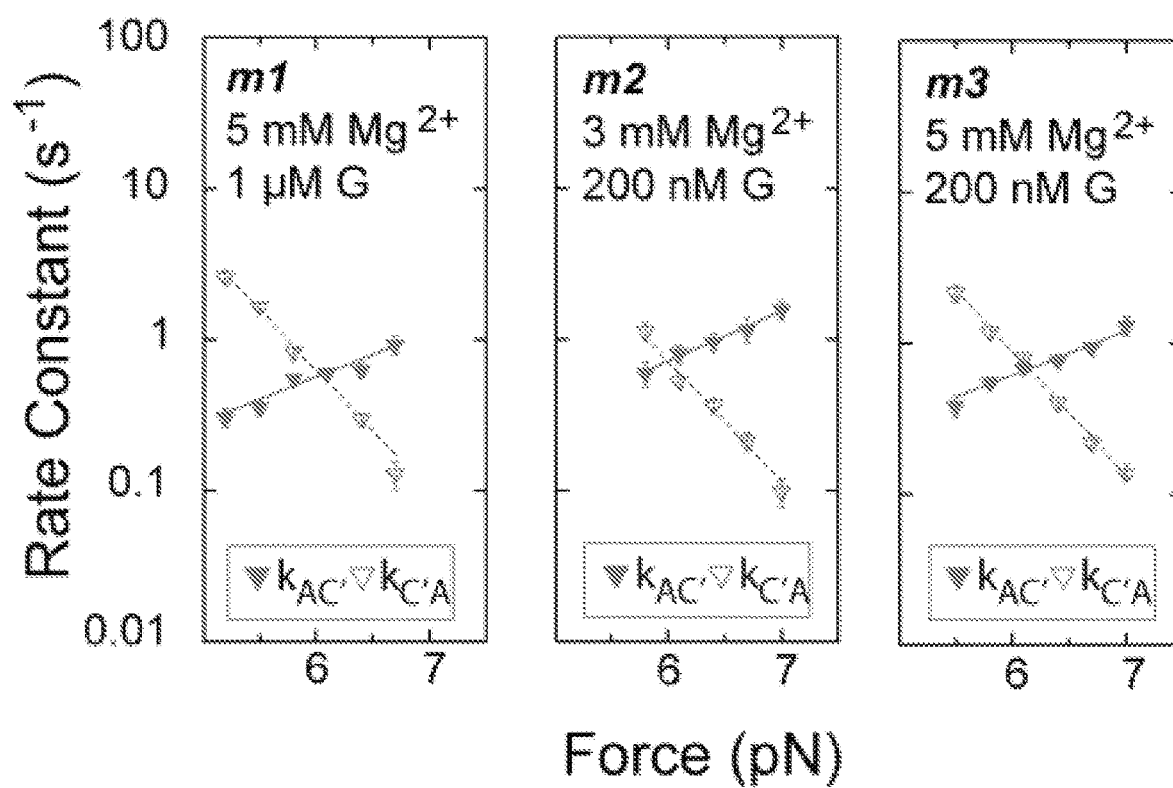

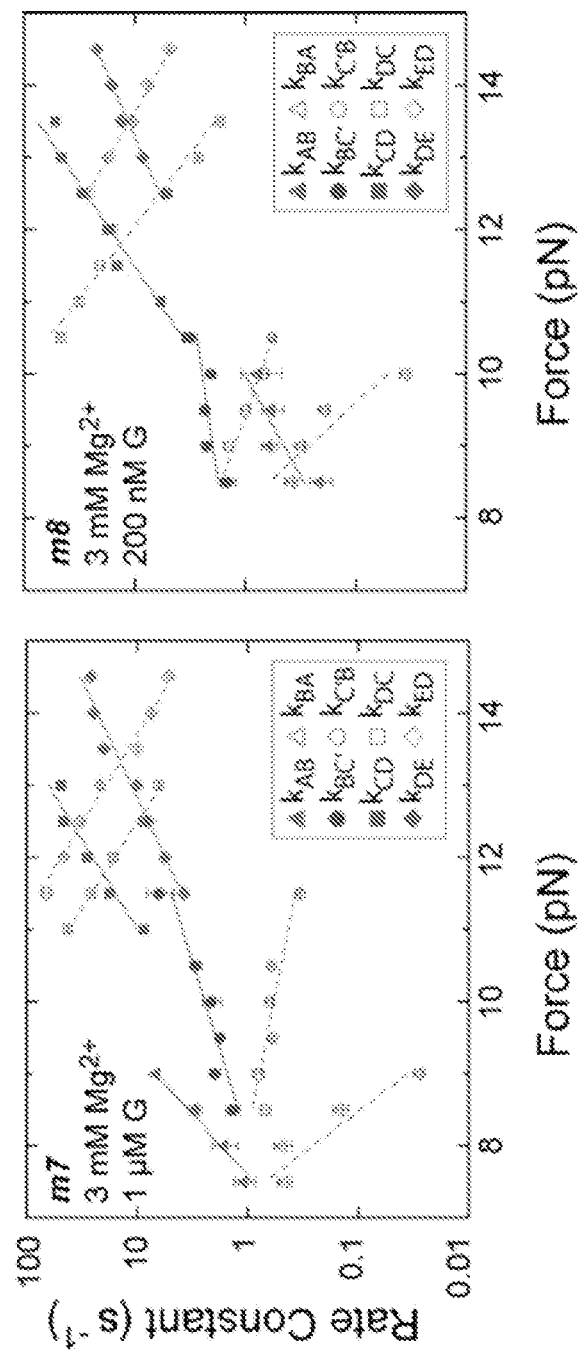

I, II and IV - Terminator Conformation
III - Non- terminator Conformation

SEQUENCE LISTING

```
<160> NUMBER OF SEQ ID NOS: 30

<210> SEQ ID NO 1
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<220> FEATURE:
<221> NAME/KEY: J1/2
<222> LOCATION: (9)..(13)
<220> FEATURE:
<221> NAME/KEY: P2_hairpin
<222> LOCATION: (14)..(18)
<220> FEATURE:
<221> NAME/KEY: L2
<222> LOCATION: (19)..(25)
```

```
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(46)
<220> FEATURE:
<221> NAME/KEY: L3
<222> LOCATION: (47)..(53)
<220> FEATURE:
<221> NAME/KEY: P3_hairpin
<222> LOCATION: (54)..(59)
<220> FEATURE:
<221> NAME/KEY: J3/1
<222> LOCATION: (60)..(61)
<220> FEATURE:
<221> NAME/KEY: P1_hairpin
<222> LOCATION: (62)..(69)

<400> SEQUENCE: 1
cacucauaua aucgcgugga uauggcacgc aaguuucuac cgggcaccgu aaauguccga      60
cuaugggug                                                             69

<210> SEQ ID NO 2
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<220> FEATURE:
<221> NAME/KEY: J1/2
<222> LOCATION: (9)..(13)
<220> FEATURE:
<221> NAME/KEY: P2_hairpin
<222> LOCATION: (14)..(18)
<220> FEATURE:
<221> NAME/KEY: L2
<222> LOCATION: (19)..(25)
<223> OTHER INFORMATION: nucleobase G37 has been replaced with an
      adenine residue (A)
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(46)
<220> FEATURE:
<221> NAME/KEY: L3
<222> LOCATION: (47)..(53)
<220> FEATURE:
<221> NAME/KEY: P3_hairpin
<222> LOCATION: (54)..(59)
<220> FEATURE:
<221> NAME/KEY: J3/1
<222> LOCATION: (60)..(61)
<220> FEATURE:
<221> NAME/KEY: P1_hairpin
<222> LOCATION: (62)..(69)

<400> SEQUENCE: 2
cacucauaua aucgcgugga uauagcacgc aaguuucuac cgggcaccgu aaauguccga      60
cuaugggug                                                             69

<210> SEQ ID NO 3
```

```
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<220> FEATURE:
<221> NAME/KEY: J1/2
<222> LOCATION: (9)..(13)
<220> FEATURE:
<221> NAME/KEY: P2_hairpin
<222> LOCATION: (14)..(18)
<220> FEATURE:
<221> NAME/KEY: L2
<222> LOCATION: (19)..(25)
<223> OTHER INFORMATION: nucleobase G37 is replaced with an adenine
      residue (A)
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(46)
<220> FEATURE:
<221> NAME/KEY: L3
<222> LOCATION: (47)..(53)
<223> OTHER INFORMATION: nucleobase C61 is replaced with a uracil
      residue (U)
<220> FEATURE:
<221> NAME/KEY: P3_hairpin
<222> LOCATION: (54)..(59)
<220> FEATURE:
<221> NAME/KEY: J3/1
<222> LOCATION: (60)..(61)
<220> FEATURE:
<221> NAME/KEY: P1_hairpin
<222> LOCATION: (62)..(69)

<400> SEQUENCE: 3
cacucauaua aucgcgugga uauagcacgc aaguuucuac cgggcacugu aaauguccga    60
cuauggug                                                             69

<210> SEQ ID NO 4
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<220> FEATURE:
<221> NAME/KEY: J1/2
<222> LOCATION: (9)..(13)
<220> FEATURE:
<221> NAME/KEY: P2_hairpin
<222> LOCATION: (14)..(18)
<220> FEATURE:
<221> NAME/KEY: L2
<222> LOCATION: (19)..(25)
<223> OTHER INFORMATION: nucleobase G38 is replaced with an adenine
      residue (A)
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(46)
```

```
<220> FEATURE:
<221> NAME/KEY: L3
<222> LOCATION: (47)..(53)
<220> FEATURE:
<221> NAME/KEY: P3_hairpin
<222> LOCATION: (54)..(59)
<220> FEATURE:
<221> NAME/KEY: J3/1
<222> LOCATION: (60)..(61)
<220> FEATURE:
<221> NAME/KEY: P1_hairpin
<222> LOCATION: (62)..(69)

<400> SEQUENCE: 4
cacucauaua aucgcgugga uaugacacgc aaguuucuac cgggcaccgu aaauguccga    60
cuaugggug                                                           69

<210> SEQ ID NO 5
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<220> FEATURE:
<221> NAME/KEY: J1/2
<222> LOCATION: (9)..(13)
<220> FEATURE:
<221> NAME/KEY: P2_hairpin
<222> LOCATION: (14)..(18)
<220> FEATURE:
<221> NAME/KEY: L2
<222> LOCATION: (19)..(25)
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(46)
<223> OTHER INFORMATION: nucleobase A59 is replaced with a guanine
      residue (G)
<220> FEATURE:
<221> NAME/KEY: L3
<222> LOCATION: (47)..(53)
<220> FEATURE:
<221> NAME/KEY: P3_hairpin
<222> LOCATION: (54)..(59)
<223> OTHER INFORMATION: nucleobase U67 is replaced with a cytosine
      residue (C)
<220> FEATURE:
<221> NAME/KEY: J3/1
<222> LOCATION: (60)..(61)
<220> FEATURE:
<221> NAME/KEY: P1_hairpin
<222> LOCATION: (62)..(69)

<400> SEQUENCE: 5
cacucauaua aucgcgugga uauggcacgc aaguuucuac cgggcgccgu aaacguccga    60
cuaugggug                                                           69

<210> SEQ ID NO 6
<211> LENGTH: 73
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
```

```
<222> LOCATION: (1)..(10)
<223> OTHER INFORMATION: P1 hairpin is longer with the addition of new
      nucleotides
<220> FEATURE:
<221> NAME/KEY: J1/2
<222> LOCATION: (11)..(15)
<220> FEATURE:
<221> NAME/KEY: P2_hairpin
<222> LOCATION: (16)..(20)
<220> FEATURE:
<221> NAME/KEY: L2
<222> LOCATION: (21)..(27)
<220> FEATURE:
<221> NAME/KEY: P2_hairpin
<222> LOCATION: (28)..(32)
<220> FEATURE:
<221> NAME/KEY: J2/3
<222> LOCATION: (33)..(42)
<220> FEATURE:
<221> NAME/KEY: P3_hairpin
<222> LOCATION: (43)..(48)
<220> FEATURE:
<221> NAME/KEY: L3
<222> LOCATION: (49)..(55)
<220> FEATURE:
<221> NAME/KEY: P3_hairpin
<222> LOCATION: (56)..(61)
<220> FEATURE:
<221> NAME/KEY: J3/1
<222> LOCATION: (62)..(63)
<220> FEATURE:
<221> NAME/KEY: P1_hairpin
<222> LOCATION: (64)..(73)
<223> OTHER INFORMATION: P1 hairpin is longer with the addition of new
      nucleotides

<400> SEQUENCE: 6
agcgcucaua uaaucgcgug gauauggcac gcaaguuucu accgggcacc guaaaugucc        60
gacuaugggc gcu                                                          73

<210> SEQ ID NO 7
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<220> FEATURE:
<221> NAME/KEY: J1/2
<222> LOCATION: (9)..(13)
<220> FEATURE:
<221> NAME/KEY: P2_hairpin
<222> LOCATION: (14)..(18)
<220> FEATURE:
<221> NAME/KEY: L2
<222> LOCATION: (19)..(25)
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(45)
<220> FEATURE:
<221> NAME/KEY: L3
<222> LOCATION: (46)..(54)
<223> OTHER INFORMATION: nucleobase U67 is replaced with an adenine
      residue (A), which results in a shortened P3 hairpin and a larger
      L3 loop
<220> FEATURE:
<221> NAME/KEY: P3_hairpin
<222> LOCATION: (55)..(59)
```

<220> FEATURE:
<221> NAME/KEY: J3/1
<222> LOCATION: (60)..(61)
<220> FEATURE:
<221> NAME/KEY: P1_hairpin
<222> LOCATION: (62)..(69)

<400> SEQUENCE: 7
cacucauaua aucgcgugga uauggcacgc aaguuucuac cgggcaccgu aaaaguccga    60
cuagggug                                                            69

<210> SEQ ID NO 8
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<220> FEATURE:
<221> NAME/KEY: J1/2
<222> LOCATION: (9)..(13)
<223> OTHER INFORMATION: nucleobase U25 is replaced with a cytosine (C),
      which results in a more flexible and longer J1/2
<220> FEATURE:
<221> NAME/KEY: P2_hairpin
<222> LOCATION: (14)..(18)
<220> FEATURE:
<221> NAME/KEY: L2
<222> LOCATION: (19)..(25)
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(46)
<220> FEATURE:
<221> NAME/KEY: L3
<222> LOCATION: (47)..(53)
<220> FEATURE:
<221> NAME/KEY: P3_hairpin
<222> LOCATION: (54)..(59)
<220> FEATURE:
<221> NAME/KEY: J3/1
<222> LOCATION: (60)..(61)
<220> FEATURE:
<221> NAME/KEY: P1_hairpin
<222> LOCATION: (62)..(69)

<400> SEQUENCE: 8
cacucauaua accgcgugga uauggcacgc aaguuucuac cgggcaccgu aaauguccga    60
cuagggug                                                            69

<210> SEQ ID NO 9
<211> LENGTH: 69
<212> TYPE: RNA
<213> ORGANISM: Artificial Sequence
<220> FEATURE:
<223> OTHER INFORMATION: synthetic oligonucleotide
<220> FEATURE:
<221> NAME/KEY: P1_hairpin
<222> LOCATION: (1)..(8)
<223> OTHER INFORMATION: nucleobase A19 is replaced with a guanine
      residue (G), which results in a stable P1 hairpin
<220> FEATURE:
<221> NAME/KEY: J1/2
<222> LOCATION: (9)..(13)
<220> FEATURE:
<221> NAME/KEY: P2_hairpin

```
<222> LOCATION: (14)..(18)
<220> FEATURE:
<221> NAME/KEY: L2
<222> LOCATION: (19)..(25)
<220> FEATURE:
<221> NAME/KEY: P2_hairpin
<222> LOCATION: (26)..(30)
<220> FEATURE:
<221> NAME/KEY: J2/3
<222> LOCATION: (31)..(40)
<220> FEATURE:
<221> NAME/KEY: P3_hairpin
<222> LOCATION: (41)..(46)
<220> FEATURE:
<221> NAME/KEY: L3
<222> LOCATION: (47)..(53)
<220> FEATURE:
<221> NAME/KEY: P3_hairpin
<222> LOCATION: (54)..(59)
<220> FEATURE:
<221> NAME/KEY: J3/1
<222> LOCATION: (60)..(61)
<220> FEATURE:
<221> NAME/KEY: P1_hairpin
<222> LOCATION: (62)..(69)
<223> OTHER INFORMATION: nucleobase U77 is replaced with a cytosine
      residue (C), which results in a stable P1 hairpin

<400> SEQUENCE: 9
cacucguaua aucgcgugga uauggcacgc aaguuucuac cgggcaccgu aaauguccga    60
cuacggguug                                                           69

<210> SEQ ID NO 10
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 10
agcgcucaua                                                           10

<210> SEQ ID NO 11
<211> LENGTH: 10
<212> TYPE: RNA
<213> ORGANISM: Artificial Sequence
<220> FEATURE:
<223> OTHER INFORMATION: synthetic oligonucleotide

<400> SEQUENCE: 11
uaugggcgcu                                                           10

<210> SEQ ID NO 12
<211> LENGTH: 188
<212> TYPE: RNA
<213> ORGANISM: Artificial Sequence
<220> FEATURE:
<223> OTHER INFORMATION: synthetic oligonucleotide
<220> FEATURE:
<221> NAME/KEY: aptamer_domain
<222> LOCATION: (14)..(82)
<220> FEATURE:
<221> NAME/KEY: expression_platform
<222> LOCATION: (83)..(188)

<400> SEQUENCE: 12
aauauaauag gaacacucau auaaucgcgu ggauauggca cgcaaguuuc uaccgggcac    60
cguaaauguc cgacuauggg ugagcaaugg aaccgcacgu guacgguuuu uugugauauc   120
agcauugcuu gcucuuuauu ugagcgggca augcuuuuuu uauucucaua acggagguag   180
```

-continued acaggaug 188

<210> SEQ ID NO 13
<211> LENGTH: 188
<212> TYPE: RNA
<213> ORGANISM: Artificial Sequence
<220> FEATURE:
<223> OTHER INFORMATION: synthetic oligonucleotide
<220> FEATURE:
<221> NAME/KEY: aptamer_domain
<222> LOCATION: (14)..(82)
<220> FEATURE:
<221> NAME/KEY: expression_platform
<222> LOCATION: (83)..(188)

<400> SEQUENCE: 13 aauauaaauag gaacacucau auaaucgcgu ggauauggca cgcaaguuuc uaccgggcac  60
cguaaauguc cgacuauggg ugagcaaugg aaccgcacgu guacgguuuu uugugauauc 120
agcauugcuu gcucuuuauu ugagcggcga aucguuuuuu uauucucaua acggagguag 180
acaggaug 188

<210> SEQ ID NO 14
<211> LENGTH: 69
<212> TYPE: RNA
<213> ORGANISM: Artificial Sequence
<220> FEATURE:
<223> OTHER INFORMATION: synthetic oligonucleotide

<400> SEQUENCE: 14
cacucauaua aucgcgugga uauggcacgc aaguuucuac cgggcaccgu aaauguccga  60
cuaugggug 69

<210> SEQ ID NO 15
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 15
cacucauaua aucgcgugga uauggcacgc aaguuucuac cgggcaccgu aaauguccga  60
cuaugggug 69

<210> SEQ ID NO 16
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 16
cacucauaua aucgcgugga uauagcacgc aaguuucuac cgggcaccgu aaauguccga  60
cuaugggug 69

<210> SEQ ID NO 17
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 17

```
cacucauaua aucgcgugga uauagcacgc aaguuucuac cgggcacugu aaauguccga    60
cuaugggug                                                           69
```

<210> SEQ ID NO 18
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 18

```
cacucauaua aucgcgugga uaugacacgc aaguuucuac cgggcaccgu aaauguccga    60
cuaugggug                                                           69
```

<210> SEQ ID NO 19
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 19

```
cacucauaua aucgcgugga uauggcacgc aaguuucuac cgggcgccgu aaacguccga    60
cuaugggug                                                           69
```

<210> SEQ ID NO 20
<211> LENGTH: 73
<212> TYPE: RNA
<213> ORGANISM: Artificial sequence
<220> FEATURE:
<223> OTHER INFORMATION: synthetic oligonucleotide

<400> SEQUENCE: 20

```
agcgcucaua uaaucgcgug gauauggcac gcaaguuucu accgggcacc guaaauguuc    60
gacuaugggc gcu                                                      73
```

<210> SEQ ID NO 21
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 21

```
cacucauaua aucgcgugga uauggcacgc aaguuucuac cgggcaccgu aaaaguccga    60
cuaugggug                                                           69
```

<210> SEQ ID NO 22
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 22

```
cacucauaua accgcgugga uauggcacgc aaguuucuac cgggcaccgu aaauguccga    60
cuaugggug                                                           69
```

<210> SEQ ID NO 23
<211> LENGTH: 69
<212> TYPE: RNA
<213> ORGANISM: Artificial sequence

```
<220> FEATURE:
<223> OTHER INFORMATION: synthetic oligonucleotide

<400> SEQUENCE: 23
cacucguaua aucgcgugga uauggcacgc aaguuucuac cgggcaccgu aaauguccga      60 cuacggguq                                                             69

<210> SEQ ID NO 24
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 24
cacucauaua aucgcgugga uauggcacgc aaguuucuac cgggcaccgu aaauguccga      60
cuaugggug                                                             69

<210> SEQ ID NO 25
<211> LENGTH: 69
<212> TYPE: RNA
<213> ORGANISM: Artificial sequence
<220> FEATURE:
<223> OTHER INFORMATION: synthetic oligonucleotide

<400> SEQUENCE: 25
cacucauaua aucgcgugga uauggcacgc aaguuucuac cgggcaccgu aaauguccga      60
cuaugggug                                                             69

<210> SEQ ID NO 26
<211> LENGTH: 188
<212> TYPE: RNA
<213> ORGANISM: Artificial sequence
<220> FEATURE:
<223> OTHER INFORMATION: synthetic oligonucleotide

<400> SEQUENCE: 26
aauauaauag gaacacucau auaaucgcgu ggauauggca cgcaaguuuc uaccgggcac      60
cguaaauguc cgacuauggg ugagcaaugg aaccgcacgu guacgguuuu uugugauauc     120
agcauugcuu gcucuuuauu ugagcgggca augcuuuuuu uauucucaua acggagguag     180
acaggaug                                                             188

<210> SEQ ID NO 27
<211> LENGTH: 188
<212> TYPE: RNA
<213> ORGANISM: Artificial sequence
<220> FEATURE:
<223> OTHER INFORMATION: synthetic oligonucleotide

<400> SEQUENCE: 27
aauauaauag gaacacucau auaaucgcgu ggauauggca cgcaaguuuc uaccgggcac      60
cguaaauguc cgacuauggg ugagcaaug gaaccgcacg uguacgguuu uugugauau      120 cagcauugcu ugcucuuuau uugagcgggc aaugcuuuuu uauucucaua acggagguag     180
acaggaug                                                             188

<210> SEQ ID NO 28
<211> LENGTH: 192
<212> TYPE: RNA
<213> ORGANISM: Artificial sequence
<220> FEATURE:
```

```
<223> OTHER INFORMATION: synthetic oligonucleotide

<400> SEQUENCE: 28
ucaauauaau aggaacacuc auauaaucgc guggauaugg cacgcaaguu ucuaccgggc      60
accguaaaug uccgacuaug ggugagcaau ggaaccgcac guguacgguu uuuugugaua    120
ucagcauugc uugcucuuua uuugagcggc gaaucguuuu uuuauucuca uaacggaggu    180
agacaggaug aa                                                        192

<210> SEQ ID NO 29
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 29
taatacgact cactataggg actggtgagt actcaaccaa gtc                       43

<210> SEQ ID NO 30
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 30
taggaagcag cccagtagta gg                                              22
```

MATERIALS AND METHODS FOR CONTROLLING GENE EXPRESSION

RELATED APPLICATIONS

The present application is a U.S. national phase application filed under 35 U.S.C. § 371 of International Patent Application No. PCT/US2017/045100, titled MATERIALS AND METHODS FOR CONTROLLING GENE EXPRESSION, filed on Aug. 2, 2017, which claims the benefit of U.S. Provisional Application No. 62/376,328 filed Aug. 17, 2016; U.S. Provisional Application No. 62/376,325 filed Aug. 17, 2016; U.S. Provisional Application No. 62/432,077 filed Dec. 9, 2016; and U.S. Provisional Application No. 62/432,160 filed Dec. 9, 2016, all of which are incorporated herein by reference in their entirety.

FIELD

The present application provides materials and methods for identifying the folding routes and conformational transition states of biological molecules comprising one or more aptamer domains. The present application also provides materials and methods for controlling gene expression by controlling the folding and conformational transition states of the aptamer domains.

INCORPORATION BY REFERENCE OF SEQUENCE LISTING

This application contains a Sequence Listing in computer readable form (filename: 160408PCT_ST25 060523; 14,641 bytes ASCII text file; created Jun. 5, 2023), which is incorporated herein by reference in its entirety and forms part of the disclosure.

BACKGROUND

A riboswitch is a non-coding RNA sequence present in the 5'-untranslated region of mRNA. An aptamer domain within the riboswitch selectively binds to metabolites and ligands to control gene expression.

Riboswitches act as natural sensors for changing environmental conditions, which allow living organisms, such as bacteria, fungi, and plants to survive.

The presence of riboswitches in the human genome has been speculated since less than 5% of the human genome is translated to form proteins, while the remaining greater than 95% of the human genome is transcribed as non-coding RNAs, such as riboswitches, which remain untranslated.

Despite efforts from researchers worldwide who have tried to better understand riboswitches, there still remains a critical need for understanding the folding routes, the real-time conformational transition states, and the switching mechanism of riboswitches. This knowledge of riboswitches will provide a mechanistic view of RNA-mediated gene regulation in relation to the transcriptional machinery, which can be applied to develop RNA-based drug targets that control gene expression.

SUMMARY

Provided herein is a method of detecting a biological molecule in a patient, the method comprising: obtaining a biological sample from the patient; releasing the biological molecule from the biological sample, wherein the biological molecule comprises one or more riboswitch, wherein the one or more riboswitch comprises one or more aptamer domain; exposing the biological molecule comprising one or more riboswitch to a chemically modified ligand, wherein a binding of the chemically modified ligand to the biological molecule comprising one or more riboswitch is required for optical detection of the biological molecule comprising one or more riboswitch by fluorescence or absorbance; and detecting fluorescence of the chemically modified ligand bound to the biological molecule comprising one or more riboswitch after exposing the biological molecule comprising one or more riboswitch to the chemically modified ligand.

The biological sample can be blood, blood derivatives, urine, cerebro-spinal fluid, saliva, a tumor biospecimen, a tissue biospecimen, or combinations thereof.

The biological molecule can comprise one or more of: a bacterium, a virus, a fungus, a protozoan, and combinations thereof. The biological molecule can comprise deoxyribonucleic acid (DNA). The biological molecule can comprise ribonucleic acid (RNA). The RNA can be human RNA, microbial RNA, parasitic RNA, bacterial RNA, viral RNA, fungal RNA, plant RNA, or combinations thereof. The RNA can be bacterial RNA. The biological molecule can comprise a protein. The biological molecule can comprise a carbohydrate.

The one or more riboswitch can be one or more purine riboswitch. The one or more purine riboswitch can be one or more guanine riboswitch or one or more adenine riboswitch. The one or more riboswitch can be one or more mutated riboswitch not found in nature. The one or more riboswitch can be one or more mutated purine riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more aptamer domain can be one or more mutated aptamer domain not found in nature. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The chemically modified ligand can be a chemically modified purine, a chemically modified guanine, a chemically modified adenine, derivatives thereof, or combinations thereof.

The releasing step can comprise: applying osmotic stress to the biological sample, using chemical methods on the biological sample, using enzymatic methods on the biological sample, or combinations thereof.

The detection step can comprise measuring the fluorescence or other optical properties of the chemically modified ligand bound to the biological molecule comprising one or more riboswitch to determine the concentration of the biological molecule comprising one or more riboswitch in the biological sample.

The method can further comprise the step of evaluating the concentration of the biological molecule comprising one or more riboswitch in the biological sample with respect to a threshold. The method can further comprise the step of prescribing a treatment to the patient if the concentration of the biological molecule comprising one or more riboswitch in the biological sample exceeds the threshold. The method can further comprise the step of prescribing a treatment to the patient if the concentration of the biological molecule comprising one or more riboswitch in the biological sample is less than the threshold.

The method can further comprise the step of detecting the fluorescence of the chemically modified ligand before exposing the biological molecule comprising one or more riboswitch to the chemically modified ligand. The method can further comprise the step of detecting the fluorescence of the chemically modified ligand before exposing the biological molecule comprising one or more mutated riboswitch to the chemically modified ligand, wherein the one or more mutated riboswitch comprises SEQ ID NO: 13. The method can further comprise the step of detecting the fluorescence of the chemically modified ligand before exposing the biological molecule comprising one or more riboswitch comprising one or more mutated aptamer domain to the chemically modified ligand, wherein the one or more mutated aptamer domain comprises a sequence selected from the group consisting of SEQ ID NOs: 2-9 of the Sequence Listing and combinations thereof.

The method can further comprise a fluorimeter configured to detect the fluorescence or other suitable unit or instrument to detect optically relevant signals. The fluorimeter can comprise a filter fluorimeter. The fluorimeter can comprise a spectrofluorimeter.

Provided herein is a method of detecting a biological molecule, the method comprising: obtaining a biological sample; releasing the biological molecule from the biological sample, wherein the biological molecule comprises one or more riboswitch, wherein the one or more riboswitch comprises one or more aptamer domain; exposing the biological molecule comprising one or more riboswitch to a chemically modified ligand, wherein a binding of the chemically modified ligand to the biological molecule comprising one or more riboswitch is required for optical detection of the biological molecule comprising one or more riboswitch by fluorescence or absorbance; and detecting fluorescence of the chemically modified ligand bound to the biological molecule comprising one or more riboswitch after exposing the biological molecule comprising one or more riboswitch to the chemically modified ligand.

The biological sample can be a contaminated water sample or a contaminated food sample.

The one or more riboswitch can be one or more mutated riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more aptamer domain can be one or more mutated aptamer domain not found in nature. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

Provided herein is a method of detecting a biological molecule in a patient, the method comprising: obtaining a biological sample from the patient; releasing the biological molecule from the biological sample; exposing the biological molecule to a chemically modified ligand, wherein the chemically modified ligand comprises one or more riboswitch comprising one or more aptamer domain, wherein a binding of the chemically modified ligand comprising one or more riboswitch to the biological molecule is required for optical detection of the biological molecule by fluorescence or absorbance; and detecting fluorescence of the chemically modified ligand comprising one or more riboswitch bound to the biological molecule after exposing the biological molecule to the chemically modified ligand comprising one or more riboswitch.

The biological sample can be blood, blood derivatives, urine, cerebro-spinal fluid, saliva, a tumor biospecimen, and a tissue biospecimen.

The biological molecule can comprise one or more of: a bacterium, a virus, a fungus, a protozoan, and combinations thereof. The biological molecule can comprise deoxyribonucleic acid (DNA). The biological molecule can comprise ribonucleic acid (RNA). The RNA can be human RNA, microbial RNA, parasitic RNA, bacterial RNA, viral RNA, fungal RNA, plant RNA, or combinations thereof. The RNA can be bacterial RNA. The biological molecule can comprise a protein. The biological molecule can comprise a carbohydrate.

The biological molecule can comprise one or more metabolite or ligand capable of binding to the one or more aptamer domain of the chemically modified ligand.

The one or more riboswitch can be one or more purine riboswitch. The one or more purine riboswitch can be one or more guanine riboswitch or one or more adenine riboswitch. The one or more riboswitch can be one or more mutated riboswitch not found in nature. The one or more riboswitch can be one or more mutated purine riboswitch not found in nature. The one or more riboswitch can be one or more mutated riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more aptamer domain can comprise one or more mutated aptamer domain not found in nature. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The releasing step can comprise: applying osmotic stress to the biological sample, using chemical methods on the biological sample, using enzymatic methods on the biological sample, or combinations thereof.

The detecting step can comprise measuring the fluorescence of the chemically modified ligand comprising one or more riboswitch bound to the biological molecule to determine the concentration of the biological molecule in the biological sample.

The method can further comprise the step of evaluating the concentration of the biological molecule in the biological sample with respect to a threshold. The method can further comprise the step of prescribing a treatment to the patient if the concentration of the biological molecule in the biological sample exceeds the threshold. The method can further comprise the step of prescribing a treatment to the patient if the concentration of the biological molecule in the biological sample is less than the threshold.

The method can further comprise the step of detecting the fluorescence of the chemically modified ligand comprising one or more riboswitch before exposing the biological molecule to the chemically modified ligand. The method can further comprising the step of detecting the fluorescence of the chemically modified ligand comprising one or more mutated riboswitch before exposing the biological molecule to the chemically modified ligand, wherein the one or more mutated riboswitch comprises SEQ ID NO: 13. The method can further comprise the step of detecting the fluorescence of the chemically modified ligand comprising one or more riboswitch comprising one or more mutated aptamer domain before exposing the biological molecule to the chemically modified ligand, wherein the one or more mutated aptamer domain comprises a sequence selected from the group consisting of SEQ ID NOs: 2-9 of the Sequence Listing and combinations thereof.

The method can further comprise a fluorimeter configured to detect the fluorescence or other suitable unit or instrument to detect optically relevant signals. The fluorimeter can comprise a filter fluorimeter. The fluorimeter can comprise a spectrofluorimeter.

Provided herein is a method of detecting a biological molecule, the method comprising: obtaining a biological sample; releasing the biological molecule from the biological sample; exposing the biological molecule to a chemically modified ligand, wherein the chemically modified ligand comprises one or more riboswitch comprising one or more aptamer domain, wherein a binding of the chemically modified ligand comprising one or more riboswitch to the biological molecule is required for optical detection of the biological molecule by fluorescence or absorbance; and detecting fluorescence of the chemically modified ligand comprising one or more riboswitch bound to the biological molecule after exposing the biological molecule to the chemically modified ligand comprising one or more riboswitch.

The biological sample can be a contaminated water sample or contaminated food sample.

The one or more riboswitch can be one or more mutated riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more aptamer domain can be one or more mutated aptamer domain not found in nature. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

Provided herein is a biological sensor comprising: a biological molecule not found in nature comprising one or more aptamer domain, wherein the one or more aptamer domain comprises: one or more hairpin; one or more loop; and one or more junction; and one or more ligand capable of binding to the one or more aptamer domain, wherein the one or more ligand binds the one or more aptamer domain switching the one or more aptamer domain between one or more structural conformations.

The one or more aptamer domain can be one or more purine aptamer domain. The one or more purine aptamer domain can be one or more guanine aptamer domain or one or more adenine aptamer domain.

The biological molecule can be human RNA, microbial RNA, parasitic RNA, bacterial RNA, viral RNA, fungal RNA, plant RNA, and combinations thereof.

The one or more hairpin can be P1, P2, or P3.

The one or more loop can be L2 or L3.

The one or more junction can be J1/2, J2/3, or J3/1.

The one or more aptamer domain can form one or more of: a P2 helix conformation, a P2-P3 helix conformation, a L2-L3 unkissed conformation, a L2-L3 kissed conformation, and a guanine-bound conformation.

Provided herein is biological sensor comprising: a biological molecule not found in nature comprising one or more mutated aptamer domain, wherein the one or more mutated aptamer domain comprises: one or more hairpin; one or more loop; and one or more junction; and one or more ligand capable of binding to the one or more mutated aptamer domain, wherein the one or more ligand binds the one or more mutated aptamer domain switching the one or more aptamer domain between one or more structural conformations; wherein a rate in which the one or more mutant aptamer domain switches between the one or more structural conformations is faster than a rate in which one or more wild-type aptamer domain switches between the one or more structural conformations.

The one or more mutated aptamer domain can be one or more mutated purine aptamer domain not found in nature. The one or more mutated purine aptamer domain can be one or more mutated guanine aptamer domain or one or more mutated adenine aptamer domain.

The biological molecule can be human RNA, microbial RNA, parasitic RNA, bacterial RNA, viral RNA, fungal RNA, plant RNA, or combinations thereof.

The one or more hairpin can be P1, P2, or P3. Once or more of the P1, P2, and P3 can comprise a base pair mutation. The P1 can comprise a sequence selected from the group consisting of: SEQ ID NOs: 10-11 of the Sequence Listing and combinations thereof.

The one or more loop can be L2 or L3. One or more of the L2 and L3 can comprise a base pair mutation.

The one or more junction can be J1/2, J2/3, or J3/1. One or more of the J1/2, J2/3, and J3/1 can comprise a base pair mutation.

The one or more mutated aptamer domain can form one or more of: a P2 helix conformation; a P2-P3 helix conformation; a L2-L3 unkissed conformation; a L2-L3 kissed conformation; and a guanine-bound conformation. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

Provided herein is a biological sensor comprising: a biological molecule not found in nature comprising one or more mutated aptamer domain, wherein the one or more mutated aptamer domain comprises: one or more hairpin; one or more loop; and one or more junction; and one or more ligand capable of binding to the one or more mutated aptamer domain, wherein the one or more ligand binds the one or more mutated aptamer domain switching the one or more aptamer between one or more structural conformations; wherein the rate in which the one or more mutant aptamer domain switches between the one or more structural conformations is slower than the rate in which one or more wild-type aptamer domain switches between the one or more structural conformations.

The one or more mutated aptamer domain can be one or more mutated purine aptamer domain. The one or more mutated purine aptamer domain can be one or more mutated guanine aptamer domain or one or more mutated adenine aptamer domain.

The biological molecule can be human RNA, microbial RNA, parasitic RNA, bacterial RNA, viral RNA, fungal RNA, plant RNA, or combinations thereof.

The one or more hairpin can be P1, P2, or P3. One or more of the P1, P2, and P3 can comprise a base pair mutation. The P1 can comprise a sequence selected from the group consisting of: SEQ ID NOs: 10-11 of the Sequence Listing and combinations thereof.

The one or more loop can be L2 or L3. One or more of the L2 and L3 can comprise a base pair mutation.

The one or more junction can be J1/2, J2/3, or J3/1. One or more of the J1/2, J2/3, and J3/1 can comprise a base pair mutation.

The one or more mutated aptamer domain can form one or more of: a P2 helix conformation; a P2-P3 helix conformation; a L2-L3 unkissed conformation; a L2-L3 kissed conformation; and a guanine-bound conformation. The one or more mutated aptamer domain can comprise a sequence selected from the group consisting of: SEQ ID NOs: 2-9 of the Sequence Listing and combintations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

Provided herein is a biological sensor, comprising: a biological molecule not found in nature comprising one or more aptamer domain, wherein the one or more aptamer domain comprise: one or more hairpin; one or more loop; and one or more junction.

The one or more aptamer domain can form one or more of: a P2 helix conformation, a P2-P3 helix conformation, a L2-L3 unkissed conformation, a L2-L3 kissed conformation, and a guanine-bound conformation when a ligand capable of binding to the one or more aptamer domain binds the one or more aptamer domain switching the one or more aptamer domain between the one or more structural conformations.

Provided herein is a biological sensor, comprising: a biological molecule not found in nature comprising one or more mutated aptamer domain, wherein the one or more mutated aptamer domain comprise: one or more hairpin; one or more loop; and one or more junction.

The one or more mutated aptamer domain can form one or more of: a P2 helix conformation, a P2-P3 helix conformation, a L2-L3 unkissed conformation, a L2-L3 kissed conformation, and a guanine-bound conformation. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

Provided herein is a biological sensor, comprising: a biological molecule not found in nature comprising one or more mutated riboswitch. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

Provided herein is a microchip comprising any of the biological sensors disclosed herein.

Provided herein is a method of making a biological sensor for one or more metabolite, the method comprising: introducing a biological molecule not found in nature into a cell, the biomolecule comprising one or more riboswitch, wherein the one or more riboswitch comprises one or more aptamer domain.

The one or more aptamer domain can form one or more of: a P2 helix conformation, a P2-P3 helix conformation, a L2-L3 unkissed conformation, a L2-L3 kissed conformation, and a guanine-bound conformation.

The cell can be a eukaryotic cell. The cell can be a prokaryotic cell.

The one or more metabolite can be nucleotides and nucleobases, amino acids, vitamins, ions, or cofactors.

The biological molecule can comprise RNA. The RNA can be human RNA, microbial RNA, parasitic RNA, bacterial RNA, viral RNA, fungal RNA, plant RNA, or combinations thereof. The RNA can be bacterial RNA. The biological molecule can comprise a protein. The biological molecule can comprise a carbohydrate.

Provided herein is a method of making a biological sensor for one or more metabolite, the method comprising: introducing a biological molecule not found in nature into a cell, the biomolecule comprising one or more riboswitch, wherein the one or more riboswitch comprises one or more mutated aptamer domain.

The one or more mutated aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The cell can be a eukaryotic cell. The cell can be a prokaryotic cell.

The one or more metabolite can be nucleotides and nucleobases, amino acids, vitamins, ions, or cofactors.

The biological molecule can comprise RNA. The RNA can be human RNA, microbial RNA, parasitic RNA, bacterial RNA, viral RNA, fungal RNA, plant RNA, or combinations thereof. The RNA can be bacterial RNA. The biological molecule can comprise a protein. The biological molecule can comprise a carbohydrate.

Provided herein is a method of making a biological sensor for one or more metabolite, the method comprising: introducing a biological molecule not found in nature into a cell, the biomolecule comprising one or more mutated riboswitch.

The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

Provided herein is a biological molecule not found in nature comprising: one or more mutated aptamer domain, wherein the one or more mutated aptamer domain comprise: one or more hairpin; one or more loop; and one or more junction.

The one or more mutated aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The biological molecule can be human RNA, microbial RNA, parasitic RNA, bacterial RNA, viral RNA, fungal RNA, plant RNA, guide RNA (gRNA), or combinations thereof.

Provided herein is a biological molecule not found in nature comprising one or more mutated riboswitch.

The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

Provided herein is a method of controlling gene expression, the method comprising: providing a biological molecule comprising one or more aptamer domain; exposing the biological molecule comprising one or more aptamer domain to a first ligand capable of binding to the one or more aptamer domain, wherein the first ligand binds the biological molecule comprising one or more aptamer domain switching the one or more aptamer domain to a first set of one or more structural conformations; and exposing the biological molecule comprising one or more aptamer domain to a second ligand capable of binding to the one or more aptamer domain, wherein the second ligand binds the biological molecule comprising one or more aptamer domain switching the one or more aptamer domain to a second set of one or more structural conformations, thereby terminating gene expression.

The one or more aptamer domain can be one or more purine aptamer domain. The one or more purine aptamer domain can be one or more guanine aptamer domain or one or more adenine aptamer domain.

The biological molecule can be human RNA, microbial RNA, parasitic RNA, bacterial RNA, viral RNA, fungal RNA, plant RNA, or combinations thereof.

The one or more aptamer domain can comprise one or more hairpin, one or more loop, and one or more junction.

The one or more hairpin can be P1, P2, or P3.

The one or more loop can be L2 or L3.

The one or more junction can be J1/2, J2/3, or J3/1.

The one or more aptamer domain can form one or more of: a P2 helix conformation, a P2-P3 helix conformation, a L2-L3 unkissed conformation, a L2-L3 kissed conformation, and a guanine-bound conformation.

The first set of one or more structural conformations can be a P2 helix conformation, a P2-P3 helix conformation, or both P2 helix conformation and P2-P3 helix conformations.

The second set of one or more structural conformations can be a L2-L3 unkissed conformation, a L2-L3 kissed conformation, a guanine-bound conformation, combinations thereof, or all three conformations.

Provided herein is a method of controlling gene expression, the method comprising: providing a biological molecule comprising one or more aptamer domain; exposing the biological molecule comprising one or more aptamer domain to a first ligand capable of binding to the one or more aptamer domain, wherein the first ligand binds the biological molecule comprising one or more aptamer domain switching the one or more aptamer domain to a first set of one or more structural conformations; and exposing the biological molecule comprising one or more aptamer domain to a second ligand capable of binding to the one or more aptamer domain, wherein the second ligand binds the biological molecule comprising one or more aptamer domain switching the one or more aptamer domain to a second set of one or more structural conformations, thereby permitting gene expression.

The one or more aptamer domain can be one or more purine aptamer domain. The one or more purine aptamer domain can be one or more guanine aptamer domain or one or more adenine aptamer domain.

The biological molecule can be human RNA, microbial RNA, parasitic RNA, bacterial RNA, viral RNA, fungal RNA, plant RNA, or combinations thereof.

The one or more aptamer domain can comprise one or more hairpin, one or more loop, or one or more junction.

The one or more hairpin can be P1, P2, or P3.

The one or more loop can be L2 or L3.

The one or more junction can be J1/2, J2/3, or J3/1.

The one or more aptamer domain can form one or more of: a P2 helix conformation, a P2-P3 helix conformation, a L2-L3 unkissed conformation, a L2-L3 kissed conformation, and a guanine-bound conformation.

The first set of one or more structural conformations can be a P2 helix conformation, a P2-P3 helix conformation, or both P2 helix conformation and P2-P3 helix conformations.

The second set of one or more structural conformations can be a L2-L3 unkissed conformation, a L2-L3 kissed conformation, a guanine-bound conformation, combinations thereof, or all three conformations.

Provided herein is a method of controlling gene expression, the method comprising: providing a biological molecule comprising one or more mutated aptamer domain; exposing the biological molecule comprising one or more mutated aptamer domain to a first ligand capable of binding to the one or more mutated aptamer domain, wherein the first ligand binds the biological molecule comprising one or more mutated aptamer domain switching the one or more aptamer domain to a first set of one or more structural conformations; and exposing the biological molecule comprising one or more mutated aptamer domain to a second ligand capable of binding to the one or more mutated aptamer domain, wherein the second ligand binds the biological molecule comprising one or more mutated aptamer domain switching the one or more aptamer domain to a second set of one or more second structural conformations, thereby terminating gene expression.

The one or more mutated aptamer domain can be one or more mutated purine aptamer domain. The one or more mutated purine aptamer domain can be one or more mutated guanine aptamer domain or one or more mutated adenine aptamer domain.

The biological molecule can be human RNA, microbial RNA, parasitic RNA, bacterial RNA, viral RNA, fungal RNA, plant RNA, or combinations thereof.

The one or more mutated aptamer domain can comprise one or more hairpin, one or more loop, or one or more junction.

The one or more hairpin can be P1, P2, or P3. One or more of the P1, P2, and P3 can comprise a base pair mutation. The P1 can comprise a sequence selected from the group consisting of: SEQ ID NOs: 10-11 of the Sequence Listing and combinations thereof.

The one or more loop can be L2 or L3. One or more of the L2 and L3 can comprise a base pair mutation.

The one or more junction can be J1/2, J2/3, or J3/1. One or more of the J1/2, J2/3, and J3/1 can comprise a base pair mutation.

The one or more mutated aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The one or more mutant aptamer domain can switch between the second set of one or more structural conformations at a slower rate than the wild type aptamer domain switches between a second set of one or more structural conformations. The one or more mutant aptamer domain can switch between the second set of one or more structural conformations at a faster rate than the wild type aptamer domain switches between a second set of one or more structural conformations.

Provided herein is a method of controlling gene expression, the method comprising: providing a biological molecule comprising one or more mutated aptamer domain; exposing the biological molecule comprising one or more mutated aptamer domain to a first ligand capable of binding to the one or more mutated aptamer domain, wherein the first ligand binds the biological molecule comprising one or more mutated aptamer domain switching the one or more aptamer domain to a first set of one or more structural conformations; and exposing the biological molecule comprising one or more mutated aptamer domain to a second ligand capable of binding to the one or more mutated aptamer domain, wherein the second ligand binds the biological molecule comprising one or more mutated aptamer domain switching the one or more aptamer domain to a second set of one or more structural conformations, thereby permitting gene expression.

The one or more mutated aptamer domain can be one or more mutated purine aptamer domain. The one or more mutated purine aptamer domain can be one or more mutated guanine aptamer domain or one or more mutated adenine aptamer domain.

The biological molecule can be human RNA, microbial RNA, parasitic RNA, bacterial RNA, viral RNA, fungal RNA, plant RNA, or combinations thereof.

The one or more mutated aptamer domain can comprise one or more hairpin, one or more loop, or one or more junction.

The one or more hairpin can be P1, P2, or P3. One or more of the P1, P2, and P3 can comprise a base pair mutation. P1 can comprise a sequence selected from the group consisting of: SEQ ID NOs: 10-11 of the Sequence Listing and combinations thereof.

The one or more loop can be L2 or L3. One or more of the L2 and L3 can comprise a base pair mutation.

The one or more junction can be J1/2, J2/3, or J3/1. One or more of the J1/2, J2/3, or J3/1 can comprise a base pair mutation.

The one or more mutated aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The one or more mutant aptamer domain can switch between the second set of one or more structural conformations at a slower rate than the wild type aptamer domain switches between a second set of one or more structural conformations. The one or more mutant aptamer domain can switch between the second set of one or more structural conformations at a faster rate than the wild type aptamer domain switches between a second set of one or more structural conformations.

Provided herein is method of evaluating structural conformational switching changes of a biological molecule comprising one or more riboswitch in response to one or more metabolite, wherein the one or more metabolite acts as a ligand to induce structural conformational switching, the method comprising: obtaining a biological molecule wherein the biological molecule comprises one or more riboswitch wherein the one or more riboswitch comprises one or more aptamer domain; subjecting the biological molecule comprising one or more riboswitch to optical tweezers for identification of a rate of conformational switching and a barrier in a structural conformational switching rearrangement; adding one or more metabolite to the biological molecule comprising one or more riboswitch;

and evaluating the rate of conformational switching and the structural conformational switching changes of the biological molecule comprising one or more riboswitch in response to the one or more metabolite.

The one or more metabolite can be nucleotides and nucleobases, amino acids, vitamins, ions, and cofactors.

The method can further comprise the step of constructing a switch, utilizing data obtained during the evaluating step.

The biological molecule can comprise RNA. The RNA can be human RNA, microbial RNA, parasitic RNA, bacterial RNA, viral RNA, fungal RNA, plant RNA, or combinations thereof. The RNA can be bacterial RNA. The biological molecule can comprise a protein. The biological molecule can comprise a carbohydrate.

The method can further comprise the step of creating a modified biological molecule that has a RNA sequence that has been mutated relative to the RNA sequence of the wild-type biological molecule.

The structural conformational switching of the modified biological molecule can be faster than the structural conformational switching of the wild-type biological molecule. The structural conformational switching of the modified biological molecule can be slower than the structural conformational switching of the wild-type biological molecule.

The method can further comprise the step of constructing a switch, utilizing data for the modified biological molecule.

The mutated RNA sequence can be an RNA sequence comprising one or more mutated riboswitches. The structural conformational switching of the RNA sequence comprising one or more mutated riboswitches can be faster than the structural conformational switching of the wild-type RNA sequence. The structural conformational switching of the RNA sequence comprising one or more mutated riboswitches can be slower than the structural conformational switching of the wild-type RNA sequence.

The mutated RNA sequence can be an RNA sequence comprising one or more riboswitches comprising one or more mutated aptamer domain. The structural conformational switching of the RNA sequence comprising one or more riboswitches comprising one or more mutated aptamer domains can be faster than the structural conformational switching of the wild-type RNA sequence. The structural conformational switching of the RNA sequence comprising one or more riboswitches comprising one or more mutated aptamer domains can be slower than the structural conformational switching of the wild-type RNA sequence.

The method can further comprise the step of constructing a modified biological molecule comprising one or more riboswitch with requisite switch, utilizing data obtained during the evaluating step.

The one or more aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

Provided herein is a method of evaluating structural conformational switching changes of a biological molecule comprising one or more riboswitch in response to one or more metabolite, wherein the one or more metabolite acts as a ligand to induce structural conformational switching, the method comprising: obtaining a biological molecule wherein the biological molecule comprises one or more riboswitch wherein the one or more riboswitch comprises one or more aptamer domain; subjecting the biological molecule comprising one or more riboswitch to acoustic tweezers for identification of a rate of conformational switching and a barrier in a structural conformational switching rearrangement; adding one or more metabolite to the biological molecule comprising one or more riboswitch; and evaluating the rate of conformational switching and the structural conformational switching changes of the biological molecule comprising one or more riboswitch in response to the one or more metabolite.

The one or more metabolite can be nucleotides and nucleobases, amino acids, vitamins, ions, or cofactors.

The method can further comprise the step of constructing a switch, utilizing data obtained during the evaluating step.

The biological molecule can comprise an RNA. The RNA can be human RNA, microbial RNA, parasitic RNA, bacterial RNA, viral RNA, fungal RNA, plant RNA, or combinations thereof. The RNA can be bacterial RNA. The biological molecule can comprise a protein. The biological molecule can comprise a carbohydrate.

The method can further comprise the step of creating a modified biological molecule that has a RNA sequence that has been mutated relative to the RNA sequence of the wild-type biological molecule.

The structural conformational switching of the modified biological molecule can be faster than the structural conformational switching of the wild-type biological molecule. The structural conformational switching of the modified biological molecule can be slower than the structural conformational switching of the wild-type biological molecule.

The method can further comprise the step of constructing a switch, utilizing data from the modified biological molecule.

The mutated RNA sequence can be an RNA sequence comprising one or more mutated riboswitches. The structural conformational switching of the RNA sequence comprising one or more mutated riboswitches can be faster than the structural conformational switching of the wild-type RNA sequence. The structural conformational switching of the RNA sequence comprising one or more mutated riboswitches can be slower than the structural conformational switching of the wild-type RNA sequence.

The mutated RNA sequence can be an RNA sequence comprising one or more riboswitches comprising one or more mutated aptamer domain. The structural conformational switching of the RNA sequence comprising one or more riboswitches comprising one or more mutated aptamer domains can be faster than the structural conformational switching of the wild-type RNA sequence. The structural conformational switching of the RNA sequence comprising one or more riboswitches comprising one or more mutated aptamer domains can be slower than the structural conformational switching of the wild-type RNA sequence.

The step of constructing a modified biological molecule comprising one or more riboswitch with requisite switch, utilizing data obtained during the evaluating step.

The one or more aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can form one or more of: a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

Provided herein is a method of identifying one or more transition state of a biological molecule, the method comprising: obtaining the biological molecule wherein the biological molecule comprises one or more riboswitch wherein the one or more riboswitch comprises one or more aptamer domain; subjecting the biological molecule comprising one or more riboswitch to optical tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more riboswitch wherein the one or more riboswitch comprises one or more mutated aptamer domain; subjecting the biological molecule comprising one or more riboswitch to optical tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more mutated riboswitch; subjecting the biological molecule comprising one or more mutated riboswitch to optical tweezers to identify one or more transition states of the biological molecule and a rate of conformational switching between the one or more transition state of the biological molecule; adding one or more metabolite to the biological molecule comprising one or more mutated riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more riboswitch wherein the one or more riboswitch comprises one or more aptamer domain; subjecting the biological molecule comprising one or more riboswitch to acoustic tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more riboswitch wherein the one or more riboswitch comprises one or more mutated aptamer domain; subjecting the biological molecule comprising one or more riboswitch to acoustic tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more mutated riboswitch; subjecting the biological molecule comprising one or more mutated riboswitch to acoustic tweezers to identify one or more transition states of the biological molecule and a rate of conformational switching between the one or more transition state of the biological molecule; adding one or more metabolite to the biological molecule comprising one or more mutated riboswitch; and evaluating the structure of the one or more transition state of the biological molecule and the rate of conformational switching between the one or more transition state in response to the one or more metabolite.

It is understood that the inventions described in this specification are not limited to the examples summarized in this Summary. Various other aspects are described and exemplified herein.

BRIEF DESCRIPTION OF THE DRAWINGS

Various aspects of materials and methods for controlling gene expression disclosed and described in this specification can be better understood by reference to the accompanying figures, in which:

FIG. 2C describes the dual beam optical tweezers system.

FIG. 2D describes the dual beam optical tweezers system.

FIG. 8C shows the dissociation constants ($K_D$) and the thermodynamic parameters from isothermal titration calorimetry (ITC) experiments for the wild-type guanine aptamer RNA and the guanine aptamer RNA for mutants m1-m4 and m6-m7.

FIG. 12B is a chart showing force-dependent folding rates for the tertiary and the secondary structural elements in the m1 mutant aptamer.

FIG. 12C is a chart showing force-dependent folding rates for the tertiary and the secondary structural elements in the m2 mutant aptamer.

FIG. 12D is a chart showing force-dependent folding rates for the tertiary and the secondary structural elements in the m3 mutant aptamer.

FIG. 12G is a chart showing force-dependent folding rates for the tertiary and the secondary structural elements in the m7 mutant aptamer.

FIG. 12H is a chart showing force-dependent folding rates for the tertiary and the secondary structural elements in the m8 mutant aptamer.

BRIEF DESCRIPTION OF THE SEQUENCE LISTING

SEQ ID NO: 1 is a 69-nucleotide full-length wild-type guanine sensing aptamer RNA sequence from xpt-pbuX operon in *B. subtilis*.

SEQ ID NO: 2 is a full-length m1 mutant guanine sensing aptamer RNA sequence.

SEQ ID NO: 3 is a full-length m2 mutant guanine sensing aptamer RNA sequence.

SEQ ID NO: 4 is a full-length m3 mutant guanine sensing aptamer RNA sequence.

SEQ ID NO: 5 is a full-length m4 mutant guanine sensing aptamer RNA sequence.

SEQ ID NO: 6 is a full-length m5 mutant guanine sensing aptamer RNA sequence.

SEQ ID NO: 7 is a full-length m6 mutant guanine sensing aptamer RNA sequence.

SEQ ID NO: 8 is a full-length m7 mutant guanine sensing aptamer RNA sequence.

SEQ ID NO: 9 is a full-length m8 mutant guanine sensing aptamer RNA sequence.

SEQ ID NO: 10 is an RNA sequence for the P1 hairpin of the m5 mutant guanine sensing aptamer.

SEQ ID NO: 11 is an RNA sequence for the P1 hairpin of the m5 mutant guanine sensing aptamer.

SEQ ID NO: 12 is a full-length wild-type guanine riboswitch sequence comprising the aptamer domain and expression platform.

SEQ ID NO: 13 is a full-length mutant guanine riboswitch sequence comprising the aptamer domain and expression platform.

DETAILED DESCRIPTION

Riboswitches

Riboswitches are non-coding elements present in the 5' untranslated regions of mRNAs. Riboswitches comprise an aptamer domain and an expression platform.

Figure 1A:
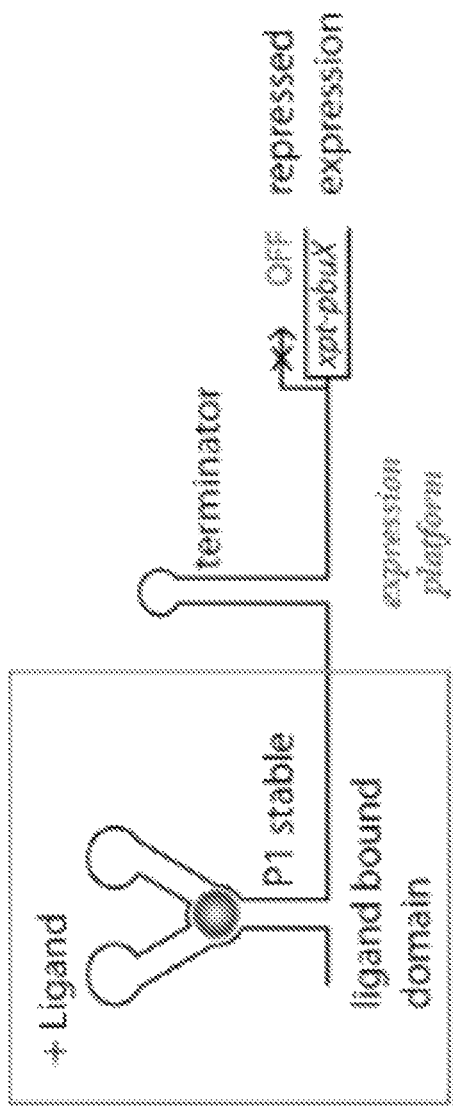
FIG. 1A depicts a ligand bound aptamer domain, which terminates gene expression.

The aptamer domain can be selectively bound to by metabolites or ligands to control gene expression (FIG. 1A). Metabolite or ligand binding to the aptamer domain results in a stable terminator hairpin structure in the expression platform resulting in terminated gene expression.

Figure 1B:
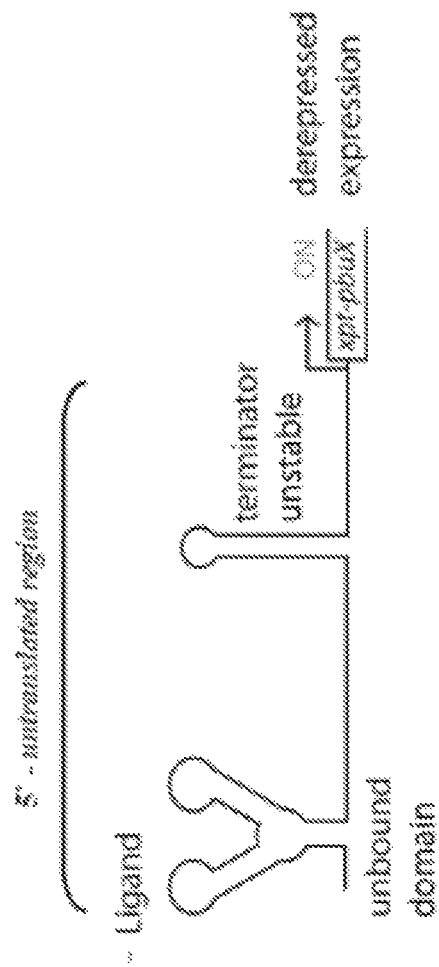
FIG. 1B depicts an unbound aptamer domain, which permits gene expression.
Figure 2A:
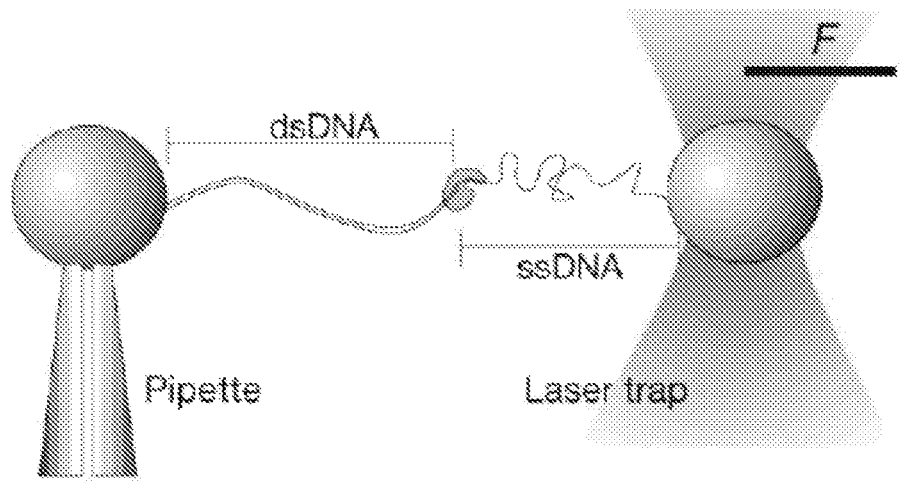
FIG. 2A depicts a single guanine aptamer RNA connected to a bead via handles.
Figure 2B:
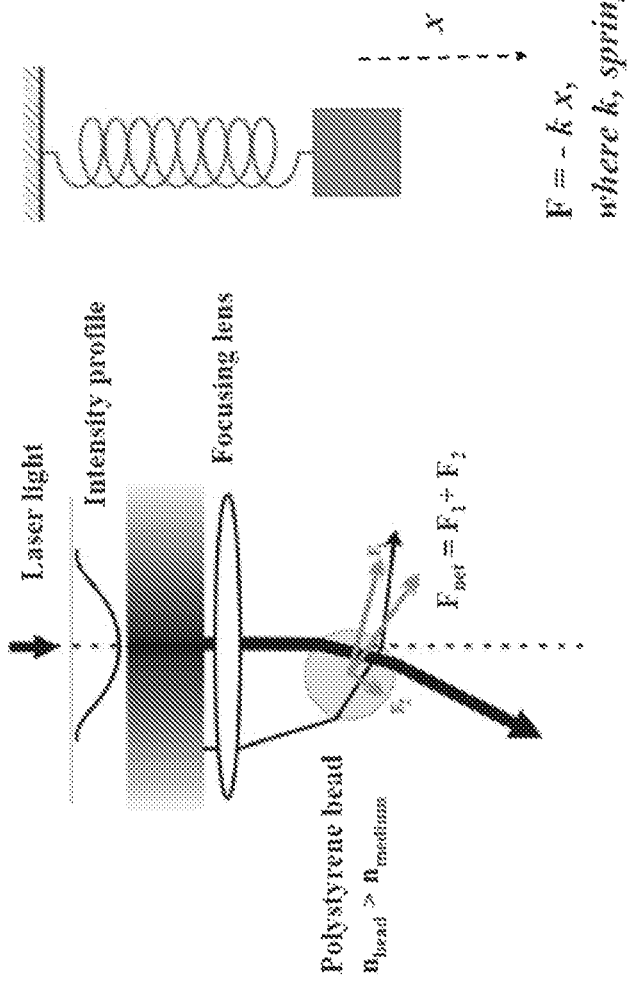
FIG. 2B describes the dual beam optical tweezers system.
Figure 2E:
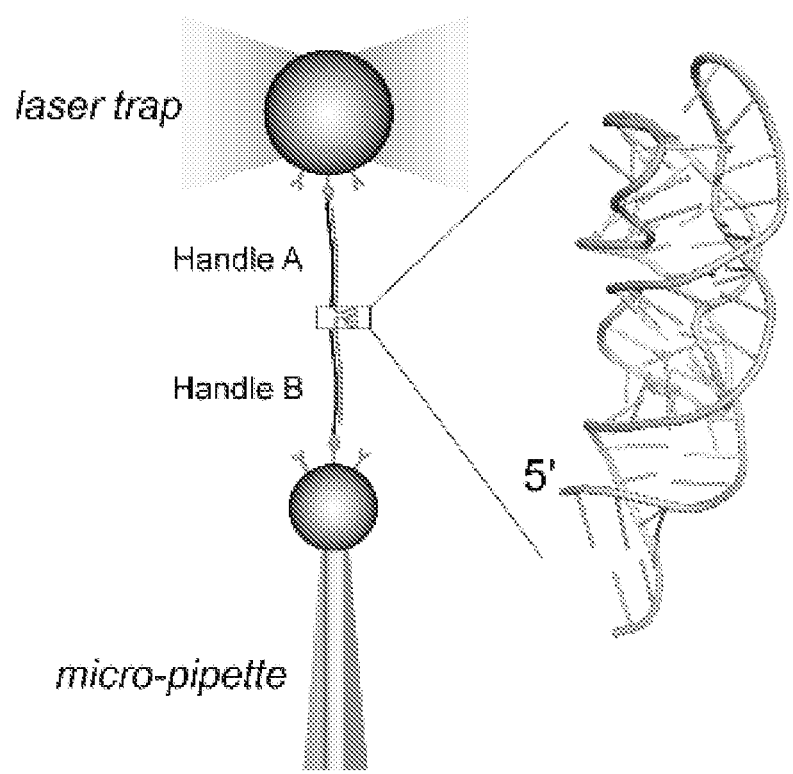
FIG. 2E depicts a single guanine aptamer RNA connected to a bead via handles.

The aptamer domain can be unbound (FIG. 1B). No metabolite or ligand binding to the aptamer domain results in an unstable terminator hairpin structure in the expression platform permitting gene expression.

Purine riboswitches comprise a purine-sensing aptamer domain and an expression platform. Examples of purine riboswitches are guanine riboswitches and adenine riboswitches.

Guanine riboswitches comprise a guanine-sensing aptamer domain and an expression platform. Guanine binding to the aptamer domain results in a stable terminator hairpin structure in the expression platform resulting in terminated gene expression. The aptamer domain can be unbound. No guanine binding to the aptamer domain results in an unstable terminator hairpin structure in the expression domain permitting gene expression.

Adenine riboswitches comprise an adenine-sensing aptamer domain and an expression platform. Adenine binding to the aptamer domain results in a stable terminator hairpin structure in the expression platform resulting in terminated gene expression. The aptamer domain can be unbound. No adenine binding to the aptamer domain results in an unstable terminator hairpin structure in the expression platform permitting gene expression.

Mechanical Assays Reveal Guanine-Induced Receptor Conformation

Figure 3:
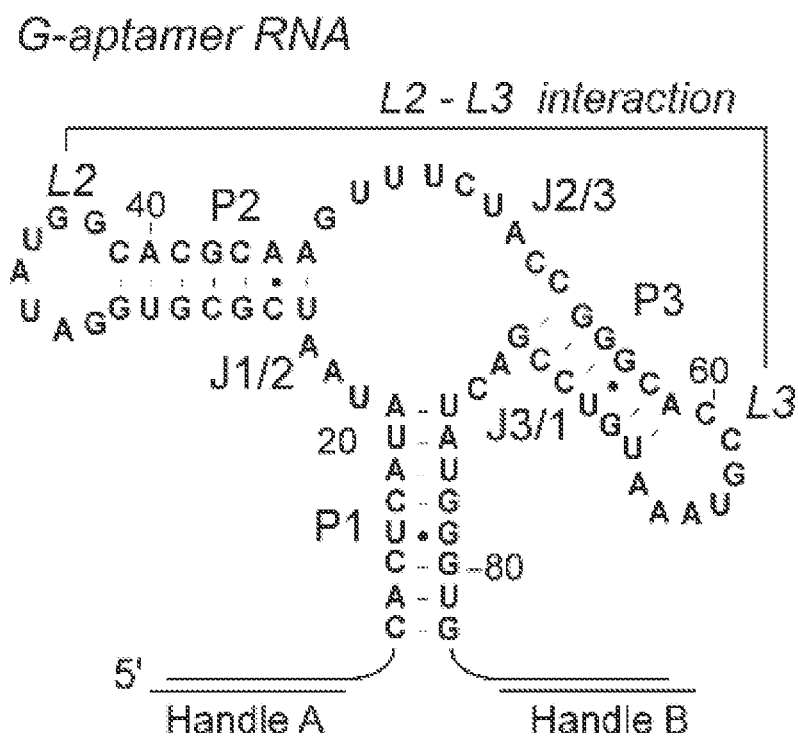
FIG. 3 depicts the sequence (SEQ ID NO: 14) and the secondary structure of the xpt-pbuX guanine-sensing aptamer.
Figure 5A:
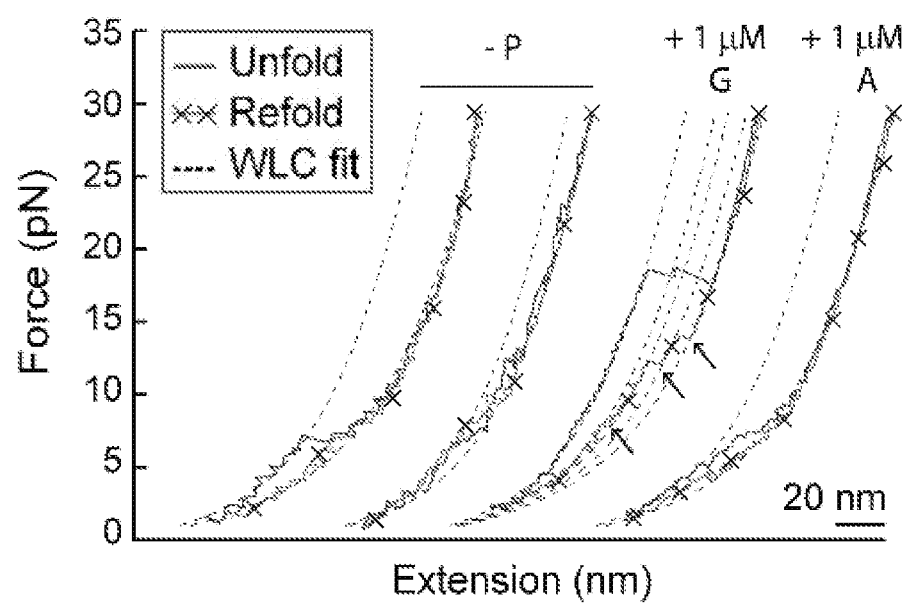
FIG. 5A is a chart showing force-extension curves (FECs) in the absence of any purine (−P), or in the presence of adenine (+1 μM A) or guanine (+1 μM G).
Figure 5B:
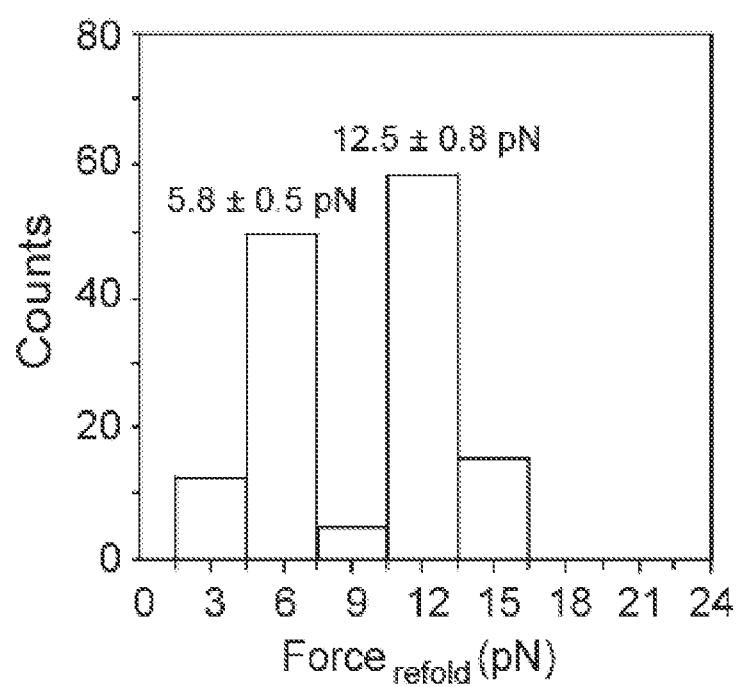
FIG. 5B is a chart showing refolding force ($Force_{refold}$) distribution.
Figure 5C:
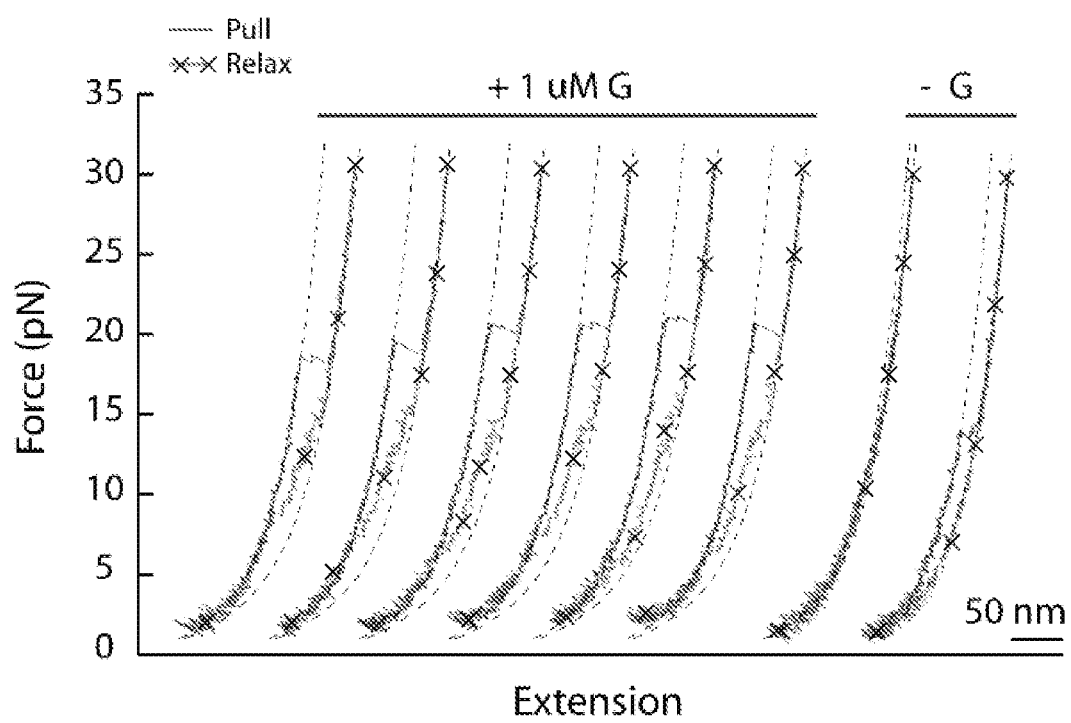
FIG. 5C is a chart showing successive force-extension curves (FECs) in the absence (−G) or presence of guanine (+G).
Figure 5D:
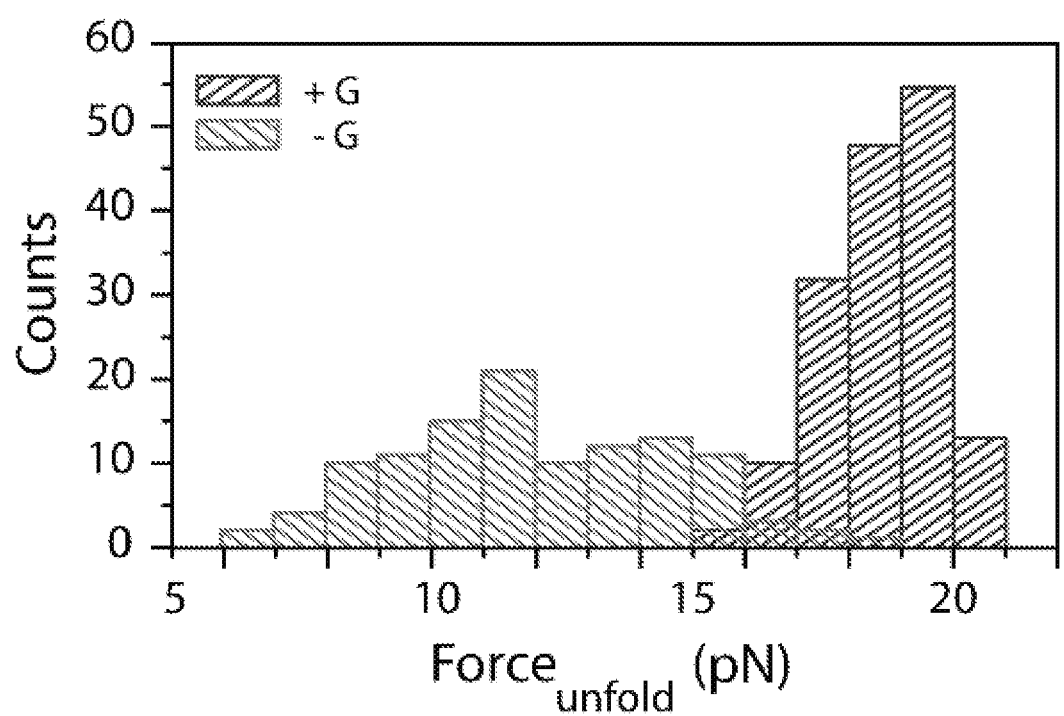
FIG. 5D is a chart showing successive force-extension curves (FECs) in the absence (−G) or presence of guanine (+G).

A 69 nucleotide (nt) guanine-sensing aptamer (FIGS. 3 and 4A-B) from xpt-pbuX operon in *B. subtilis* was used for mechanical unfolding-refolding studies. In the experimental set up shown in FIGS. 2A-E, a single molecule of the guanine-aptamer RNA was clamped between two polystyrene beads through RNA-DNA handles. Figure shows a typical force induced unfolding-refolding trajectories of the aptamer in different conditions. In +1 µM guanine, the aptamer displayed two closely spaced unfolding transitions (blue curve) that often merged to form one transition at 18.6±1.1 pN with a net extension, ΔX=30.2±1 nm (mean±std. error, n=110 traces). Considering the inter-nucleotide distance as 0.448 nm at 18 pN, then using a serial worm-like chain equation $$\left( F = \frac{k_B T}{P} \left[ \frac{1}{4}\left(1 - \frac{X}{L} + \frac{F}{K}\right)^{-2} - \frac{1}{4} + \frac{X}{L} - \frac{F}{K} \right] \right),$$

a complete unfolding of the 69 nt-aptamer will yield an extension of 30.91 nm. The measured extension agrees with the theoretical value within the error range indicating a complete aptamer unfolding (67±2 nts). In the relax cycle, the refolding curve (red in FIG. 5A), displayed hysteresis with transitions near 6 pN and 13 pN (FIG. 5B). The successive unfold/refold trajectories were reproducible indicating that the aptamer folds into one specific conformation in the presence of guanine (FIGS. 5C-D). In the presence of adenine (+1 µM A) or in the absence of any purine (–P), the force-extension curves (FECs) displayed a monotonic elongation or interrupted by short transitions (FIG. 5A) that suggested random structures. Under these conditions, the first pull sometimes showed an extension change of >10 nm. However, the transitions were never reproducible and replaced with smaller transitions with extensions 5 nm in successive cycles, suggesting non-specific structures.

Figure 5E:
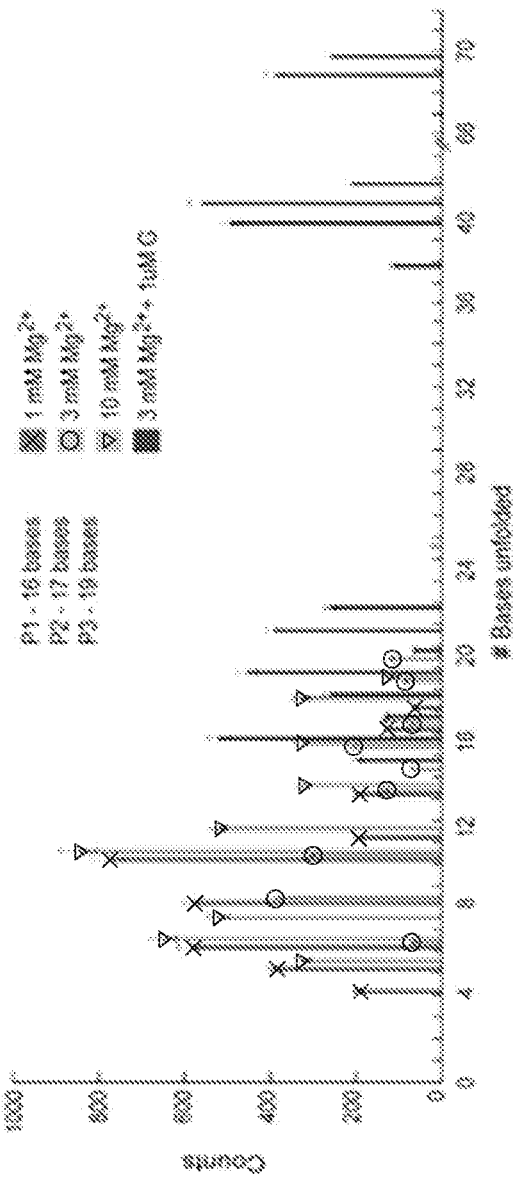
FIG. 5E is a histogram showing the number of bases unfolded in the presence $Mg^{2+}$ salts.

The histogram (FIG. 5E) for the number of unfolding bases indicate small hairpin structures that range from 4-20 nts. It is possible that some of the random stem-loop structures are occasionally similar to P2 and P3, although the expectation was to see a pre-organized P2-P3 helices with a well-defined L2-L3 interaction, as observed in NMR and force-spectroscopy. Theoretically, a pre-organized structure yields an unfolding of ~36 nts (P2-P3), assuming that the junction J2/3 is unoccupied by the ligand. Such a structure is stable enough, to be detected in successive rounds of pull-relax cycles. Instead, a collection of random hairpins was observed. Furthermore, in 10 mM $Mg^{2+}$ salts, the occurrences for 14-20 nt hairpins increased suggesting that $Mg^{2+}$ ions partially stabilize the hairpin structures (FIG. 5E). In high salt conditions, the first pull frequently displayed a trajectory similar to FIG. 5A (–P), which disappeared in the subsequent cycles. Thus, in the mechanical folding assay, a definitive unfolding pattern was not observed whereas the definitive unfolding pattern was observed in successive pull-relax cycles in the absence of ligand (–G), and hence, assigning a unique conformation that would otherwise suggest a stable P2-P3 helix was almost impossible.

Previously, the folding of pbuE adenine riboswitch was studied while attached to the RNA polymerase, wherein pre-organized P2 and P3 helices were observed in the absence of adenine. Enzymes like RNA polymerases require high $Mg^{2+}$ salts and polyamines in the buffer systems to function in-vitro, which may provide favorable conditions for hairpin structures. In this direction, high-resolution NMR studies have reported that the ligand-free state in the adenine-riboswitch can be conformationally heterogeneous, wherein several base pairing interactions indicative of stable helices were missing in the absence of adenine, even though the residues demonstrated sequential connectivities in NOESY spectrum. This supports the findings that $Mg^{2+}$ ions can only confer partial stability to the aptamer RNA in the absence of guanine. As 1 µM guanine was added to low 3 mM $Mg^{2+}$ buffer, the RNA exhibited stable and reproducible structures, which can be related to the P1, P2 and P3 helices (FIG. 5E).

Mechanical assays were also performed in 200 nM guanine concentrations, as shown in FIG. 5E. The RNA exhibited sequential unfolding, wherein the P1 melted first between 5-10 pN. The P2, P3 unfolded between 12-15 pN. The theoretical and the measured extensions agree with each other as indicated in Table 1.

TABLE 1

Equilibrium folding kinetics and energetics for the secondary and the tertiary structures in the wild-type guanine-aptamer and mutants

| RNA/transition | | Force F (pN) | Transition distance ΔX (nm) | Folding rate[a] $k_f$ (s$^{-1}$) | Unfolding rate[a] $k_u$ (s$^{-1}$) | Equilibrium force[b] $F^{eq}$ (pN) | ΔG (0) ($k_B$T)[d] |
|---|---|---|---|---|---|---|---|
| wt | ED | 13 | 7.1 ± 0.4 | 20.0 ± 0.4 | 8.9 ± 0.1 | 13.5 ± 0.03 | −16.7 ± 0.3 |
| 3 mM $Mg^{2+}$ | DC | 13 | 7.9 ± 0.4 | 8.5 ± 0.1 | 32.3 ± 0.5 | 12.2 ± 0.02 | −16.3 ± 0.3 |
| 200 nM G | [e]CB | 13 | 3.5 ± 0.1 | — | 2.6 ± 0.5 | — | −7.2 ± 0.3 |
|  | C'B | 8.5 | 3.4 ± 0.1 | 0.9 ± 0.06 | 0.8 ± 0.05 | 8.7 ± 0.1 | −7.1 ± 0.2 |
|  | BA | 8.5 | 9.9 ± 0.2 | 0.4 ± 0.03 | 0.7 ± 0.09 | 8.2 ± 0.1 | −13.9 ± 0.4 |
| m1 | ED | 13.5 | 7.2 ± 0.2 | 11.8 ± 0.3 | 15.1 ± 0.3 | 13.4 ± 0.01 | −16.6 ± 0.7 |
| 5 mM $Mg^{2+}$ | DC | 12.0 | 7.7 ± 0.3 | 20.7 ± 0.4 | 15.2 ± 0.3 | 12.2 ± 0.01 | −15.9 ± 0.9 |
| 1 uM G | C'A | 6.1 | 12.4 ± 0.3 | 0.6 ± 0.05 | 0.6 ± 0.05 | 6.0 ± 0.03 | −12.4 ± 0.5 |
| m2 | — | — | — | n.d[c] | n.d[c] | n.d[c] | n.d[c] |
| 3 mM $Mg^{2+}$ | — | — | — | n.d | n.d | n.d | n.d |
| 200 nM G | C'A | 6.1 | 12.4 ± 0.4 | 0.53 ± 0.06 | 0.8 ± 0.11 | 6.0 ± 0.03 | −11.9 ± 0.6 |
| m3 | — | — | — | n.d | n.d | n.d | n.d |

TABLE 1-continued

Equilibrium folding kinetics and energetics for the secondary and the tertiary structures in the wild-type guanine-aptamer and mutants

| RNA/transition | | Force F (pN) | Transition distance ΔX (nm) | Folding rate[a] $k_f$ (s$^{-1}$) | Unfolding rate[a] $k_u$ (s$^{-1}$) | Equilibrium force[b] $F^{eq}$ (pN) | ΔG (0) ($k_B$T)[d] |
|---|---|---|---|---|---|---|---|
| 5 mM Mg$^{2+}$ | | — | — | n.d | n.d | n.d | n.d |
| 200 nM G | C'A | 6.1 | 12.5 ± 0.4 | 0.8 ± 0.05 | 0.69 ± 0.05 | 6.1 ± 0.02 | −12.7 ± 0.6 |
| m4 | ED | 13 | 7.2 ± 0.2 | 34.8 ± 1.1 | 8.8 ± 0.2 | 13.9 ± 0.01 | −17.6 ± 0.6 |
| 3 mM Mg$^{2+}$ | DC | 13 | 7.8 ± 0.2 | 16.3 ± 0.3 | 16.5 ± 0.4 | 13.0 ± 0.02 | −17.3 ± 0.6 |
| 200 nM G | C'B | 8.5 | 3.4 ± 0.1 | 0.22 ± 0.02 | 0.56 ± 0.04 | 7.6 ± 0.1 | −6.1 ± 0.2 |
| | BA | 8.5 | 9.5 ± 0.3 | 0.33 ± 0.02 | 1.0 ± 0.1 | 8.0 ± 0.1 | −12.5 ± 0.6 |
| m6 | ED | 13 | 7.1 ± 0.1 | 23.9 ± 0.5 | 7.2 ± 0.2 | 13.8 ± 0.03 | −17.1 ± 0.3 |
| 3 mM Mg$^{2+}$ | DC | 13 | 7.3 ± 0.1 | 1.1 ± 0.03 | 115.4 ± 4.4 | 10.6 ± 0.1 | −11.1 ± 0.3 |
| 200 nM G | C'B | 8.5 | 3.5 ± 0.2 | 7.5 ± 0.2 | 23.9 ± 0.6 | 7.2 ± 0.5 | −6.1 ± 0.4 |
| | BA | 8.5 | 9.8 ± 0.2 | 0.7 ± 0.02 | 1.0 ± 0.1 | 8.3 ± 0.3 | −13.9 ± 0.4 |
| m7 | ED | 13.5 | 7.1 ± 0.3 | 10.0 ± 0.3 | 20.1 ± 0.5 | 13.3 ± 0.05 | −15.8 ± 1.0 |
| 3 mM Mg$^{2+}$ | DC | 12.0 | 7.6 ± 0.2 | 16.6 ± 0.5 | 28.3 ± 1.0 | 11.8 ± 0.05 | −14.8 ± 0.6 |
| 1 uM G | C'B | 8.0 | 3.5 ± 0.2 | 0.9 ± 0.2 | 1.2 ± 0.2 | 8.1 ± 0.4 | −6.5 ± 0.5 |
| | BA | 8.0 | 9.6 ± 0.3 | 0.5 ± 0.08 | 1.7 ± 0.4 | 7.4 ± 0.2 | −11.8 ± 0.6 |
| m8 | ED | 13.5 | 7.0 ± 0.2 | 10.5 ± 0.4 | 13.2 ± 0.5 | 13.5 ± 0.03 | −16.0 ± 0.7 |
| 3 mM Mg$^{2+}$ | DC | 12.0 | 7.7 ± 0.2 | 15.9 ± 0.4 | 17.5 ± 0.5 | 11.8 ± 0.1 | −15.5 ± 0.6 |
| 200 nM G | C'B | 8.5 | 3.6 ± 0.2 | 1.4 ± 0.2 | 1.5 ± 0.2 | 8.4 ± 0.3 | −7.4 ± 0.5 |
| | BA | 8.5 | 9.5 ± 0.3 | 0.4 ± 0.05 | 0.2 ± 0.05 | 8.8 ± 0.2 | −14.3 ± 0.7 |
| wt | ED | 13.5 | 7.0 ± 0.2 | 14.7 ± 0.4 | 13.4 ± 0.4 | 13.6 ± 0.02 | −16.3 ± 0.7 |
| 3 mM Mg$^{2+}$ | DC | 12.0 | 7.5 ± 0.3 | 22.0 ± 0.6 | 14.3 ± 0.4 | 12.3 ± 0.02 | −15.5 ± 0.9 |
| 250 uM DAP | C'B | 8.5 | 3.6 ± 0.2 | 0.96 ± 0.08 | 0.8 ± 0.06 | 8.7 ± 0.2 | −7.6 ± 0.4 |
| | BA | 8.5 | 9.7 ± 0.2 | 0.29 ± 0.02 | 0.023 ± 0.004 | 9.8 ± 0.1 | −16.6 ± 0.5 |

[a]Folding and unfolding kinetics were recorded by holding the RNA at the preset force for >90 secs. The force was varied between 16.0-5.0 pN.
[b]Near equilibrium, the forward ($k_f$) and the reverse ($k_u$) rates are almost equal (FIGS. 12A-H).
[c]n.d stands for not-defined.
[d]ΔG(0) is the free energy change in the absence of any force, determined by the relation (23), ΔG(0) = ΔG(F) − FΔX + ΔG$_{stretch}$ where, ΔG(F) = −$k_B$Tln($k_f/k_u$) and ΔX is the net extension at F. The work done to stretch the RNA to its single-strandedness is given as, ΔG$_{stretch}$ = $\int_0^{x_{ss}}$ Fdx$_{ss}$ using the WLC model where T = 298 K, P = 1 nm, L = 0.59 nm/base and K = 1600 pN.
[e]CB did not show frequent hopping at 13 pN, thus only $k_u$ is defined. The free energy change is then given as, ΔG(0) = −F · ΔX + ΔG$_{stretch}$.

Data is represented as mean±std. error from 91 traces (wild-type in guanine buffer), 74 traces (m1), 20 traces (m2), 23 traces (m3), 67 traces (m4), 87 traces (m6), 32 traces (m7), 40 traces (m8) and 47 traces for wild-type in DAP. Guanine, DAP and Mg$^{2+}$ concentrations are indicated. The buffer contained 10 mM Tris pH 7.5, 250 mM NaCl. Since m7 and m8 data were collected at a different time, the RNA showed a force offset of ~0.5 pN, which was corrected in the analysis. The transitions ED, DC, CB, C'B and BA indicates the folding of P2, P3, J2/3, L2-L3 and P1 respectively. The transition distances shown here are without any adjustment of the helix width. In CF assays, a 2 nm helix width can be subtracted at the end of P1-folding, as described in Table 1.

Figure 5G:
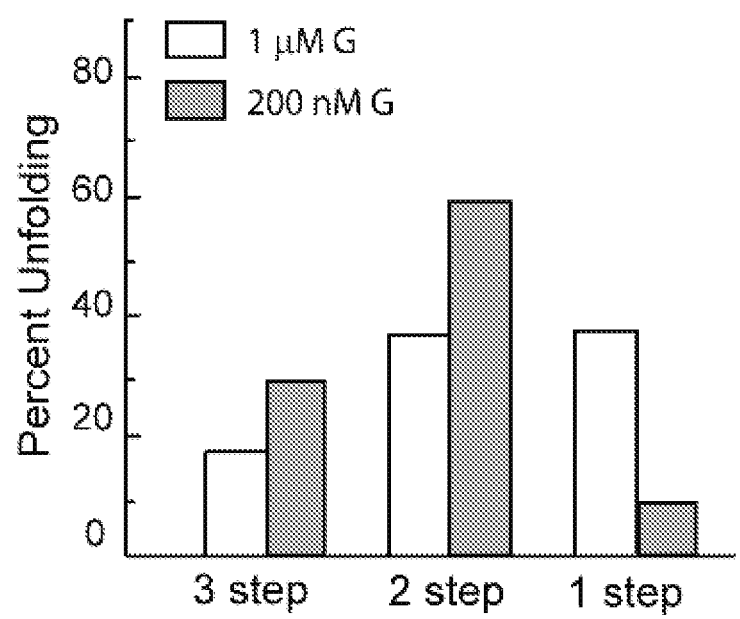
FIG. 5G is a chart showing the percentage unfolding observed in high and low guanine.
Figure 6A:
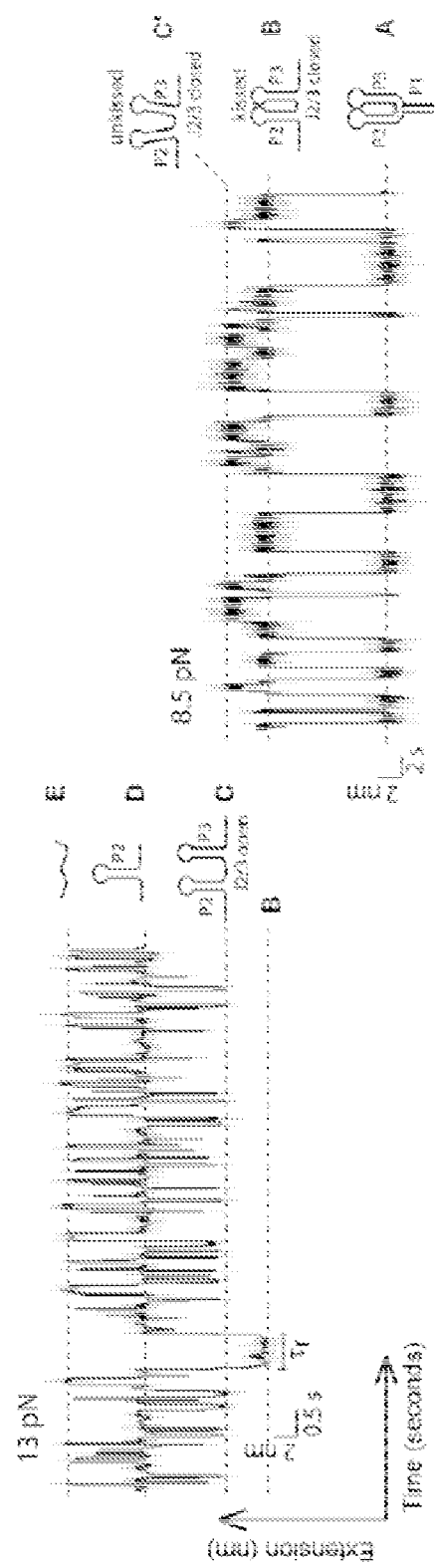
FIG. 6A shows the extension vs. time trace at 13 pN and 8.5 pN.

The above mechanical unfolding assay was performed at a pulling rate of 200 nm/s that resulted in almost similar extensions for P2 and P3. The unfolding order for P2, P3 was unclear. This was resolved in the constant-force experiment (FIG. 6A). A comparison of the force-extension curves (FECs) under high (1 μM) and low (200 nM) guanine salts indicated that the aptamer frequently unfolds cooperatively in the former, whereas discrete 3-step unfolding is observed in the low guanine condition (FIG. 5G). Mechanical assays performed in 100 nM and 50 nM guanine buffer displayed mostly unbound conformations. Therefore, all single-molecule folding experiments were performed in 3 mM Mg$^{2+}$ buffer containing 200 nM guanine, unless mentioned otherwise.

Guanine Induces a Conformational Switching in the Junction J2/3

Figure 7A:
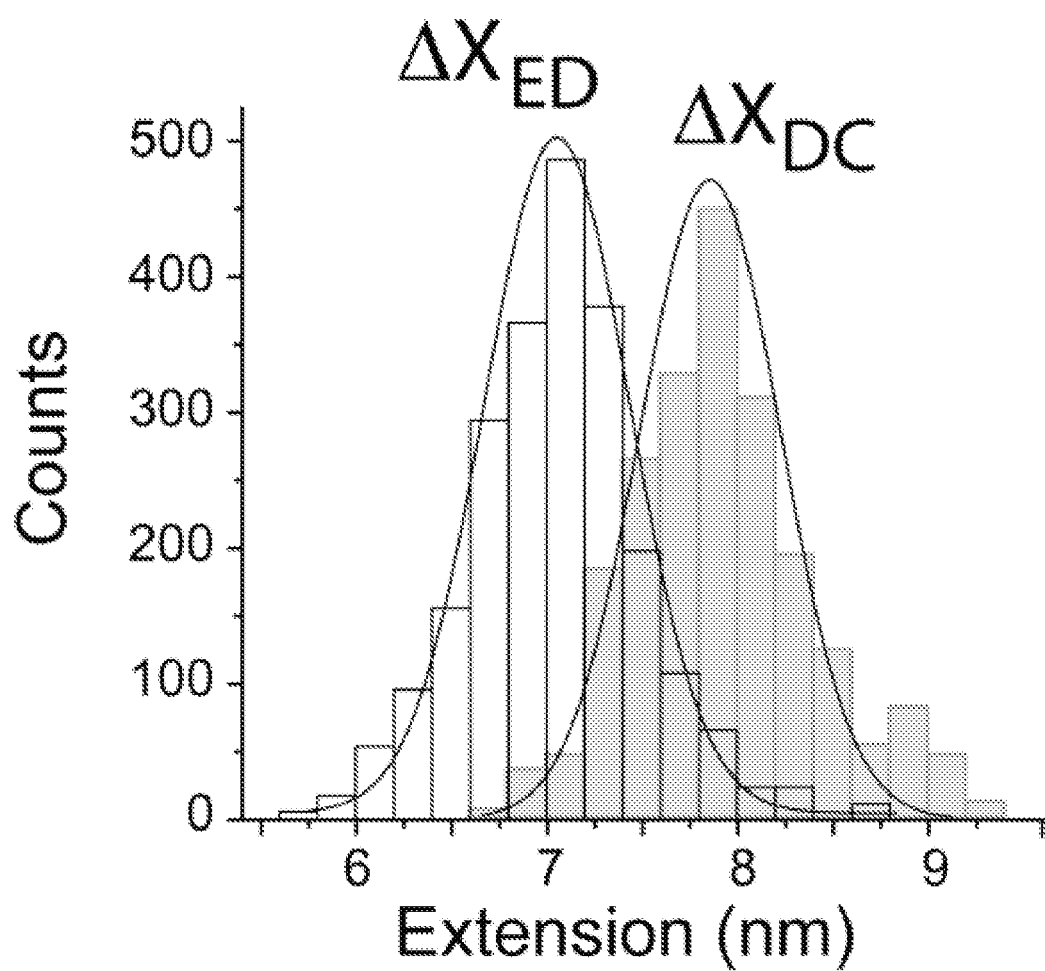
FIG. 7A is a distance histogram for constant force measurements at 8.5 pN.
Figure 7B:
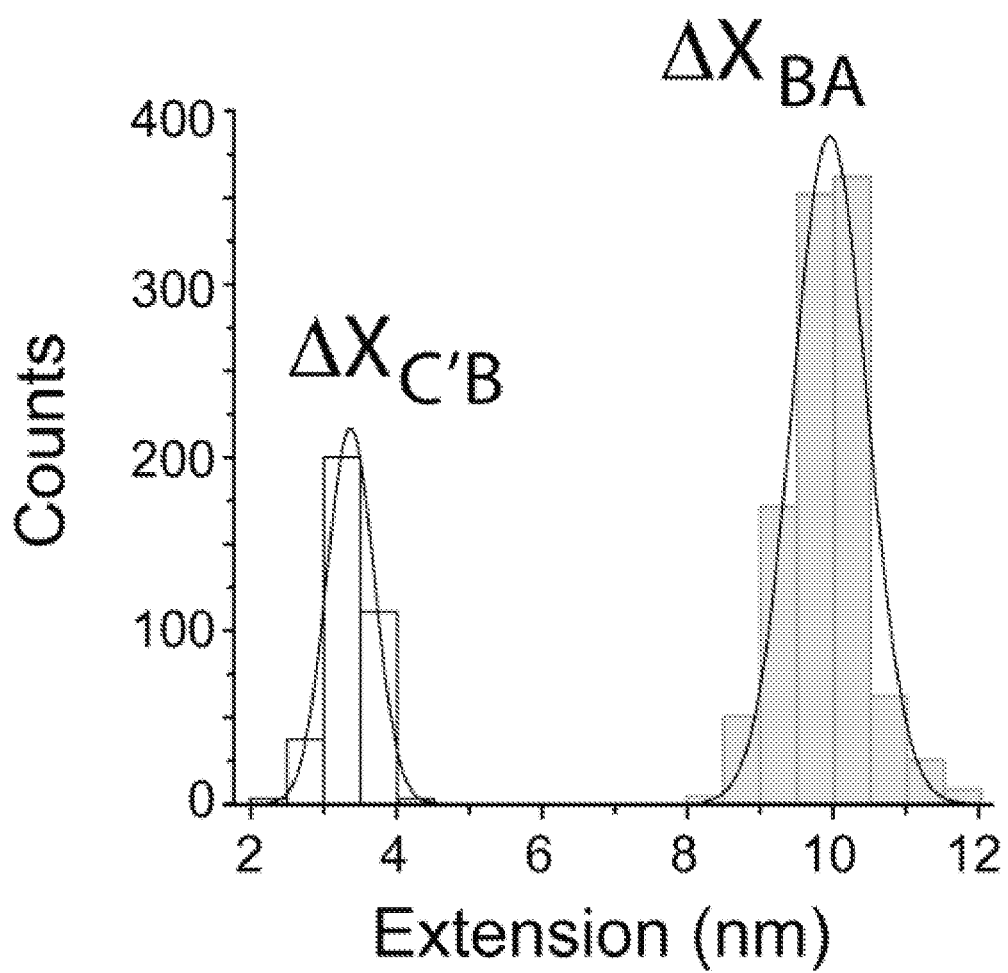
FIG. 7B is a distance histogram for constant force measurements at 13 pN.

The aptamer folding was monitored in real time using a constant-force (CF) assay. Equilibrium sampling techniques provide unprecedented insights into the rare events in the course of folding that are otherwise difficult to identify. The technique also allows for determination of the kinetic rates that has not been fully investigated in the guanine riboswitch. The relative dynamics of the helices have been investigated in ensemble and smFRET experiments, which indicated a non-dynamic P1-P3, upon which the P2 helix switches conformations. As shown in FIG. 6A (left panel), the RNA oscillated between the linear and the hairpin conformations (E↔D↔C) at 13 pN. The distances ΔX$_{ED}$=7.1±0.4 nm and ΔX$_{DC}$=7.9±0.4 nm correspond to the folding of a 17±1 nt (P2) and 19±1 nt (P3) respectively (FIGS. 7A-B). The conversion of distances to nucleotides in CF assay are described in Table 2.

TABLE 2

| Folding element/ Transition | Nucleotides (nt) | Force (pN) | Theoretical ΔX (nm) | Observed ΔX$_{obs}$ (nm) | Observed nucleotides | n (number of traces) |
|---|---|---|---|---|---|---|
| Complete aptamer | 69 | 18 | 30.91 | 30.2 ± 1.0 (Force-ramp) | 67.1 ± 2 | 110 |
| P2 hairpin (ED) | 17 | 13 | 7.09 | 7.1 ± 0.4 (CF) | 17.0 ± 1 | 91 |
| P3 hairpin (DC) | 19 | 13 | 7.92 | 7.9 ± 0.4 (CF) | 18.9 ± 1 | 91 |

TABLE 2-continued

| Folding element/ Transition | Nucleotides (nt) | Force (pN) | Theoretical ΔX (nm) | Observed ΔX$_{obs}$ (nm) | Observed nucleotides | n (number of traces) |
|---|---|---|---|---|---|---|
| J2/3 (CB) | 8 | 13 | 4.17 | 3.5 ± 0.1 (CF) | 8.4 ± 0.2 | 91 |
| L2-L3 (C'B) | — | 8.5 | — | 3.4 ± 0.1 (CF) | — | 91 |
| P1+ junctions (BA) | 25 | 8.5 | 8.49 | 8.0 ± 0.2 (CF) | 21.7 ± 0.5 | 91 |

Figure 6B:
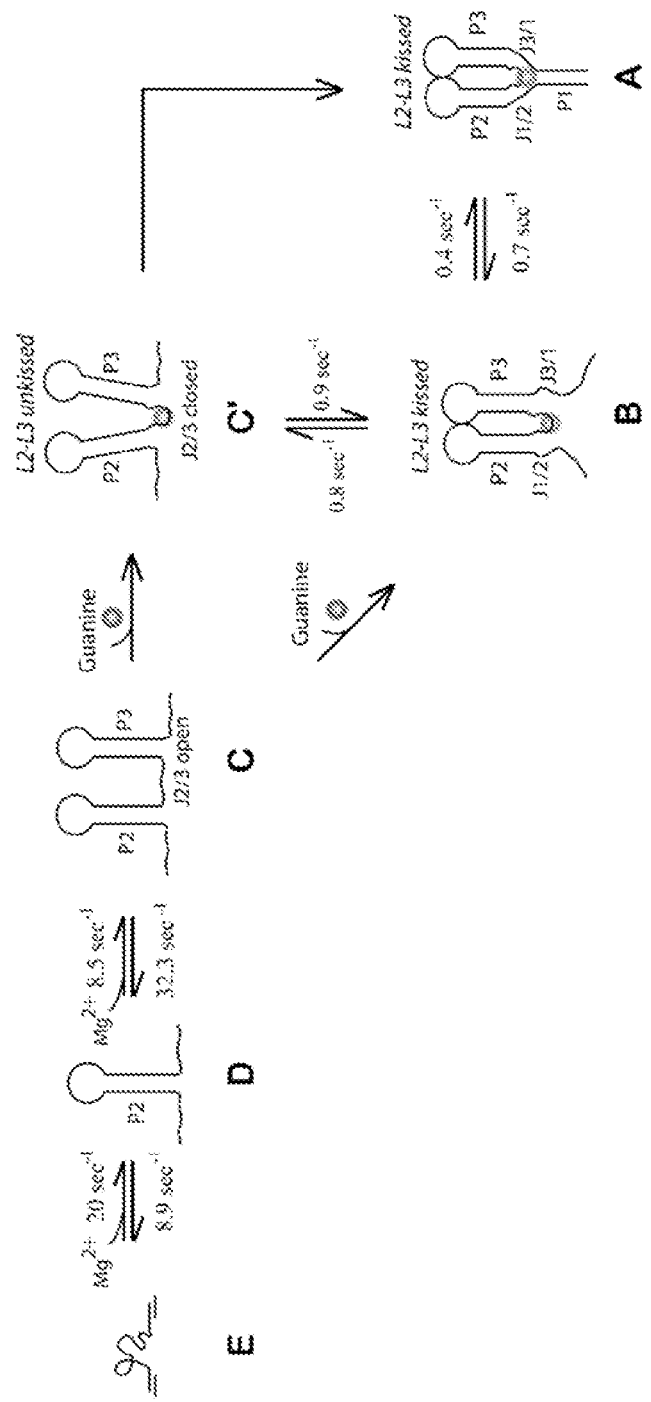
FIG. 6B depicts the aptamer folding pathway and the kinetics.

The data suggests that the P2 folds first followed by the P3 hairpin. A similar folding sequence has been reported for the adenine-riboswitch. In general, the $F^{eq}$~13 pN for P2-P3 in guanine-aptamer is higher than the related adenine-aptamer ($F^{eq}$~7-10 pN). This can be attributed to the higher GC content of the helices in the guanine-aptamer (42-47% in G-vs. 29-32% in adenine-aptamer). A comparison between the kinetic rates measured for P2, P3 at $F^{eq}$ in the guanine- and the adenine-aptamer is indicated in Table 3.

is twice ($k_{kiss}$=0.9±0.06s$^{-1}$) as fast as P1($k_{p1}$=0.4±0.03s$^{-1}$). The slow rate for the latter may be due to the closing of the J1/2 and the J3/1 around guanine that precedes the folding of P1. The folding scheme in the formation of the guanine-bound receptor and its associated kinetics are shown in FIG. 6B. It can be evident that the P1 stem folds last, at a lower force near 8 pN in both the guanine- and adenine-ribo-switches (Table 3).

TABLE 3

| Folding Structure/ transition | $F^{eq}$ (pN) | $k^{eq}$ (s$^{-1}$) | Nucleotides | GC % | Hairpin loop size |
|---|---|---|---|---|---|
| This work (xpt G-Aptamer); [G] = 200 nM | | | | | |
| P2 (ED) | 13.49 ± 0.03 | 13.20 ± 0.20 | 17 (AC bulge at the base shortens the helix length from 21 to 17) | 47 | 7 |
| P3 (DC) | 12.19 ± 0.02 | 16.80 ± 0.30 | 19 | 42 | 7 |
| Closed J2/3 (CB) | ~13 pN | — | 8 | — | — |
| L2-L3 (C'B) | 8.72 ± 0.11 | 0.82 ± 0.06 | — | — | — |
| P1 (BA) | 8.21 ± 0.11 | 0.55 ± 0.09 | 25 | 24 | — |
| pbuE A-Aptamer; [A] = 200 μm | | | | | |
| P2 | 10.0 ± 0.8 | 18.17 ± 5.45 | 21 | 29 | 9 |
| P3 | 7.0 ± 0.6 | 60.34 ± 18.10 | 19 | 32 | 9 |
| A-competent complex | 5.1 ± 0.5 | 90.02 ± 54.01 | 8 | — | — |
| P1 | 9.0 ± 1.0 | 1.00 ± 1.00 | 15 | 13 | — |

In the folding assays, CHB hopping was observed at 13 pN (left, FIG. 6A). The $\Delta X_{CB}$~3.5 nm corresponded to the folding of the 8-nt J2/3 that closes upon binding guanine. As the force was lowered to 8.5 pN, the C'↔B and B↔A hops were observed (right, FIG. 6A). The C'↔B fluctuations are due to the long-range L2-L3 tertiary interactions that represent the unkissed↔kissed conformations. As J2/3 closes by binding the ligand, it also places the end loops L2 and L3 juxtaposed to each other, which facilitates the long-range kissing interaction. In other words, while guanine-binding causes the closing of the 8-nt junction, the effect is observed in the formation of the kissed L2-L3 interactions. Both the junction J2/3 and the L2-L3 exhibited an identical change in extension, ΔX~3.5 nm, although the former responded at a higher force than the latter (also see Table 2).

Recent molecular simulation studies have indicated that the junction J2/3 becomes solvent exposed when extended by an average distance of 34 Å in adenine riboswitch. The results thus support our single-molecule data, which shows that the J2/3 undergoes a structural rearrangement of 3.5±0.1 nm from an open to a close state near 13 pN. The tertiary L2-L3 interactions hop near 8 pN with a similar distance. Subsequently, a kissed L2-L3 triggers the folding of the P1-stem, which is observed as the BA transition (right, FIG. 6A). From n=91 traces analyzed, the folding rate of L2-L3

Figure 4A:
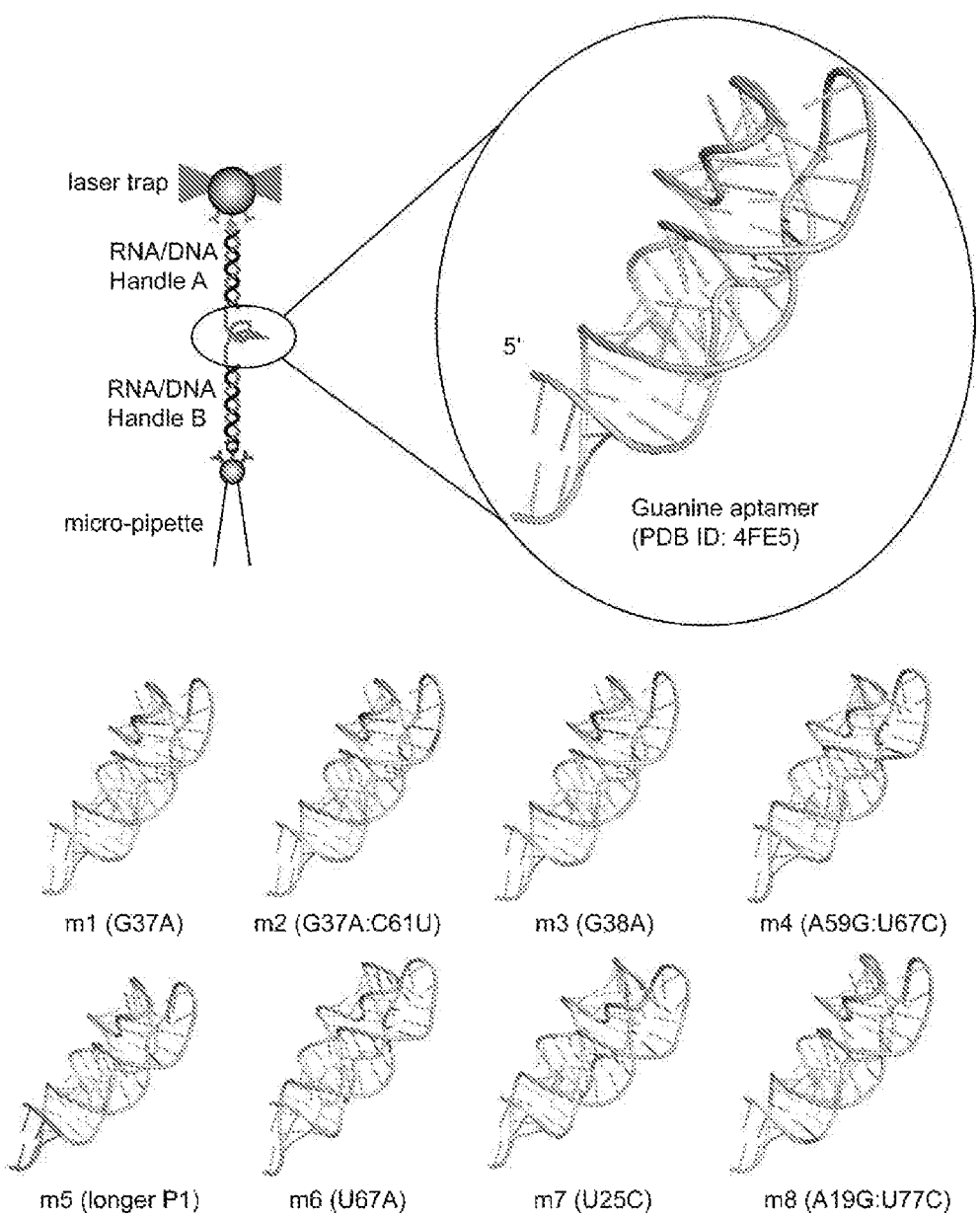
FIG. 4A depicts the three-dimensional structure for the wild-type guanine aptamer and guanine aptamer mutants m1-m8.
Figure 4B:
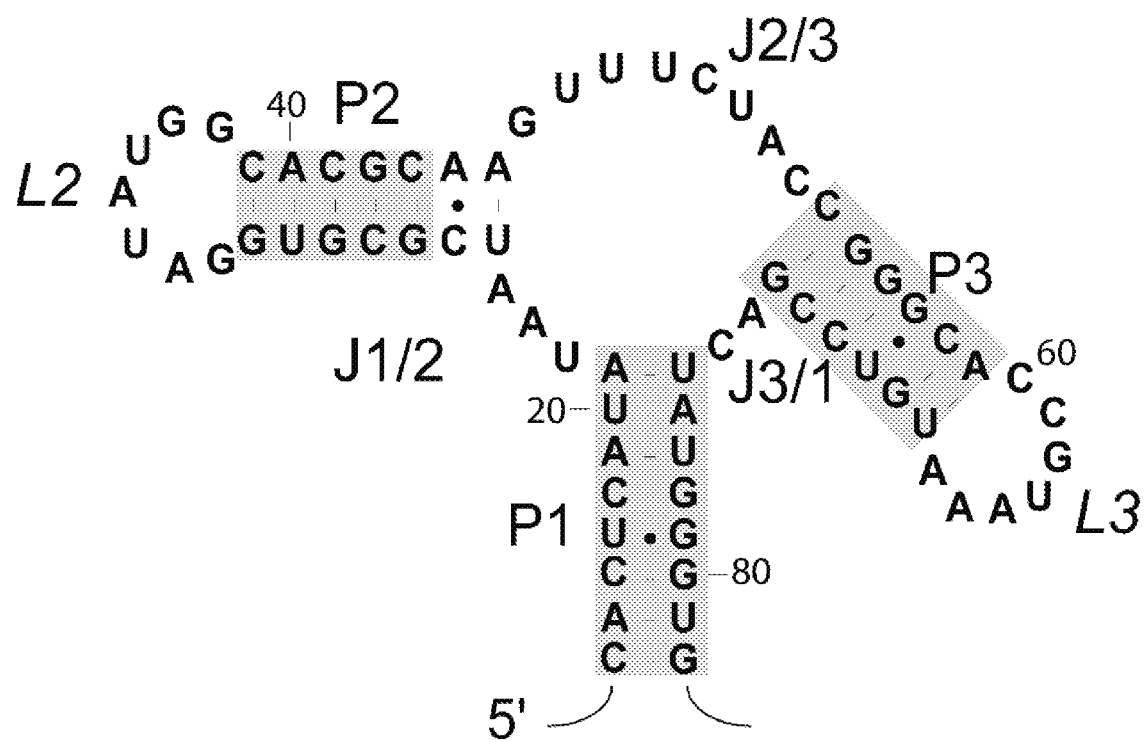
FIG. 4B depicts the nucleotide sequence (SEQ ID NO: 15) for the wild-type guanine aptamer and each of the structural components of the wild-type guanine aptamer.
Figure 4C:
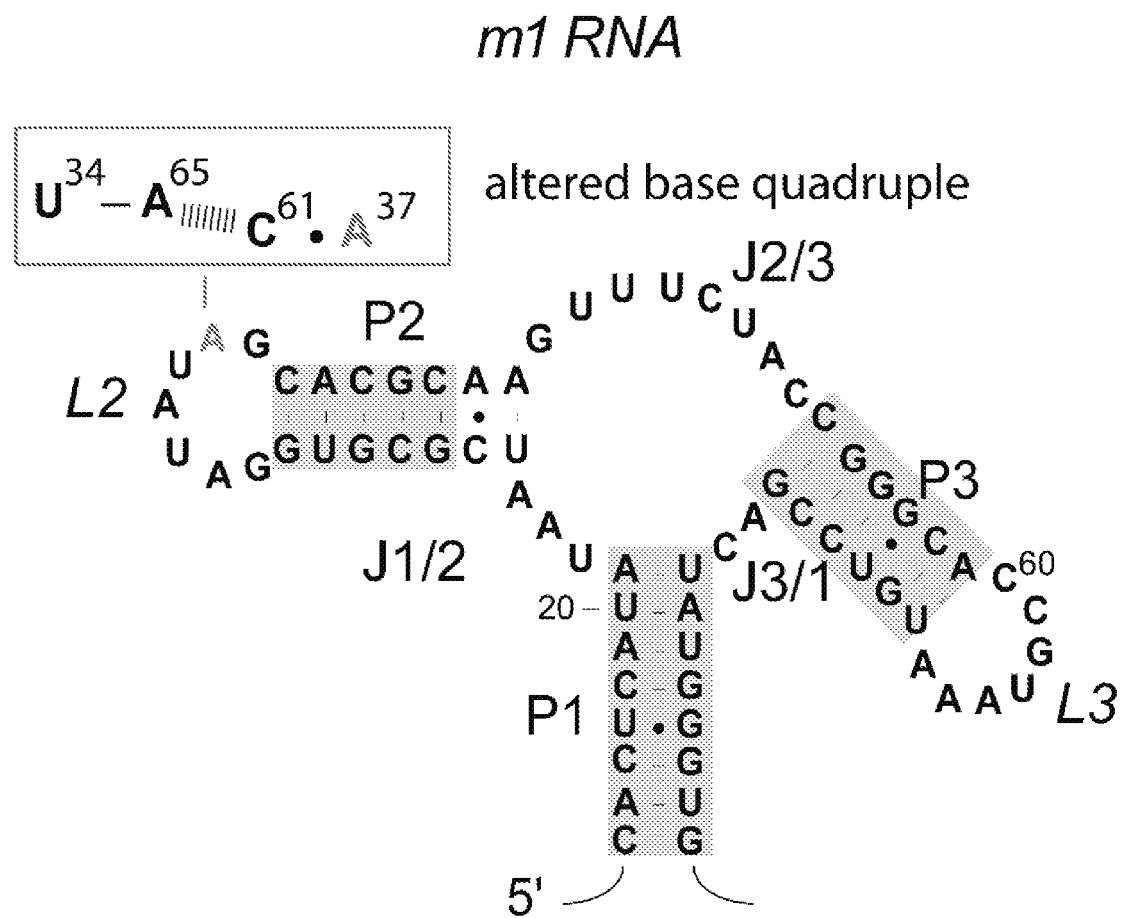
FIG. 4C depicts the nucleotide sequence (SEQ ID NO: 16) for the m1 mutant guanine aptamer and each of the structural components of the m1 mutant guanine aptamer.
Figure 4D:
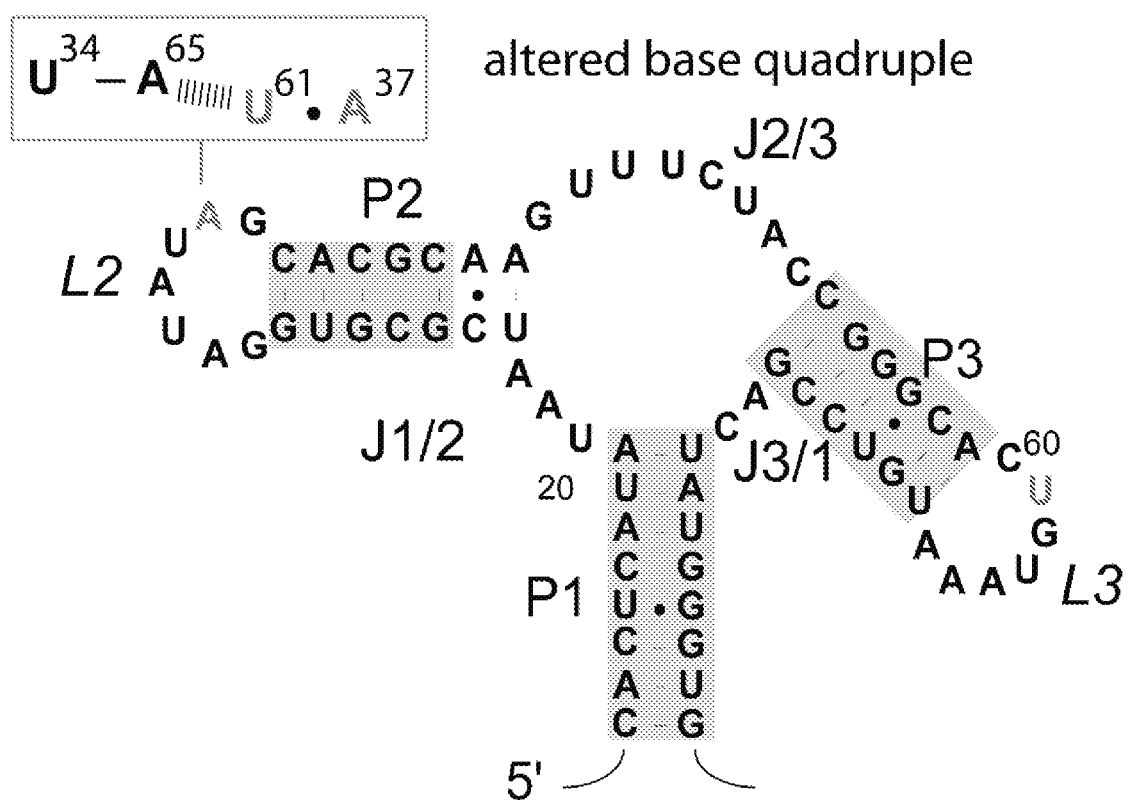
FIG. 4D depicts the nucleotide sequence (SEQ ID NO: 17) for the m2 mutant guanine aptamer and each of the structural components of the m2 mutant guanine aptamer.
Figure 4E:
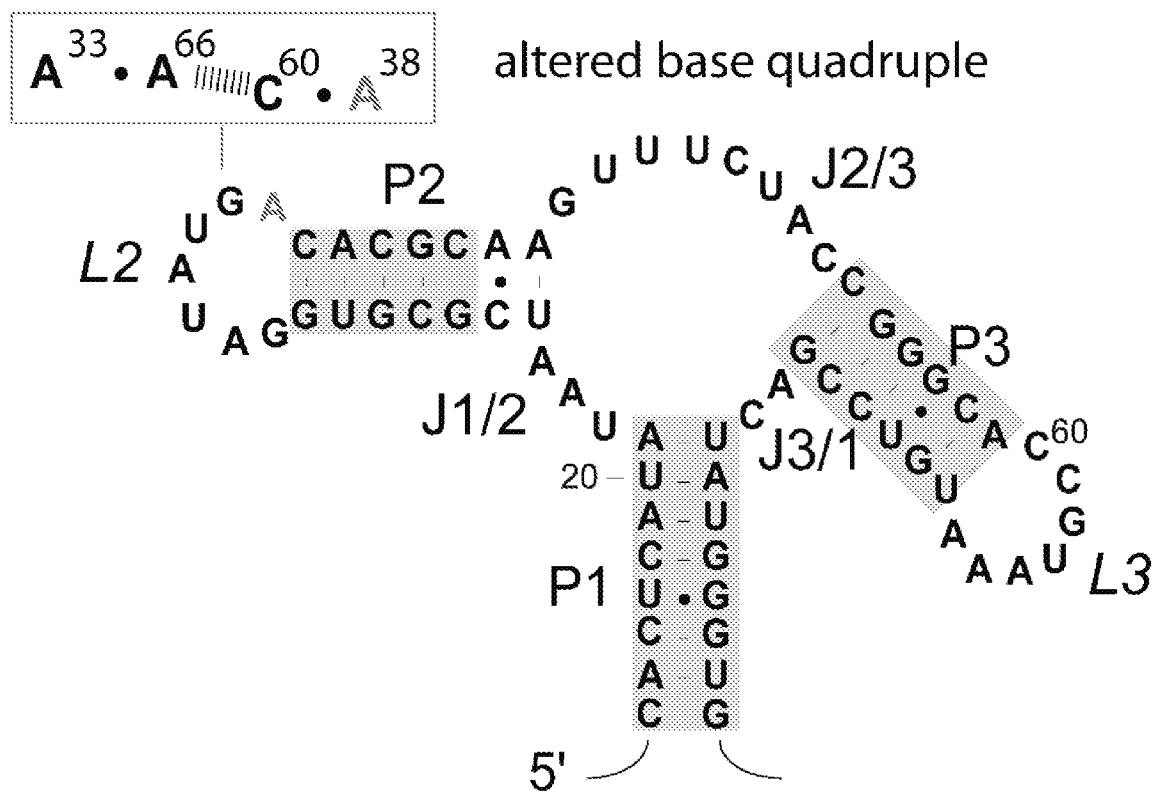
FIG. 4E depicts the nucleotide sequence (SEQ ID NO: 18) for the m3 mutant guanine aptamer and each of the structural components of the m3 mutant guanine aptamer.
Figure 8A:
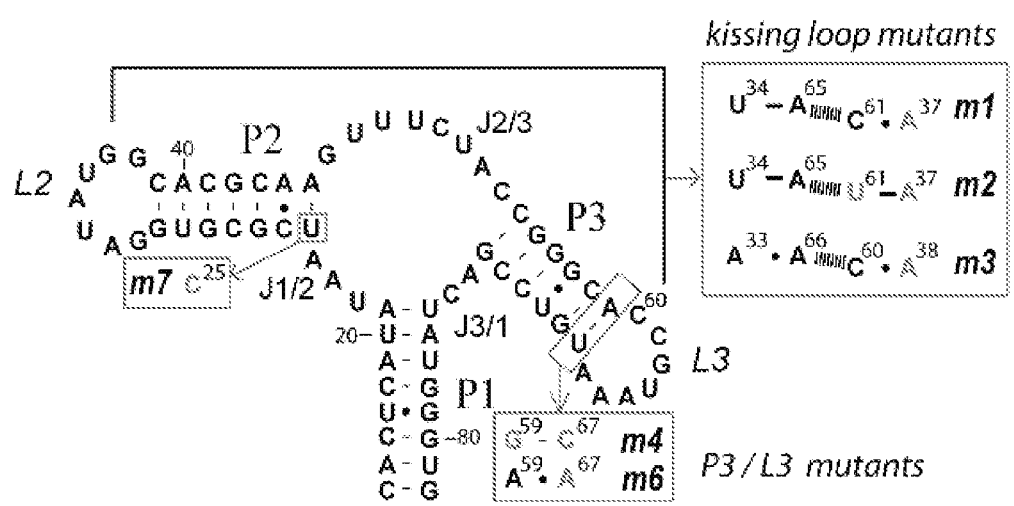
FIG. 8A depicts the sequence (SEQ ID NO: 24) and the secondary structure of kissing loop mutations designed to alter the L2-L3 interactions directly in m1, m2 and m3, or indirectly in m4 and m6.

The Dynamics of the Tertiary Interaction Affects the Stability of the Binding Core To assess the proposed folding pathway in FIGS. 6A-B, mutations were designed in the guanine-aptamer. According to the X-ray and NMR structures, the end loops L2 and L3 interact via base quadruples U$^{34}$•A$^{65}$•C$^{61}$–G$^{37}$ and A$^{33}$•A$^{66}$•C$^{60}$–G$^{38}$. One of the base tetrads were partially disrupted in m1 and m3 by introducing G37A and G38A mismatches respectively (FIGS. 8A, 4C, and 4E). In m2, G37A/C61U changes were made that has been previously characterized in NMR study (FIGS. 8A and 4D).

Figure 4F:
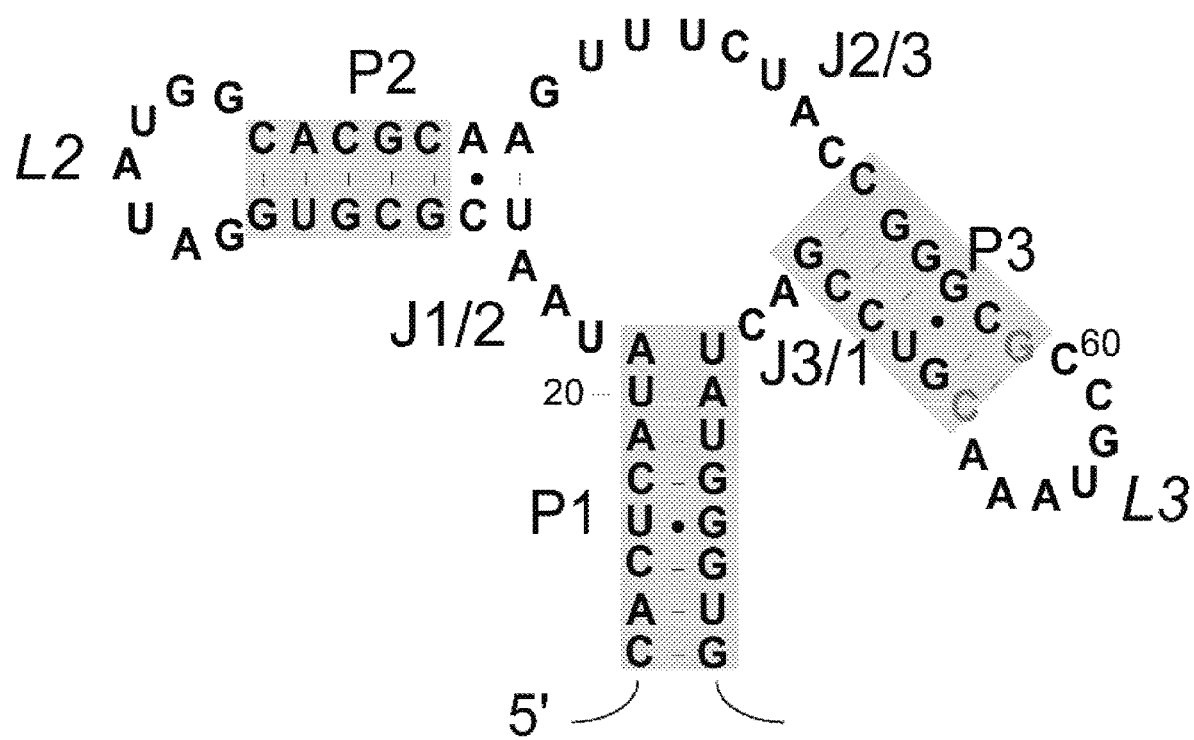
FIG. 4F depicts the nucleotide sequence (SEQ ID NO: 19) for the m4 mutant guanine aptamer and each of the structural components of the m4 mutant guanine aptamer.

To investigate the effect of conformational flexibilities at the stem-loop junction on L2-L3 dynamics, m4 and m6 mutations were designed targeting the helix-loop (P3/L3) interface. Thus, in m4 (A59G/U67C), a stable GC bp replaced the AU closing pair, while in m6 the U67A replacement created the AA mismatch, rendering the loop 3 bigger and flexible (FIGS. 4F and 4H).

Figure 4G:
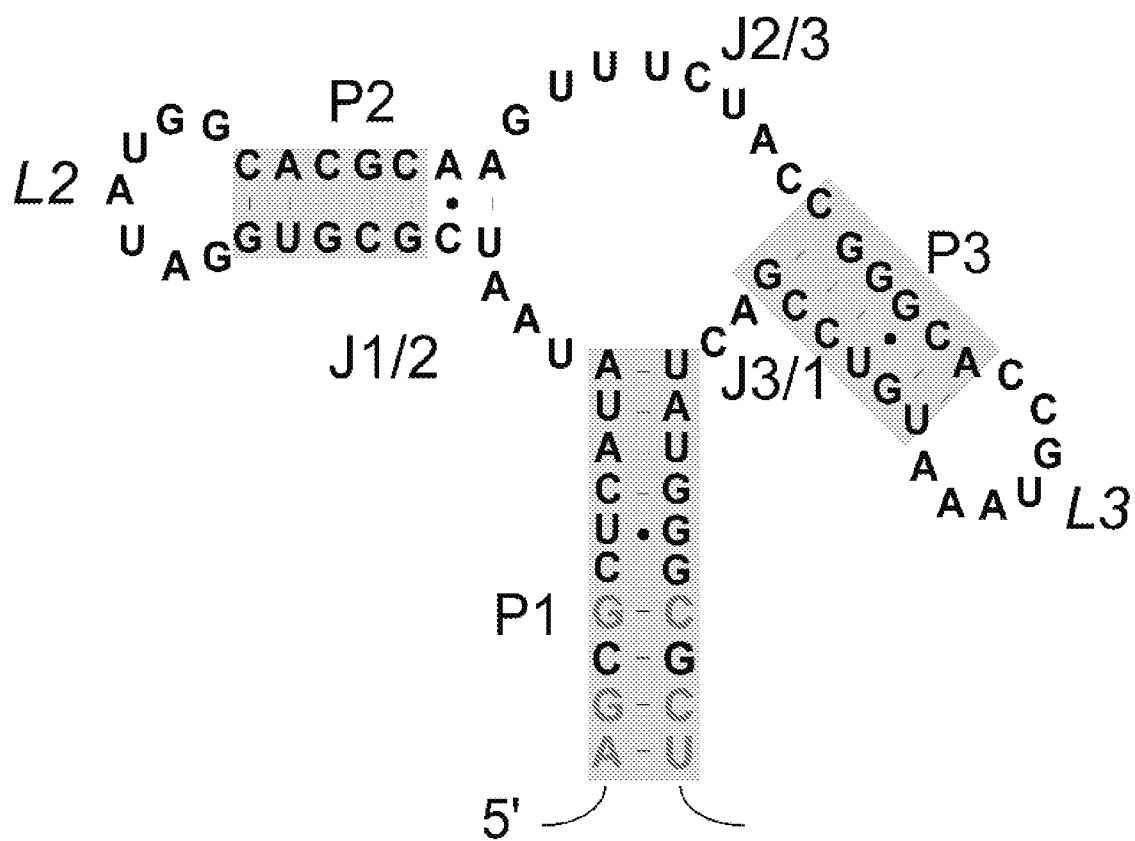
FIG. 4G depicts the nucleotide sequence (SEQ ID NO: 20) for the m5 mutant guanine aptamer and each of the structural components of the m5 mutant guanine aptamer.
Figure 4H:
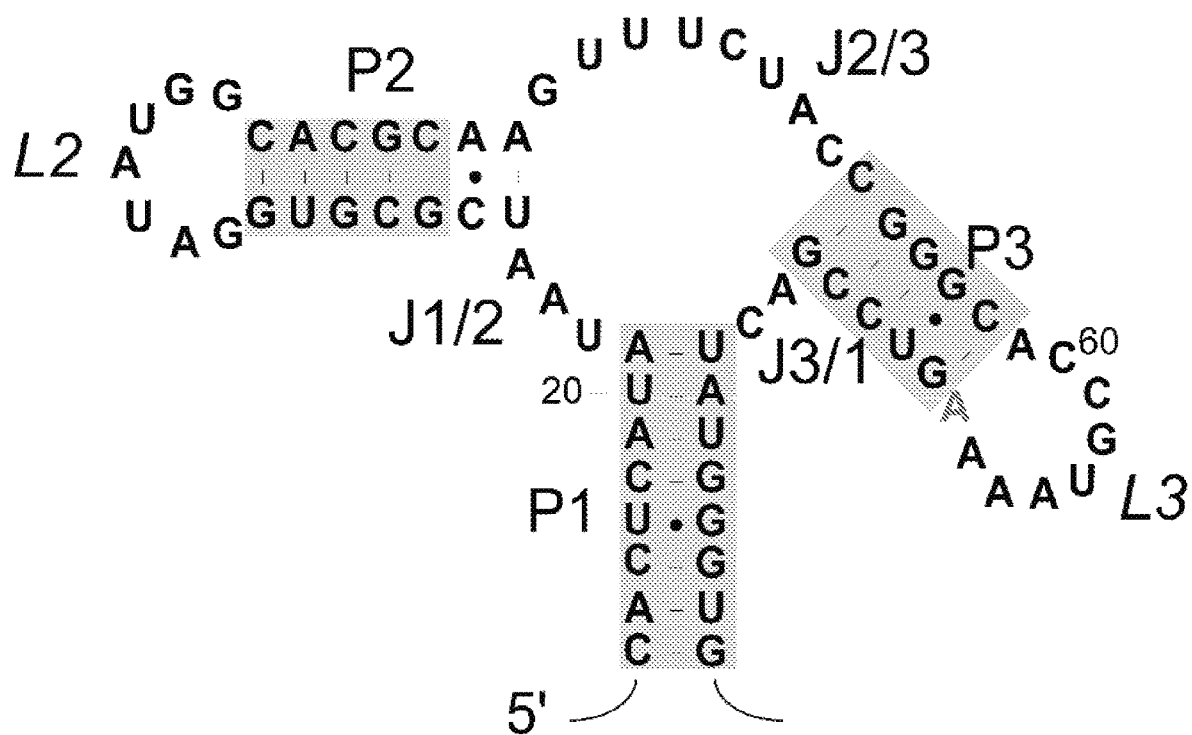
FIG. 4H depicts the nucleotide sequence (SEQ ID NO: 21) for the m6 mutant guanine aptamer and each of the structural components of the m6 mutant guanine aptamer.
Figure 4I:
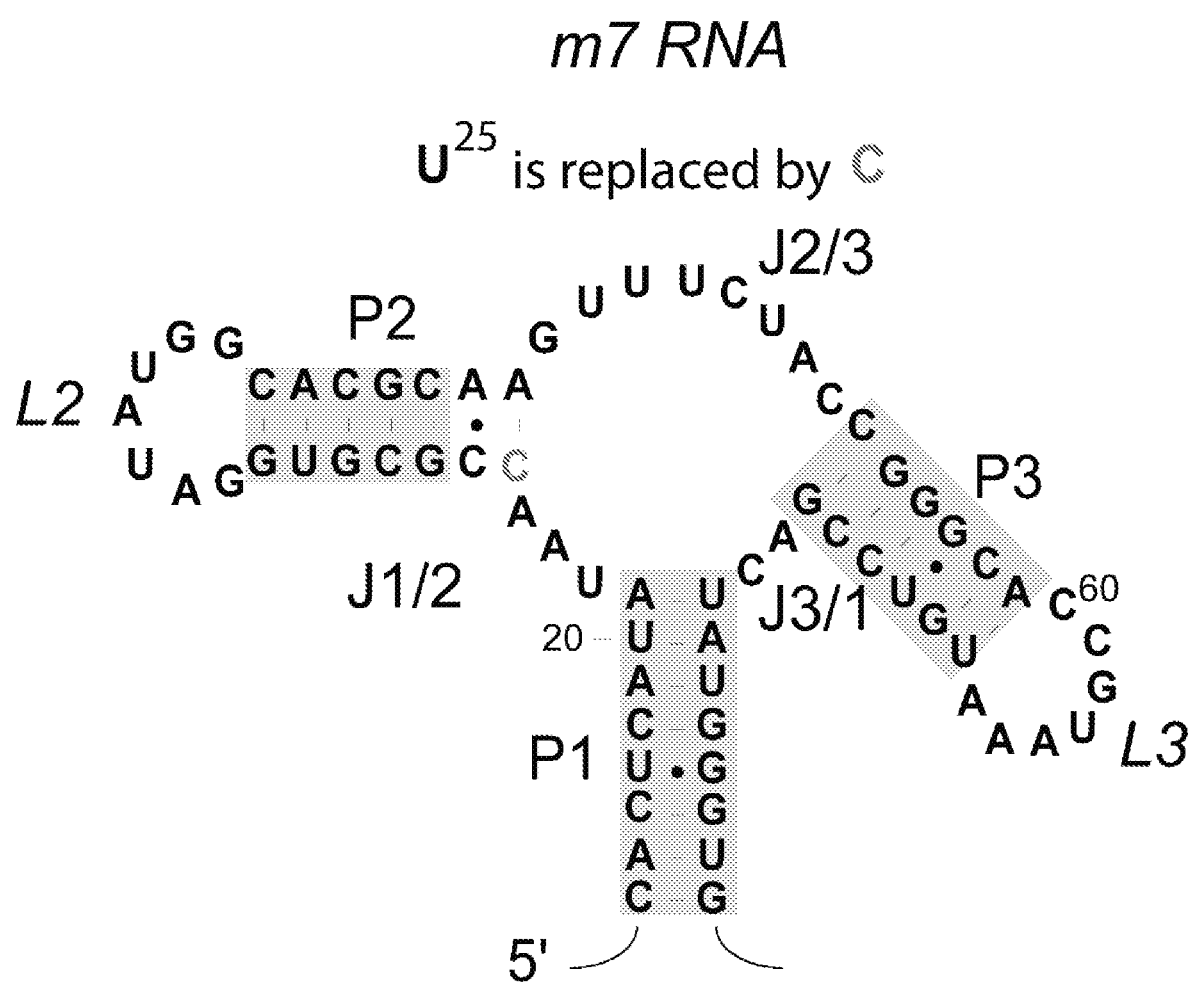
FIG. 4I depicts the nucleotide sequence (SEQ ID NO: 22) for the m7 mutant guanine aptamer and each of the structural components of the m7 mutant guanine aptamer.

In m7, the U25C replacement rendered the junctions J2/3 and J1/2 more flexible (FIG. 4I). Additional P1 mutations (m5 and m8) were also designed as shown in FIGS. 9A-B, 4G, and 4J. For a complete perspective of the altered nucleobases on the overall guanine-aptamer architecture, refer to FIGS. 4A-B.

Figure 5F:
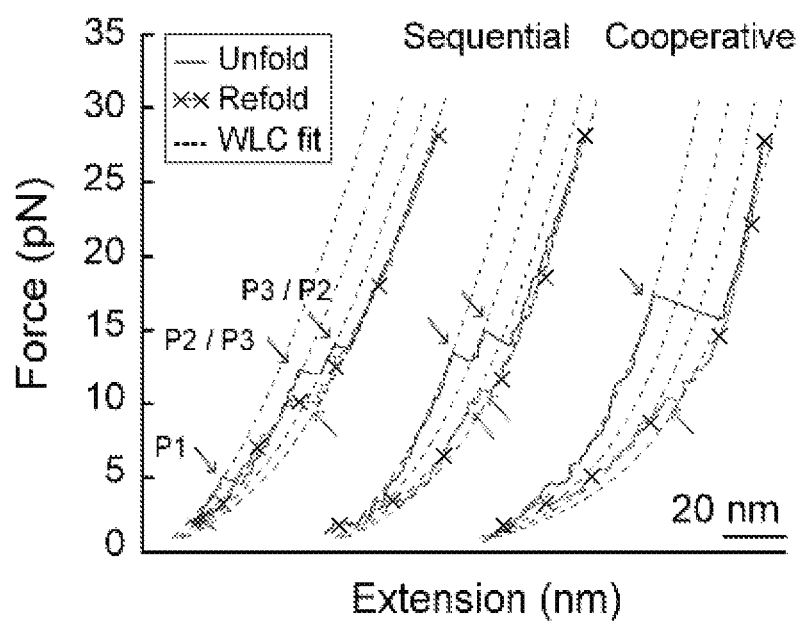
FIG. 5F is a chart showing an aptamer unfold in 3-steps due to the sequential rupture of P1-P2-P3, or cooperatively in 2- or 1-step.
Figure 8B:
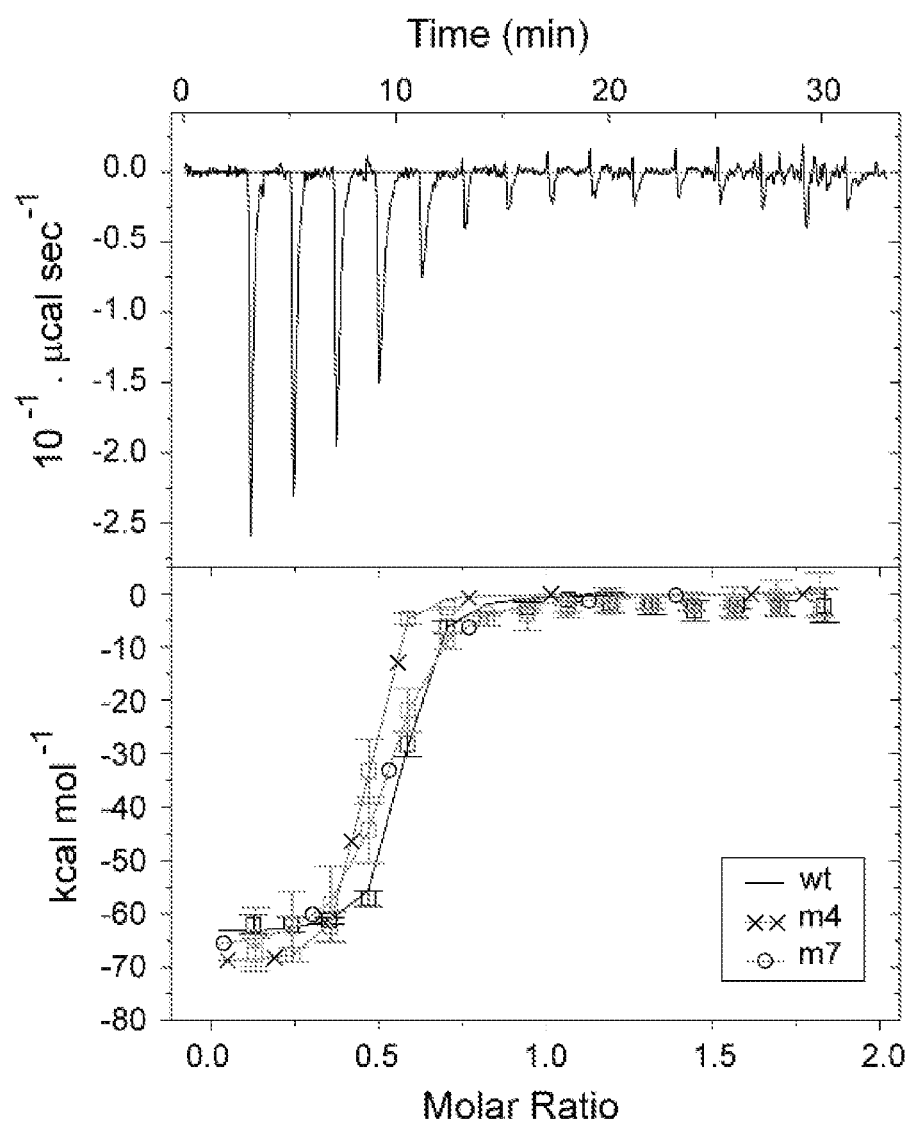
FIG. 8B is a chart showing the enthalpy change during titration with guanine in the wild-type guanine aptamer domain, m4 mutant aptamer domain, and m7 mutant aptamer domain.
Figure 9A:
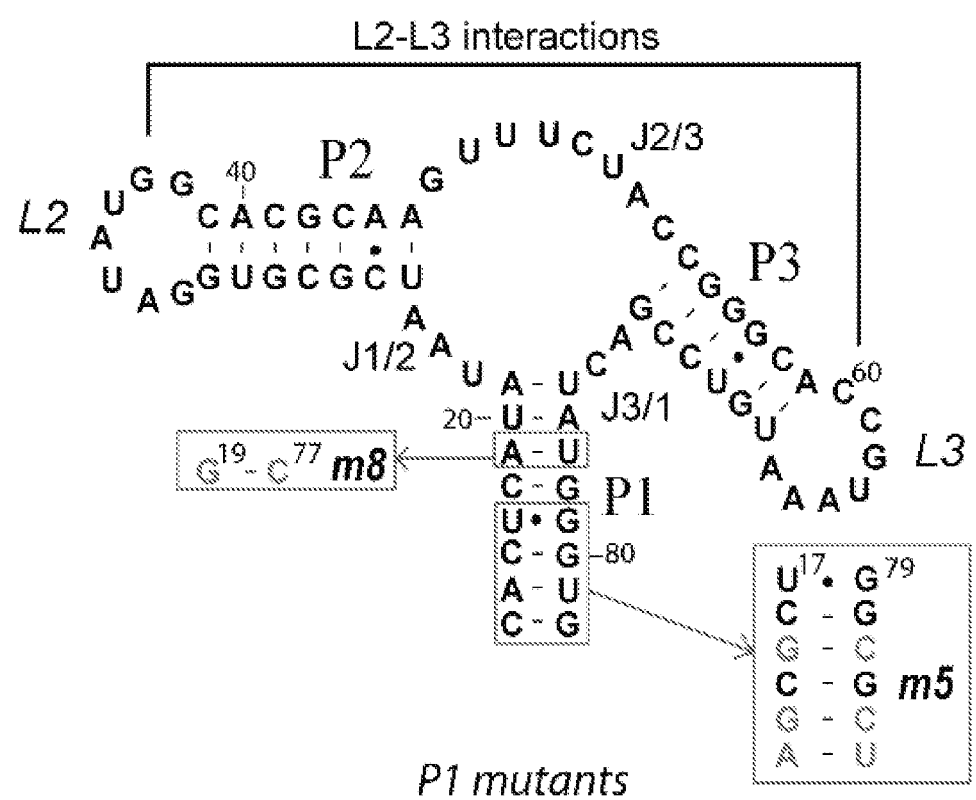
FIG. 9A depicts the sequence (SEQ ID NO: 25) and the secondary structure of the m5 and m8 mutants.
Figure 9B:
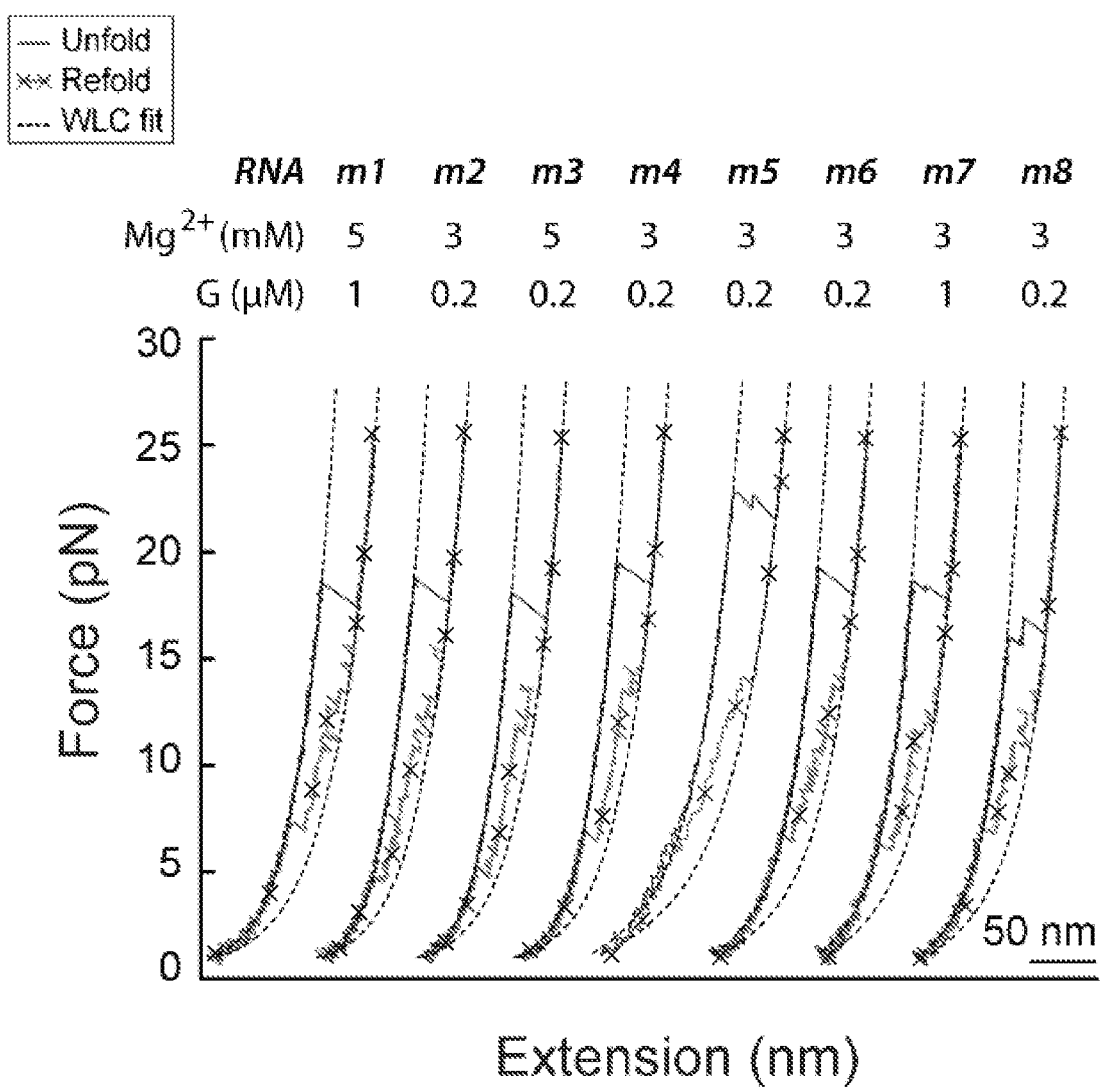
FIG. 9B is a chart showing the force-extension curves (FECs) for mutants m1-m8.
Figures 10A, 10B, 10C:
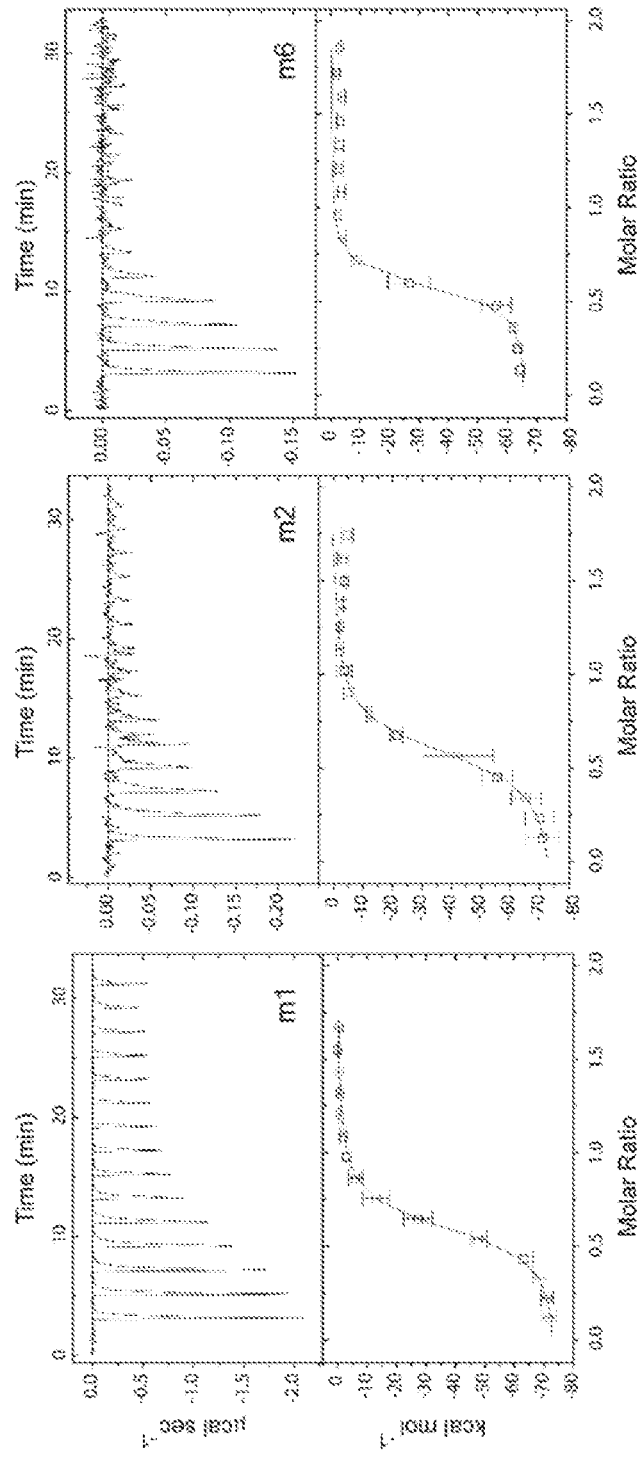
FIG. 10A is a chart showing that guanine titration follows an exothermic reaction in the kissing-loop mutant m1.
FIG. 10B is a chart showing that guanine titration follows an exothermic reaction in the kissing-loop mutant m2.
FIG. 10C is a chart showing that guanine titration follows an exothermic reaction in the kissing-loop mutant m6.

As indicated in FIGS. 9A-B, all mutants displayed the characteristic guanine-bound trajectories as described in FIG. 5F. The guanine-binding affinities for the kissing-loop mutants were determined by isothermal calorimetry. The wild-type aptamer exhibited a $K_D$=4.22±0.60 nM (FIG. 8B-C), which is similar to the $K_D$ values determined by in-line probing assay ($K_D$~5 nM). The results indicate that guanine binding is an enthalpically driven reaction (ΔH=−63.7±1.1 kcal/mol) resulting in a favorable free energy change (ΔG=−11.63±0.20 kcal/mol), which is consistent with the earlier reports. In m1 (G37A), the $K_D$ was off by 35 fold (FIG. 8C) indicating that the partially disrupted L2-L3 destabilized the binding core and hence, the least favorable free energy change (ΔG=−9.52±0.22 kcal/mol). In m3 (G38A), where the other base tetrad was disrupted, the $K_D$ was off by ~18 fold. The partial restoration in G37A/C61U (m2) resulted in ~9 fold off binding ($K_D$=36.0±0.2 nM). m4 (A59G/U67C) exhibited the strongest affinity for guanine with $K_D$=3.59±0.05 nM, which is better than the wild-type. In m6 (U67A) the affinity for guanine decreased slightly as $K_D$=6.7±0.63 nM. The $K_D$ for m7 (U25C) was observed at 16.9±1.0 nM indicating that a flexible J2/3, J1/2 do not support a strong binding (FIG. 8B-C). Except in m1, the free energy changes for the kissing loop mutants is comparable to the wild-type (FIG. 8C, FIGS. 10A-C), indicating that the binding properties of the receptor is not severely compromised. Next, the mutants m1-m8 were subjected in our single-molecule folding assay to further dissect the secondary and tertiary interactions one-at-a-time and follow their folding in three-dimension in real time.

Figure 11A:
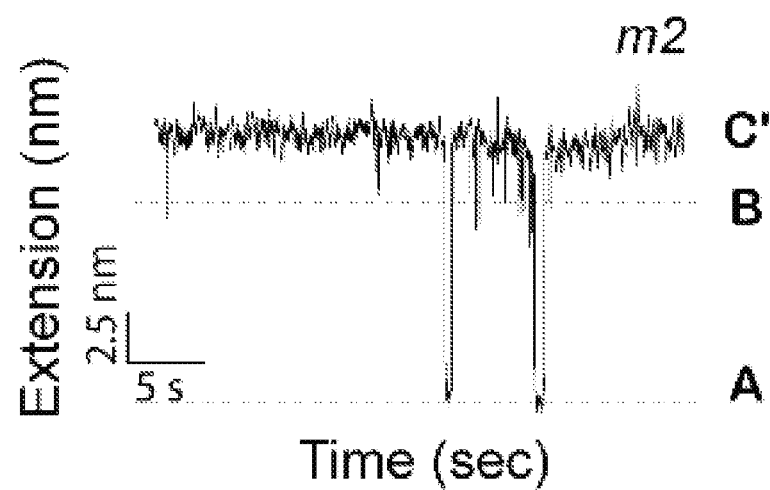
FIG. 11A is an extension vs. time trace for the m2 mutant.
Figure 11B:
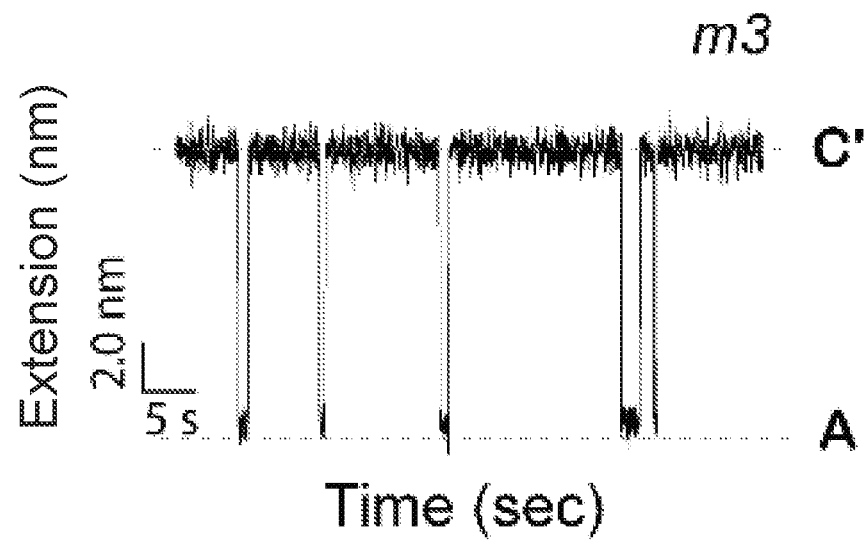
FIG. 11B is an extension vs. time trace for the m3 mutant.
Figure 11C:
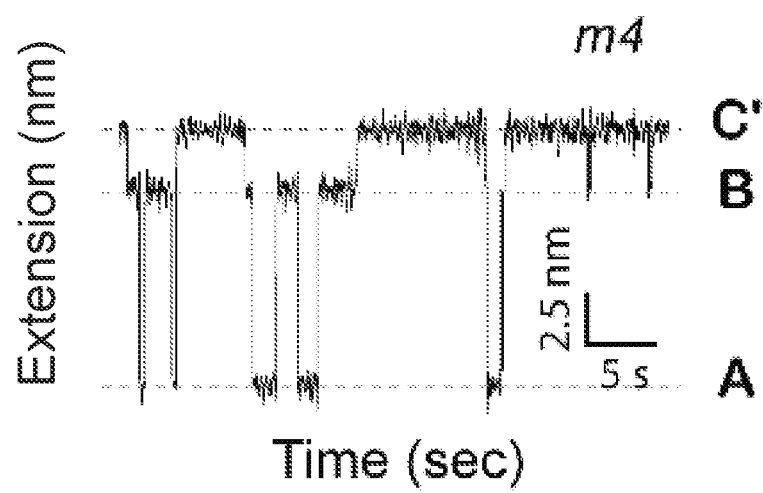
FIG. 11C is an extension vs. time trace for the m4 mutant.
Figure 11D:
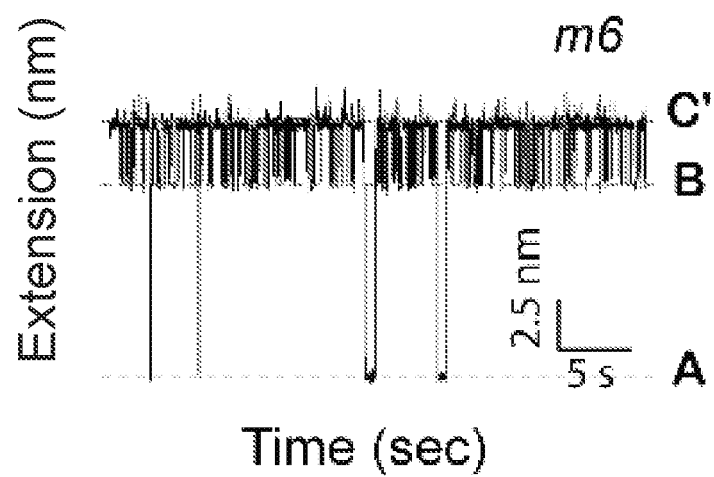
FIG. 11D is an extension vs. time trace for the m6 mutant.
Figure 11E:
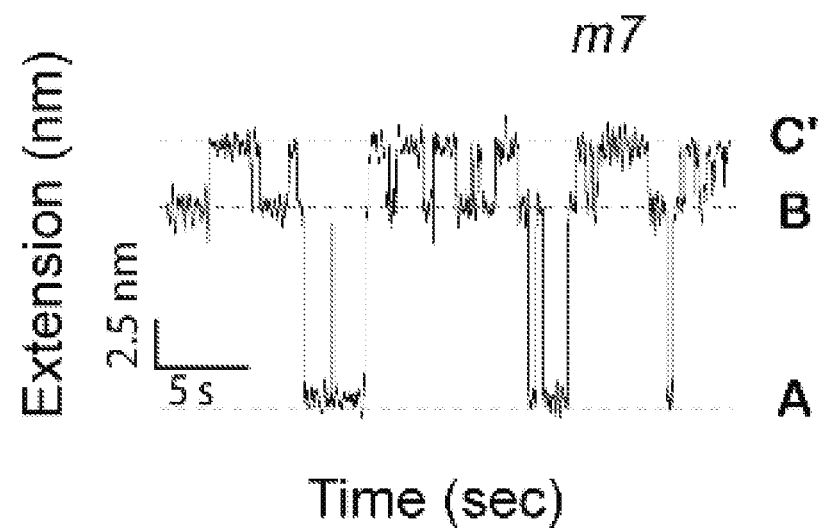
FIG. 11E is an extension vs. time trace for the m7 mutant.

At equilibrium, the m3 with partially disrupted loop-loop interactions, displayed the C'↔A hopping, instead of a discrete C'↔B and B↔A fluctuation (FIG. 11B). Similar C'↔A fluctuations were observed in m1 (Table 1). This suggested that the C'↔B transitions observed in the wild-type guanine-aptamer are indeed due to the stable L2-L3 interactions. The restorative m2 mutant exhibited a transient C'↔B in conjunction with the C'↔A hopping (FIG. 11A). In m4, both C'B and BA fluctuations were observed, however the kissing rate between L2-L3 is reduced by 4.5 fold than the wild-type (Table 1), highlighting that the RNA favored the un-kissed conformation due to the conformational rigidity of the P3/L3 junction. The m6, on the contrary, with its larger loop 3, displayed 8.33 times faster kissing indicating a dynamic L2-L3 interaction. This strongly supported that a flexible P3/L3 interface is crucial for the intramolecular loop-loop interaction. In m7, the L2-L3 and the P1-helix displayed increased unfolding kinetics (Table 1) suggesting that a flexible J2/3 and J1/2 folds poorly around guanine, which is consistent with the observed low guanine affinity in ITC.

Figure 11F:
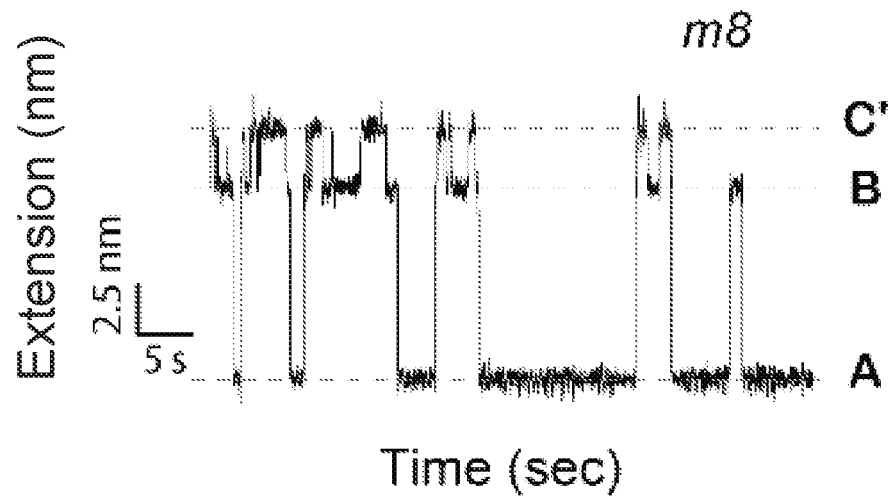
FIG. 11F is an extension vs. time trace for the m8 mutant.
Figure 11G:
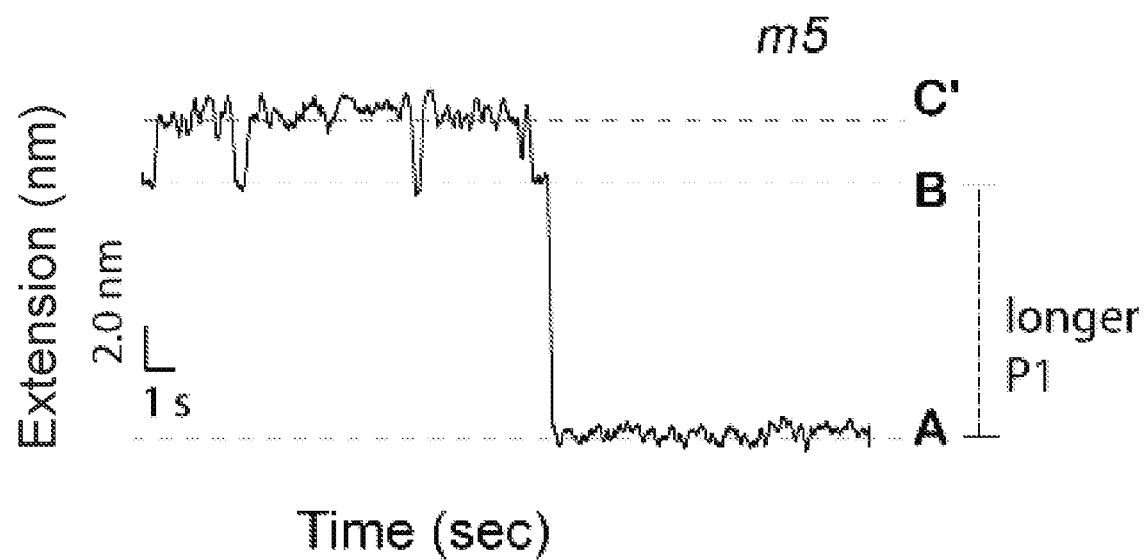
FIG. 11G is an extension vs. time trace for the m5 mutant.

The P1-helix mutants, namely m5 and m8 (FIGS. 9A-B) specifically modulated the BA transition as expected. Thus, the former exhibited a longer BA transition (FIG. 11G) and the latter exhibited reduced P1-unfolding rate, due to the GC substitution (FIG. 11F, Table 1).

By combining mutational strategies with single-molecule and ITC experiments, supporting evidence is provided for the secondary and the tertiary rearrangements that takes place upon closing of the junction J2/3. This conclusively proves that the structural assignments to the folding transitions in FIGS. 6A-B are accurate.

Force-Dependent Folding of the Secondary and Tertiary Elements

Figure 12A:
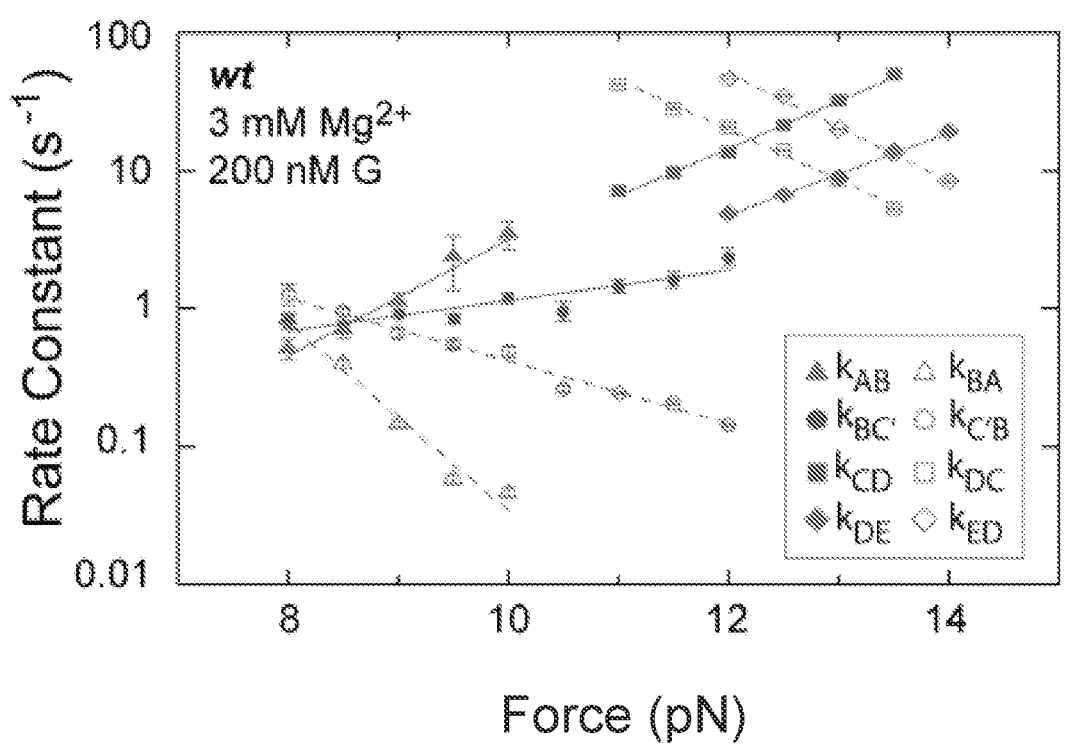
FIG. 12A is a chart showing force-dependent folding rates for the tertiary and the secondary structural elements in the wild-type guanine aptamer.
Figure 12F:
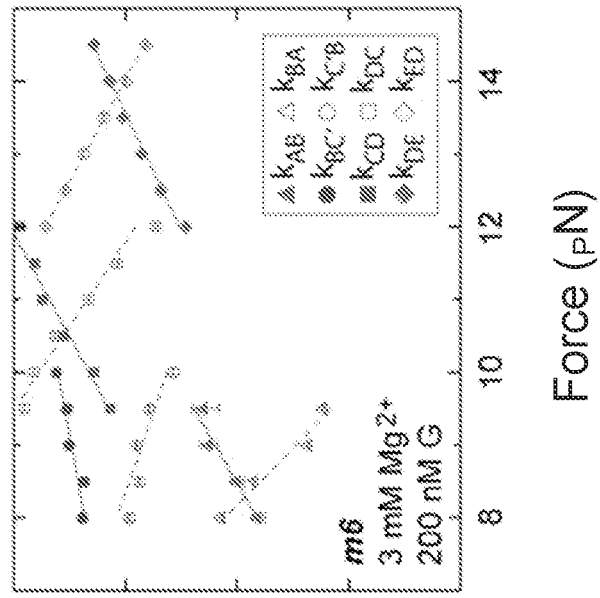
FIG. 12F is a chart showing force-dependent folding rates for the tertiary and the secondary structural elements in the m6 mutant aptamer.
Figure 12E:
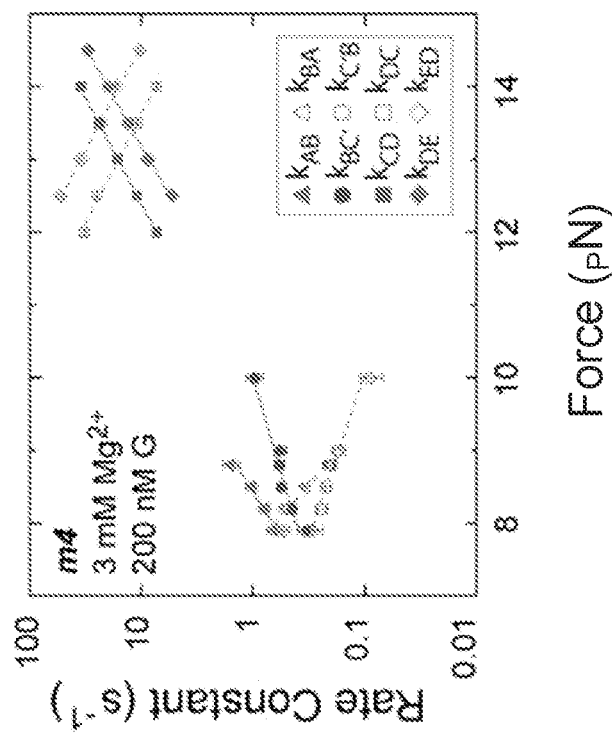
FIG. 12E is a chart showing force-dependent folding rates for the tertiary and the secondary structural elements in the m4 mutant aptamer.

From the equilibrium experiments in this study, it is evident that the folding order is similar in the guanine- and the adenine-aptamer. The P2 folds first, followed by P3, which is then followed by P1. The kinetic rates; however are dependent on the applied force, which in turn is dictated by the individual hairpin sequence. The kinetic rates in the two riboswitches are compared in Table 3. In FIG. 12A, the force-dependent folding ($k_f$, open markers) and the unfolding ($k_u$, filled markers) rate constants for the secondary and the tertiary interactions are indicated. Data sets are fitted with the relationship, $$k(F) = k_0 \exp\frac{F\Delta X^\ddagger}{k_B T},$$

where $k_0$ is the intrinsic rate, $\Delta X^\ddagger$ is the distance to the transition state, and $k_B$ the Boltzman constant. Near equilibrium ($F^{eq}$), the forward and the reverse rates are equal ($k_f$≈$k_u$). In fact, the determination of $F^{eq}$ can shed important information on the stabilities of individual structural elements. Results from this study indicates that the $F^{eq}$ for P2 is greater (13.5±0.03 pN) than P3 (12.2±0.02 pN), which implies that P3 is less stable than P2. The free energy values, ΔG(0) in Table 1 is also indicative of a more stable P2 helix, although by a small margin. In m6, due to the U67A replacement, the ΔG(0)$_{P3}$ decreased sharply from −16.3 kT in the wild-type to −11.1 kT, thereby reducing the stability. Similarly, in m4 (A59G/U67C), the stability increased slightly by 1 kT. The data from the mutants thus support our initial observation that P3 may be the flexible domain. It is noteworthy, that for the intramolecular loop-loop interactions, the hairpins have to accommodate significant conformational deformity. Therefore, between the P2 and the P3 hairpins, it is likely that the latter undergoes the required conformational mobility. It is reminded that the guanine-responsive structural rearrangements are initiated by the closing of the J2/3 (FIG. 6A-B), which probably allows the deformity in the P3 such that the end loops (L2 and L3) are juxtaposed to each other. This, in turn enables the formation of the long-range interactions between L2 and L3. Once stable tertiary interactions are established, the folding of P1 follows. It appears that after the P3 has accommodated the necessary deformations, the P1 stacks coaxially on P3 as shown by the crystal structure. Significantly, a near similar $F^{eq}$≈8 pN for the tertiary L2-L3 and the P1-helix suggests that these two events may be cooperative and linked to each other, which takes place in rapid succession. Thus, in m4, an altered L2-L3 affected the stability of the P1-helix, as indicated by a decrease in the ΔG from −13.9 $k_B$T (wild-type) to −12.5 $k_B$T (m4) (Table 1). In m8, a stable P1 with ΔG(0)=−14.3 $k_B$T, showed a slightly stable L2-L3. In m7 a flexible J2/3 rendered a less stable L2-L3 (ΔG=−6.5 kT), which in turn adversely affected the stability of the P1-helix (ΔG=−11.8 kT). A partially disrupted L2-L3 in m1, m2 and m3 mutants resulted in the merger of the two folding structures (C'B and BA) into C'A, wherein the combined $F^{eq}$ for the two transitions shifted to lower force at 6 pN (Table 1, FIGS. 12B-D). The free energy changes in the absence of force, thus underscores that the L2-L3 interactions cooperatively assist in the folding of the P1 stem.

The Purine Analog 2, 6 Diaminopurine do not Affect the L2-L3 Dynamics

Guanine binds to the aptamer via nucleobases $U^{22}$, $U^{47}$, $U^{51}$ and $C^{74}$ in the junction J1/2, J2/3 and J3/1. The hydrogen bonding between $C^{74}$ with the functional group in the $6^{th}$ position of the purine is deterministic for ligand recognition. The purine analog 2,6-diaminopurine (DAP) differs from guanine in having an amino group in the $6^{th}$ position (FIG.

Figure 13:
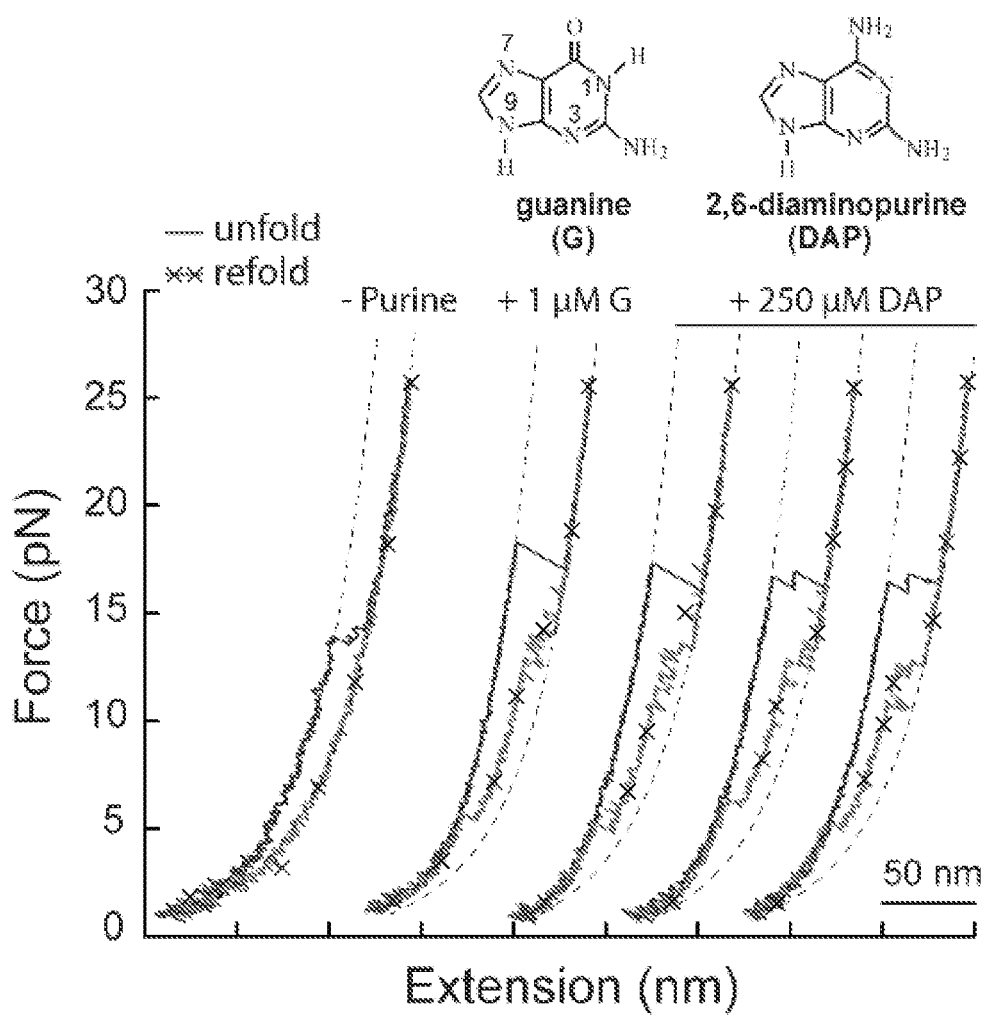
FIG. 13 shows a force extension curve (FEC) for the wild-type guanine aptamer in 3 mM $MgCl_2$, +1 μM guanine, +250 μM diaminopurine (DAP).

13), and thus disrupts the hydrogen bonding pattern. Previous in-line measurements have indicated that the $K_D$ for DAP is ~10 µM. In order to investigate if the loop-loop dynamics in the guanine-riboswitch are affected with a change in the ligand, mechanical assays in the presence of DAP were performed. FIG. 13, shows that the unfolding trajectories in DAP and guanine are similar. Furthermore, a near similar L2-L3 kinetics highlighted that the tertiary and the secondary interactions remained unaffected by replacing guanine with DAP (Table 1).

Genetic Manipulations to Uncover the Transcriptional Regulation by Riboswitches

Figure 14:
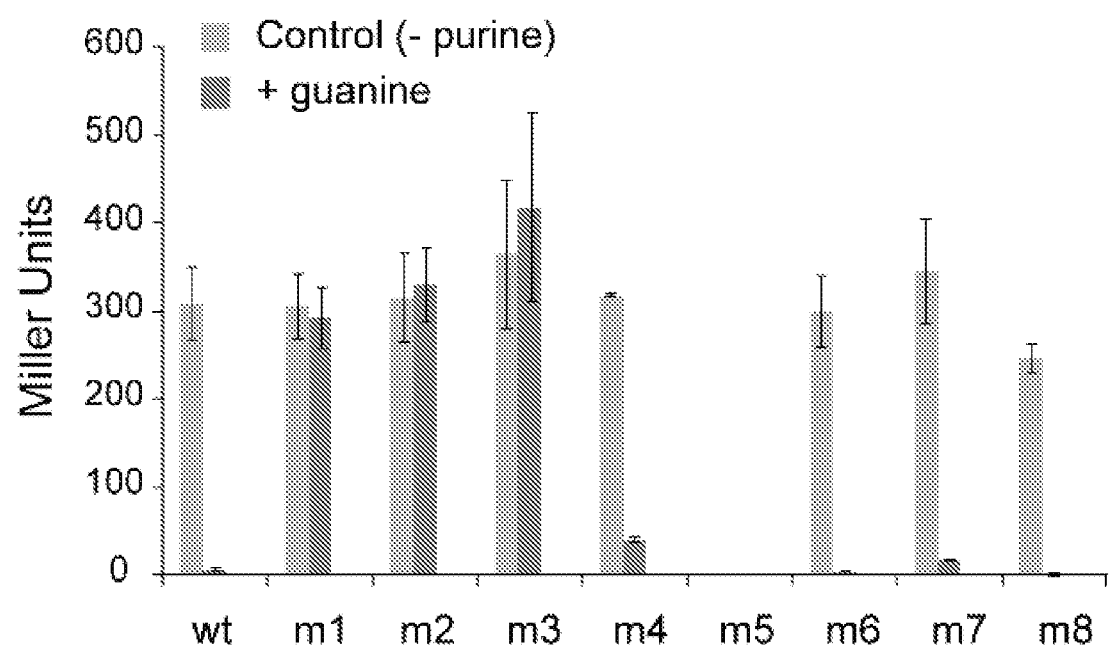
FIG. 14 is a β-galactosidase reporter assay measuring the riboswitch mediated transcriptional control in the presence and absence of guanine for the wild-type guanine aptamer and mutants m1-m8.
Figure 15A:
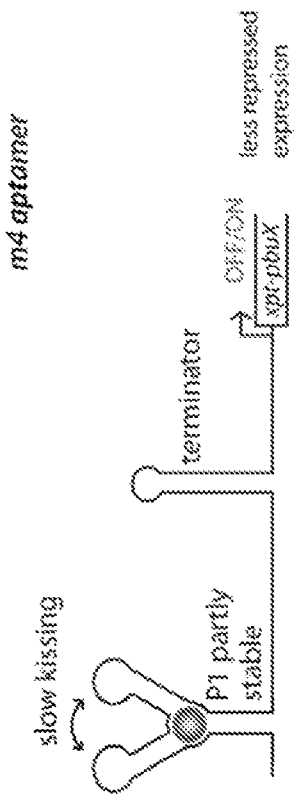
FIG. 15A depicts optimal kissing in a wild-type guanine aptamer.
Figure 15B:
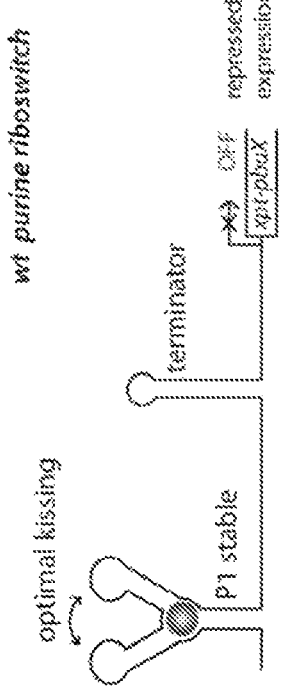
FIG. 15B depicts slowing kissing in the mutant guanine aptamer m4.
Figure 15C:
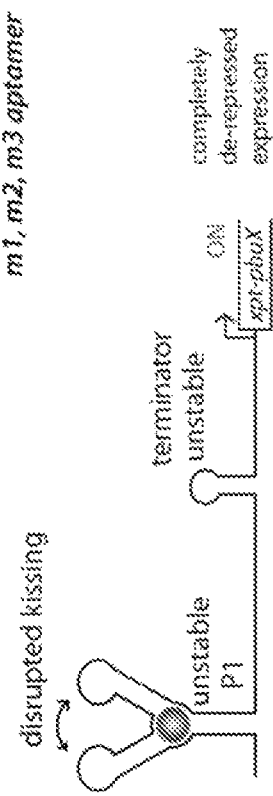
FIG. 15C depicts fast kissing in the mutant guanine aptamer m6.
Figure 15D:
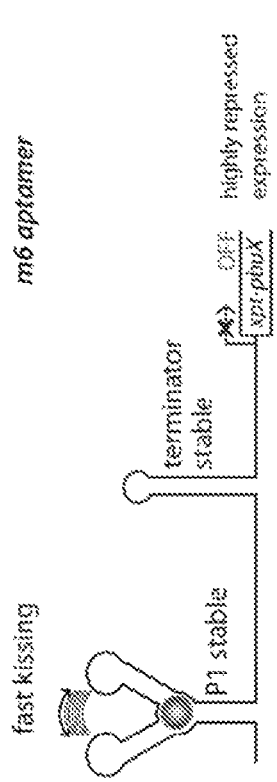
FIG. 15D depicts disrupted kissing in the mutant guanine aptamers m1, m2, and m3.

Kissing-loop mutants were analyzed to determine whether they can exert riboswitch activities by controlling transcription termination, given that the guanine binding was retained in all of them. To test this, a β-galactosidase reporter assay was performed in *B.subtilis*. FIG. 14 shows the expression of the lac Z in the presence and absence of guanine in mutants m1-m8. The gene expression is repressed in wild-type due to the transcription termination in the presence of guanine. In m6, the expression was highly repressed, which exceeded the wild-type repression by ~3 fold. The fast kissing dynamics between the L2-L3 probably have a stabilizing effect on P1, and therefore an increase in the transcription termination is observed. In m4 with slow kissing, the expression was moderately repressed. The expression was ~7 fold higher than the wild-type, suggesting that the slow L2-L3 dynamics do not have a stabilizing effect on the P1. In m1, m2 and m3 the riboswitch activities were completely de-repressed due to the L2-L3 aberrations. This underscores that the L2-L3 dynamics are directly involved in the P1-helix formation, which affects the terminator hairpin downstream that ultimately results in an alteration of the riboswitch activities. Thus, it is apparent that the tertiary interactions in the purine riboswitches play an important role in exerting the transcriptional control, although all the mutants showed intact ligand binding properties. The effect of kissing dynamics on the purine riboswitch activities are summarized in FIGS. 15A-D. The m7 with a flexible J2/3 showed higher expression (~2.5 fold) than wild-type, similar to the m4. The m8 with a stable P1-helix displayed stringent control in guanine, whereas m5 exhibited a constantly repressed expression irrespective of the presence or absence of any purine in the media.

Structural Conformations of the Aptamer Domain of the Guanine Riboswitch

The aptamer domain of a guanine riboswitch can switch between six different structural conformations with different kinetics to control gene expression. The six structural conformations include: a linear conformation, a P2 helix conformation; a P2-P3 helix conformation; a L2-L3 unkissed conformation; a L2-L3 kissed conformation; and a guanine-bound conformation (FIG. 6B).

The addition of magnesium ($Mg^{2+}$) can switch the aptamer domain from the linear conformation to the P2 helix conformation. The addition of magnesium ($Mg^{2+}$) can switch the aptamer domain from the P2 helix conformation to the P2-P3 helix conformation. The addition of guanine can switch the aptamer domain from the P2-P3 conformation to the guanine bound conformation in 1-step. The addition of guanine can switch the aptamer domain from the P2-P3 conformation to the L2-L3 kissed conformation and then to the guanine bound conformation in 2-steps. The addition of guanine can switch the aptamer domain from the P2-P3 conformation to the L2-L3 unkissed conformation, then to the L2-L3 kissed conformation and then finally to the guanine bound conformation in 3-steps (FIG. 6B). Except for the linear state, each of the 5 structural conformations of the guanine aptamer domain can include one or more of the following components: P1, P2, P3, L2, L3, J1/2, J2/3, and J3/2. Many of these components are formed and/or interact with each other during the switching from one structural conformation to the next structural conformation.

Mutants m1-m8

Sequences for the mutant guanine-sensing aptamers m1-m8 are disclosed in SEQ ID NOs: 2-9 and FIGS. 4C-4J, as described in Table 4.

TABLE 4

| Mutant | SEQ ID NO: | FIG. |
|--------|------------|------|
| m1 | 2 | 4C |
| m2 | 3 | 4D |
| m3 | 4 | 4E |
| m4 | 5 | 4F |
| m5 | 6 | 4G |
| m6 | 7 | 4H |
| m7 | 8 | 4I |
| m8 | 9 | 4J |

Mutant m1

In the m1 mutant, the nucleobase G37 is replaced with an adenine residue in the L2 loop, as shown in FIG. 4C, which results in a modified L2 sequence with altered base-quadruple interactions.

Mutant m2

In the m2 mutant, nucleobase G37 is replaced with an adenine residue in the L2 loop and nucleobase C61 is replaced with a uracil residue in the L3 loop, as shown in FIG. 4D, which results in a modified L2 and L3 sequence with altered base-quadruple interactions.

Mutant m3

In the m3 mutant, nucleobase G38 is replaced with an adenine residue in the L2 loop, as shown in FIG. 4E, which results in a modified L2 sequence with altered base quadruple interactions.

Mutant m4

In the m4 mutant, nucleobase A59 is replaced with a guanine residue and nucleobase U67 is replaced with a cytosine residue in the P3 hairpin, as shown in FIG. 4F, which results in a mutated P3 hairpin and a L3 that remains intact.

Mutant m5

In the m5 mutant, a longer P1 helix is introduced by replacing the lower half of the stem with new bases, as shown in FIG. 4G, which increases the total length of the sequence from 69 to 73 nucleotides.

Mutant m6

In the m6 mutant, nucleobase U67 is replaced with an adenine residue in the L3 loop, as shown in FIG. 4H, which results in a shorter P3 hairpin and a larger L3 loop.

Mutant m7

In the m7 mutant, nucleobase $U^{25}$ is replaced with a cytosine residue in J1/2, as shown in FIG. 4I, which results in a more flexible and longer J1/2.

Mutant m8

Figure 4J:
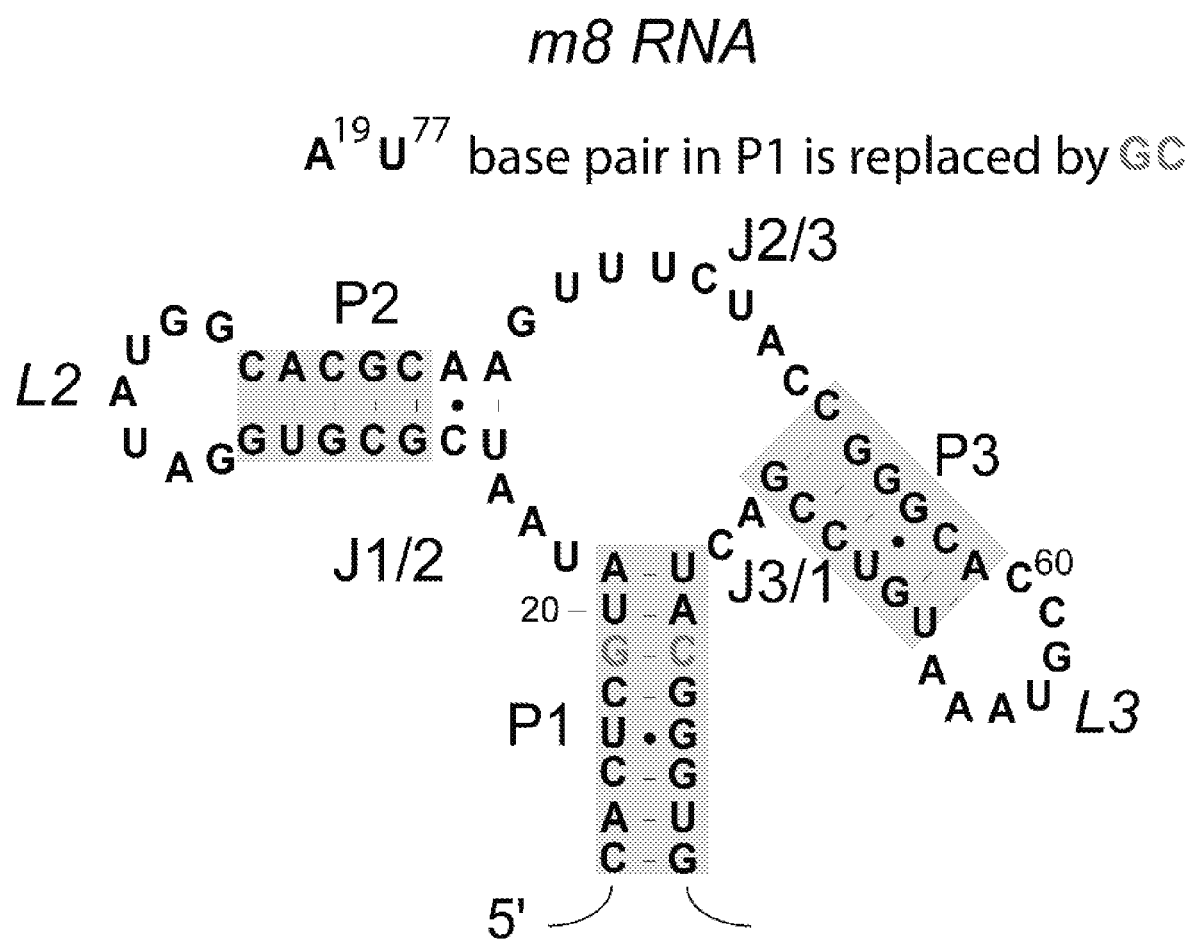
FIG. 4J depicts the nucleotide sequence (SEQ ID NO: 23) for the m8 mutant guanine aptamer and each of the structural components of the m8 mutant guanine aptamer.

In m8, nucleobase A19 is replaced with a guanine residue in the P1 hairpin and nucleobase $U^{77}$ is replaced with a cytosine residue in the P1 hairpin, as shown in FIG. 4J, which results in a stable P1 hairpin.

Hairpins (P), Loops (L), and Junctions (J) of the Mutated Guanine Aptamer Domain An aptamer domain of the purine riboswitch can comprise one or more hairpin (P1, P2, and P3), one or more loops (L2 and L3) and one or more junctions (J1/2, J2/3, and J3/1).

An aptamer domain of the guanine riboswitch can comprise one or more hairpin (P1, P2, and P3), one or more loops (L2 and L3) and one or more junctions (J1/2, J2/3, and J3/1).

An aptamer domain of the adenine riboswitch can comprise one or more hairpin (P1, P2, and P3), one or more loops (L2 and L3) and one or more junctions (J1/2, J2/3, and J3/1).

A mutated aptamer domain of the guanine riboswitch can comprise one or more hairpin (P1, P2, and P3), one or more loops (L2 and L3) and one or more junctions (J1/2, J2/3, and J3/1). One or more of the P1, P2, and P3 can comprise a base pair mutation, as shown in Table 5.

TABLE 5

| Hairpin | Mutant | Mutated Sequence |
|---|---|---|
| P1 | m5 | 5'-AGCGCUCAUA-3' (SEQ ID NO: 10) |
| P1 | m5 | 5'-UAUGGGCGCU-3' (SEQ ID NO: 11) |
| P1 | m8 | 5'-CACUCGUA-3' |
| P1 | m8 | 5'-UACGGGUG-3' |
| P3 | m4 | 5'-CGGGCG-3' |
| P3 | m4 | 5'-CGUCCG-3' |
| P3 | m6 | 5'-CGGGC-3' |
| P3 | m6 | 5'-GUCCG-3' |

The one or more mutated aptamer domain disclosed herein can comprise a sequence that is at least 100% identical to the P1 hairpin sequence before the L2 loop, as shown in SEQ ID NO. 10, and at least 100% identical to the P1 hairpin sequence after the L3 loop, as shown in SEQ ID NO. 11, in the m5 mutant. The one or more mutated aptamer domain disclosed herein can comprise a sequence that is at least 95% identical to SEQ ID NO. 10 and at least 95% identical to SEQ ID NO. 11, in the m5 mutant. The one or more mutated aptamer domain disclosed herein can comprise a sequence that is at least 90% identical to SEQ ID NO. 10 and at least 90% identical to SEQ ID NO. 11, in the m5 mutant. The one or more mutated aptamer domain disclosed herein can comprise a sequence that is at least 85% identical to SEQ ID NO. 10 and at least 85% identical to SEQ ID NO. 11, in the m5 mutant.

The one or more mutated aptamer domain disclosed herein can comprise a sequence that is at least 100% identical to the P1 hairpin sequence before the L2 loop, as shown in Table 5, and at least 100% identical to the P1 hairpin sequence after the L3 loop, as shown in Table 5, in the m8 mutant. The one or more mutated aptamer domain disclosed herein can comprise a sequence that is at least 95% identical to the P1 hairpin sequence before the L2 loop, as shown in Table 5, and at least 95% identical to the P1 hairpin sequence after the L3 loop, as shown in Table 5, in the m8 mutant. The one or more mutated aptamer domain disclosed herein can comprise a sequence that is at least 90% identical to the P1 hairpin sequence before the L2 loop, as shown in Table and at least 90% identical to the P1 hairpin sequence after the L3 loop, as shown in Table 5, in the m8 mutant. The one or more mutated aptamer domain disclosed herein can comprise a sequence that is at least 85% identical to the P1 hairpin sequence before the L2 loop, as shown in Table 5, and at least 85% identical to the P1 hairpin sequence after the L3 loop, as shown in Table 5, in the m8 mutant.

The one or more mutated aptamer domain disclosed herein can comprise a sequence that is at least 100% identical to the P3 hairpin sequence before the L3 loop, as shown in Table 5, and at least 100% identical to the P3 hairpin sequence after the L3 loop, as shown in Table 5, in the m4 mutant. The one or more mutated aptamer domain disclosed herein can comprise a sequence that is at least 95% identical to the P3 hairpin sequence before the L3 loop, as shown in Table 5, and at least 95% identical to the P3 hairpin sequence after the L3 loop, as shown in Table 5, in the m4 mutant. The one or more mutated aptamer domain disclosed herein can comprise a sequence that is at least 90% identical to the P3 hairpin sequence before the L3 loop, as shown in Table and at least 90% identical to the P3 hairpin sequence after the L3 loop, as shown in Table 5, in the m4 mutant. The one or more mutated aptamer domain disclosed herein can comprise a sequence that is at least 85% identical to the P3 hairpin sequence before the L3 loop, as shown in Table 5, and at least 85% identical to the P3 hairpin sequence after the L3 loop, as shown in Table 5, in the m4 mutant.

The one or more mutated aptamer domain disclosed herein can comprise a sequence that is at least 100% identical to the P3 hairpin sequence before the L3 loop, as shown in Table 5, and at least 100% identical to the P3 hairpin sequence after the L3 loop, as shown in Table 5, in the m6 mutant. The one or more mutated aptamer domain disclosed herein can comprise a sequence that is at least 95% identical to the P3 hairpin sequence before the L3 loop, as shown in Table 5, and at least 95% identical to the P3 hairpin sequence after the L3 loop, as shown in Table 5, in the m6 mutant. The one or more mutated aptamer domain disclosed herein can comprise a sequence that is at least 90% identical to the P3 hairpin sequence before the L3 loop, as shown in Table and at least 90% identical to the P3 hairpin sequence after the L3 loop, as shown in Table 5, in the m6 mutant. The one or more mutated aptamer domain disclosed herein can comprise a sequence that is at least 85% identical to the P3 hairpin sequence before the L3 loop, as shown in Table 5, and at least 85% identical to the P3 hairpin sequence after the L3 loop, as shown in Table 5, in the m6 mutant.

One or more of L2 and L3 can comprise a base pair mutation, as shown in Table 6.

TABLE 6

| Loop | Mutant | Mutated Sequence |
|---|---|---|
| L2 | m1 | 5'-GAUAUAG-3' |
| L2 | m3 | 5'-GAUAUGA-3' |
| L3 | m2 | 5'-CUGUAAA-3' |
| L3 | m6 | 5'-ACCGUAAAA-3' |

The one or more mutated aptamer domain disclosed herein can comprise a sequence that is at least 100% identical to the L2 sequence in the m1 mutant, as shown in Table 6. The one or more mutated aptamer domain disclosed herein can comprise a sequence that is at least 95% identical to the L2 sequence in the m1 mutant, as shown in Table 6. The one or more mutated aptamer domain disclosed herein can comprise a sequence that is at least 90% identical to the L2 sequence in the m1 mutant, as shown in Table 6. The one or more mutated aptamer domain disclosed herein can comprise a sequence that is at least 85% identical to the L2 sequence in the m1 mutant, as shown in Table 6.

The one or more mutated aptamer domain disclosed herein can comprise a sequence that is at least 100% identical to the L2 sequence in the m3 mutant, as shown in Table 6. The one or more mutated aptamer domain disclosed herein can comprise a sequence that is at least 95% identical to the L2 sequence in the m3 mutant, as shown in Table 6. The one or more mutated aptamer domain disclosed herein can comprise a sequence that is at least 90% identical to the L2 sequence in the m3 mutant, as shown in Table 6. The one or more mutated aptamer domain disclosed herein can comprise a sequence that is at least 85% identical to the L2 sequence in the m3 mutant, as shown in Table 6.

The one or more mutated aptamer domain disclosed herein can comprise a sequence that is at least 100% identical to the L2 sequence and at least 100% identical to the L3 sequence in the m2 mutant, as shown in Table 6. The one or more mutated aptamer domain disclosed herein can comprise a sequence that is at least 95% identical to the L2 sequence and at least 95% identical to the L3 sequence in the m2 mutant, as shown in Table 6. The one or more mutated aptamer domain disclosed herein can comprise a sequence that is at least 90% identical to the L2 sequence and at least 90% identical to the L3 sequence in the m2 mutant, as shown in Table 6. The one or more mutated aptamer domain disclosed herein can comprise a sequence that is at least 85% identical to the L2 sequence and at least 85% identical to the L3 sequence in the m2 mutant, as shown in Table 6.

The one or more mutated aptamer domain disclosed herein can comprise a sequence that is at least 100% identical to the L3 sequence in the m6 mutant, as shown in Table 6. The one or more mutated aptamer domain disclosed herein can comprise a sequence that is at least 95% identical to the L3 sequence in the m6 mutant, as shown in Table 6. The one or more mutated aptamer domain disclosed herein can comprise a sequence that is at least 90% identical to the L3 sequence in the m6 mutant, as shown in Table 6. The one or more mutated aptamer domain disclosed herein can comprise a sequence that is at least 85% identical to the L3 sequence in the m6 mutant, as shown in Table 6.

One or more of the J1/2, J2/3, and J3/1 can comprise a base pair mutation, as shown in Table 7.

TABLE 7

| Junction | Mutant | Mutated Sequence |
|---|---|---|
| J1/2 | m7 | 5'-UAACC-3' |

The one or more mutated aptamer domain disclosed herein can comprise a sequence that is at least 100% identical to the J1/2 sequence in the m7 mutant, as shown in Table 7. The one or more mutated aptamer domain disclosed herein can comprise a sequence that is at least 95% identical to the J1/2 sequence in the m7 mutant, as shown in Table 7. The one or more mutated aptamer domain disclosed herein can comprise a sequence that is at least 90% identical to the J1/2 sequence in the m7 mutant, as shown in Table 7. The one or more mutated aptamer domain disclosed herein can comprise a sequence that is at least 85% identical to the J1/2 sequence in the m7 mutant, as shown in Table 7.

Conformational Dynamics of full-length Guanine Riboswitch

Figure 17A:
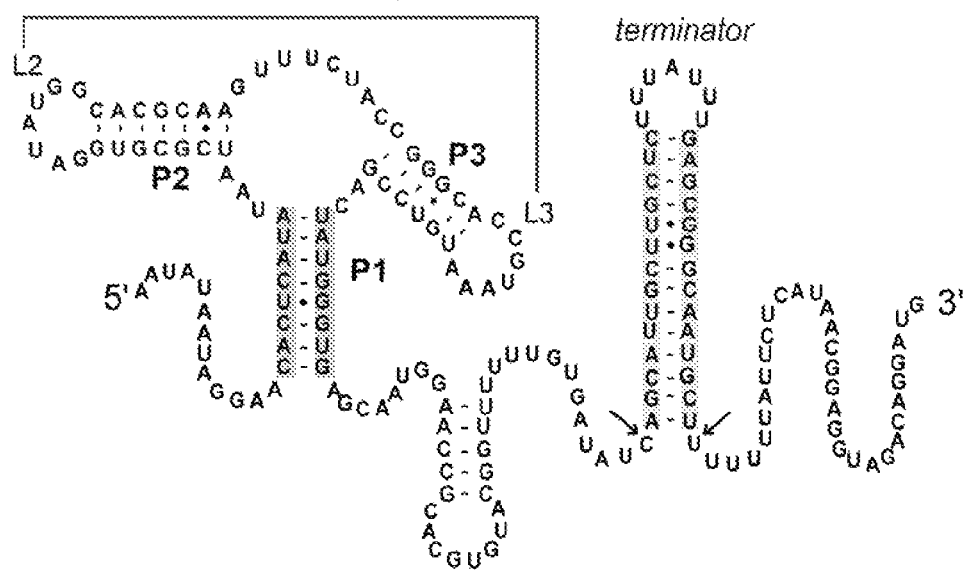
FIG. 17A depicts the sequence (SEQ ID NO: 26) and the secondary structure of the xpt-pbuX guanine-sensing aptamer in high guanine.
Figure 17B:
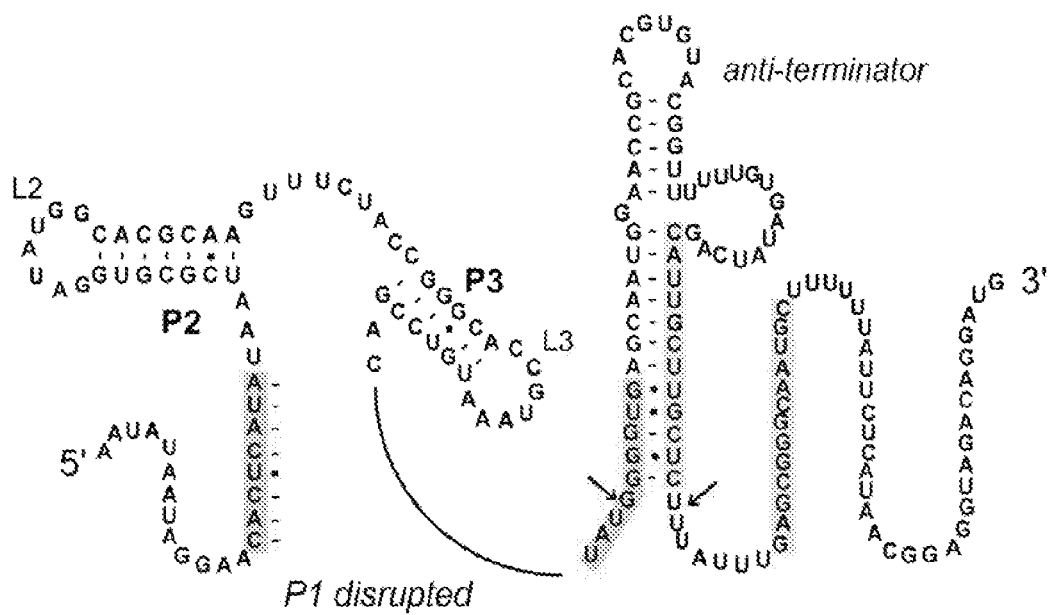
FIG. 17B depicts the sequence (SEQ ID NO: 27) and the secondary structure of the xpt-pbuX guanine-sensing aptamer in low guanine.
Figure 17C:
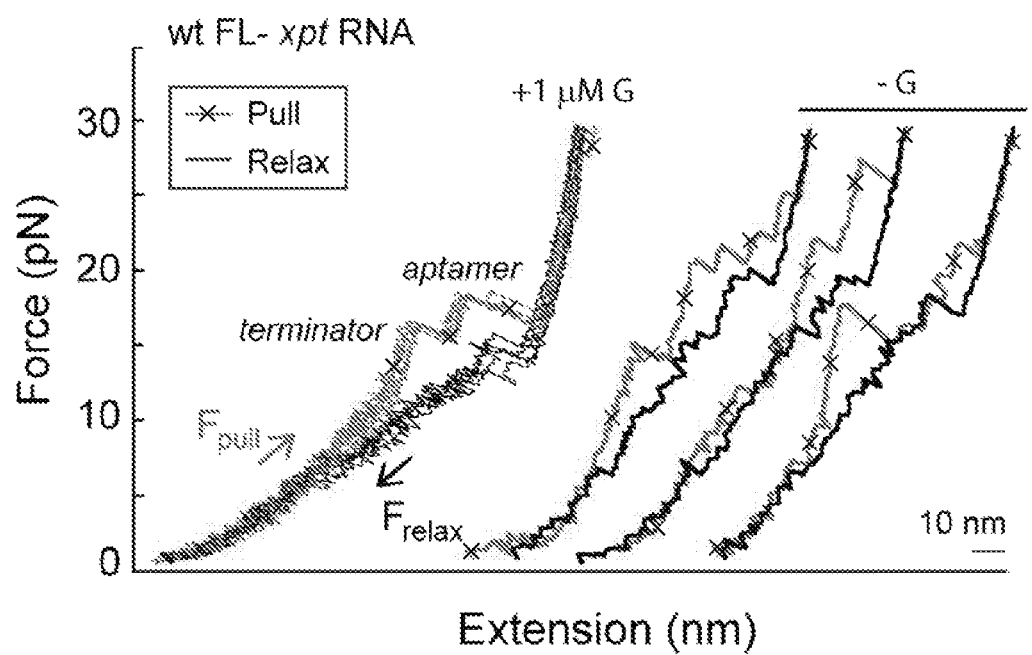
FIG. 17C shows force extension curves (FECs) in the presence (+1 µM G) and absence (−G) of guanine.
Figure 17D:
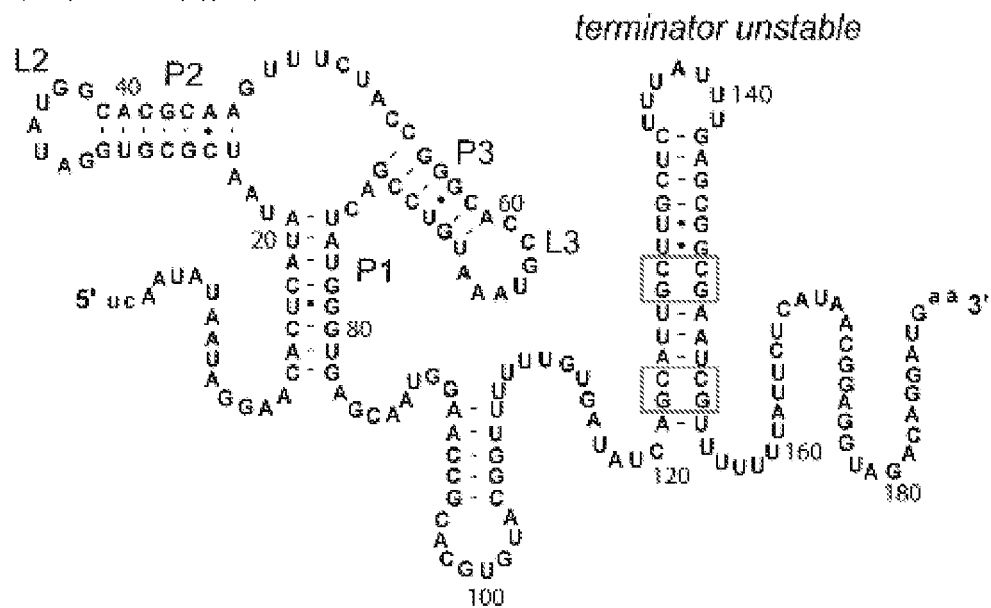
FIG. 17D depicts the sequence (SEQ ID NO: 28) and the full-length terminator mutant.
Figure 17E:
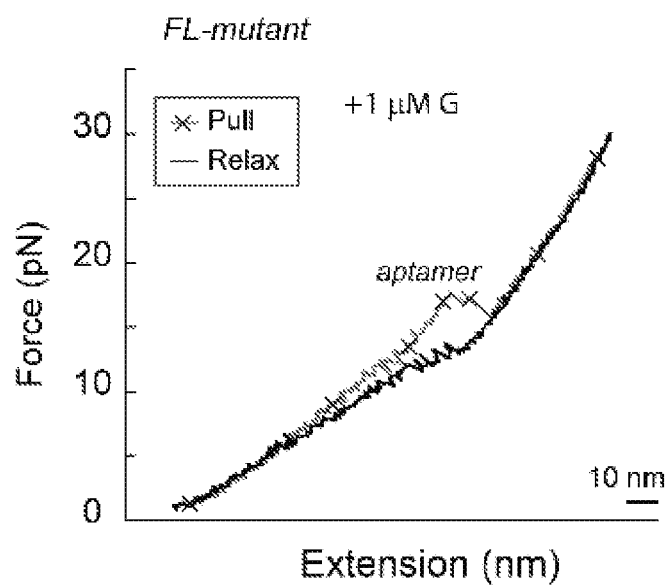
FIG. 17E shows a force extension curve (FEC) for the full-length terminator mutant.
Figure 18A:
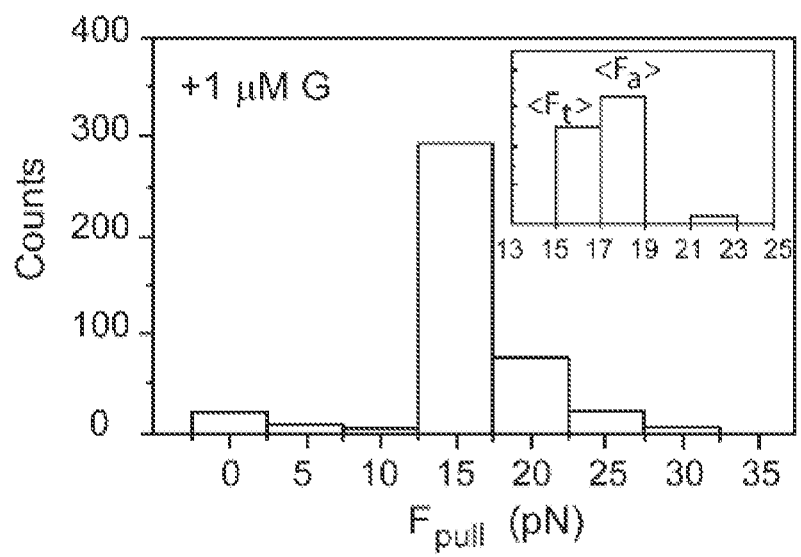
FIG. 18A is a force histogram in the presence of 1 µM guanine.
Figure 18B:
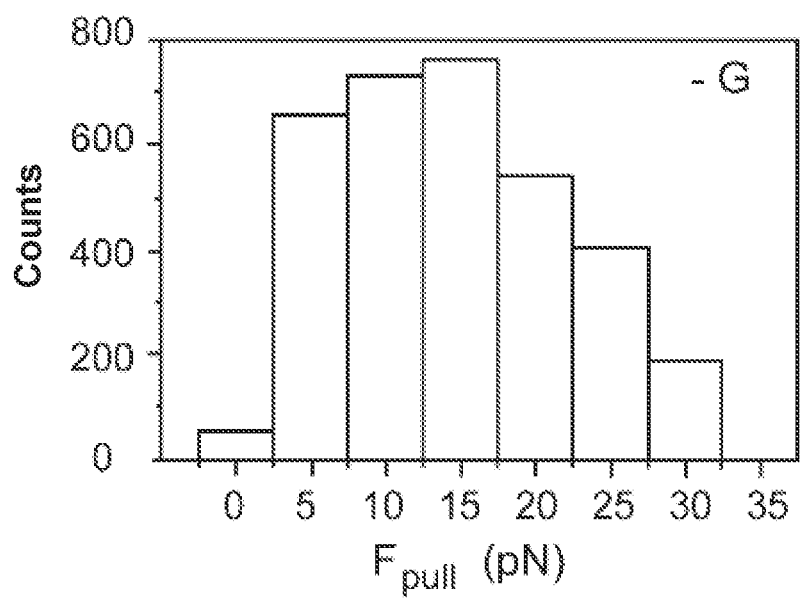
FIG. 18B is a force distribution in the absence of guanine (−G).

A dual-beam high-resolution optical tweezers was built that can detect short-lived fluctuations at sub-milliseconds (<0.25 msec) time scale at a single base pair level, with high precision and accuracy. This instrument was used to investigate the conformational dynamics of the full-length (FL) guanine-responsive riboswitch (guanine-riboswitch) and its 69-nt aptamer domain present in the 5'-UTR of an xpt-pbuX operon in B. subtilis. It has been shown that the xpt leader mRNA selectively downregulates the gene expression by transcription termination in the presence of guanine (FIG. 17B). The FL xpt mRNA was subjected to mechanical assays in order to identify the terminator and an anti-terminator conformation. FIG. 17C shows the characteristic force-extension curves (FECs) obtained by four successive pull/relax cycles in 1 µM guanine. The unfolding trajectory (red curve) indicated the melting of the 35-nt terminator hairpin at 16.1±0.5 pN (n=1200 traces) with a transition distance, $\Delta X_t \sim 15 \pm 3$ nm. A second transition at 17.9±0.9 pN with a distance, $\Delta X_a \sim 25$-30 nm indicated the unfolding of the 69-nt aptamer. Successive unfolding and refolding curves for both the FL and the aptamer riboswitch were reproducible indicating that the domains fold back into their initial native state following a complete rupture. The terminator mutant (FL-mutant, FIGS. 17D-E) abolished the 16.0 pN transition, thus supporting the structural assignment.

In 1 µM guanine, the isolated aptamer unfolded near 18.0 pN with extension, ~30 nm, which is similar to unfolding of the bound-aptamer (FIG. 17C) in context to the FL-RNA. This clearly supports that the FL-riboswitch unfolds sequentially in the presence of guanine: the terminator ruptures first followed by the aptamer.

Figure 19:
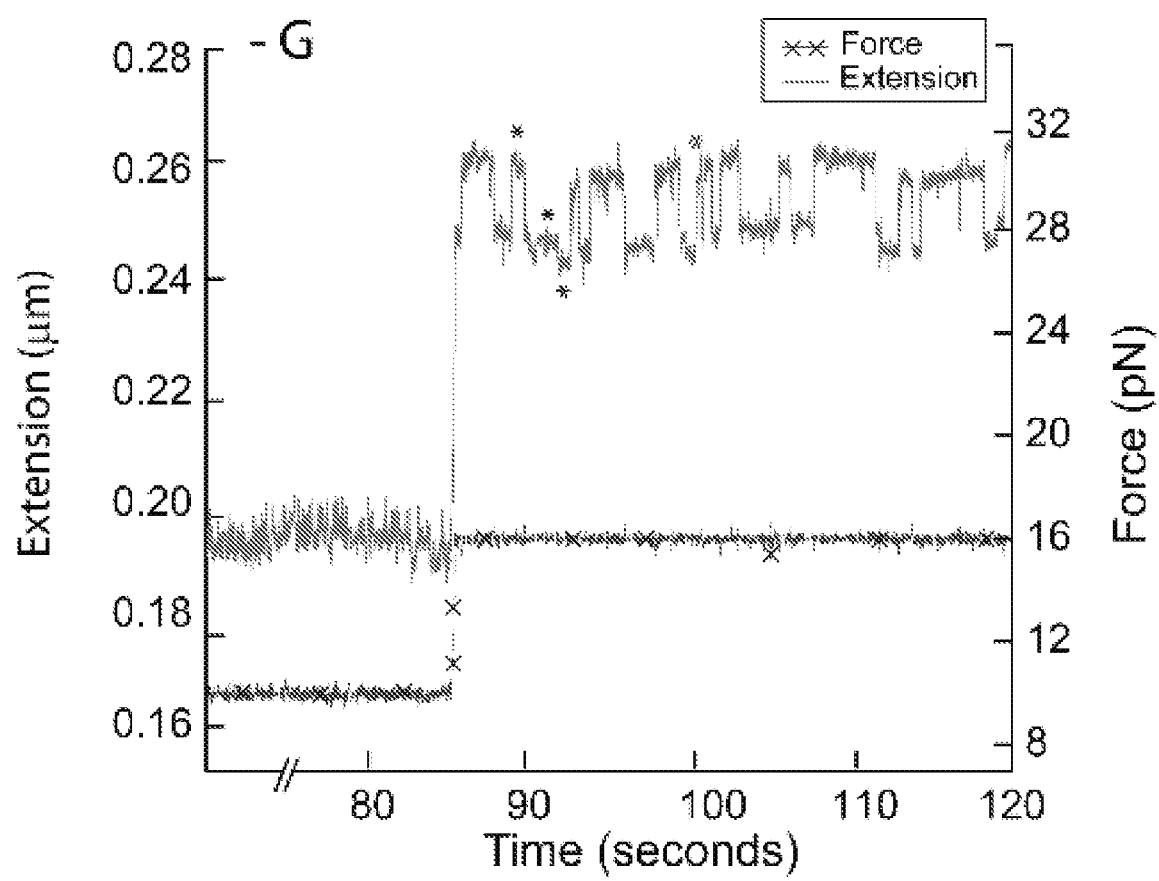
FIG. 19 is a chart that shows the full-length mutant RNA is a flexible structure in the absence of guanine.
Figure 20:
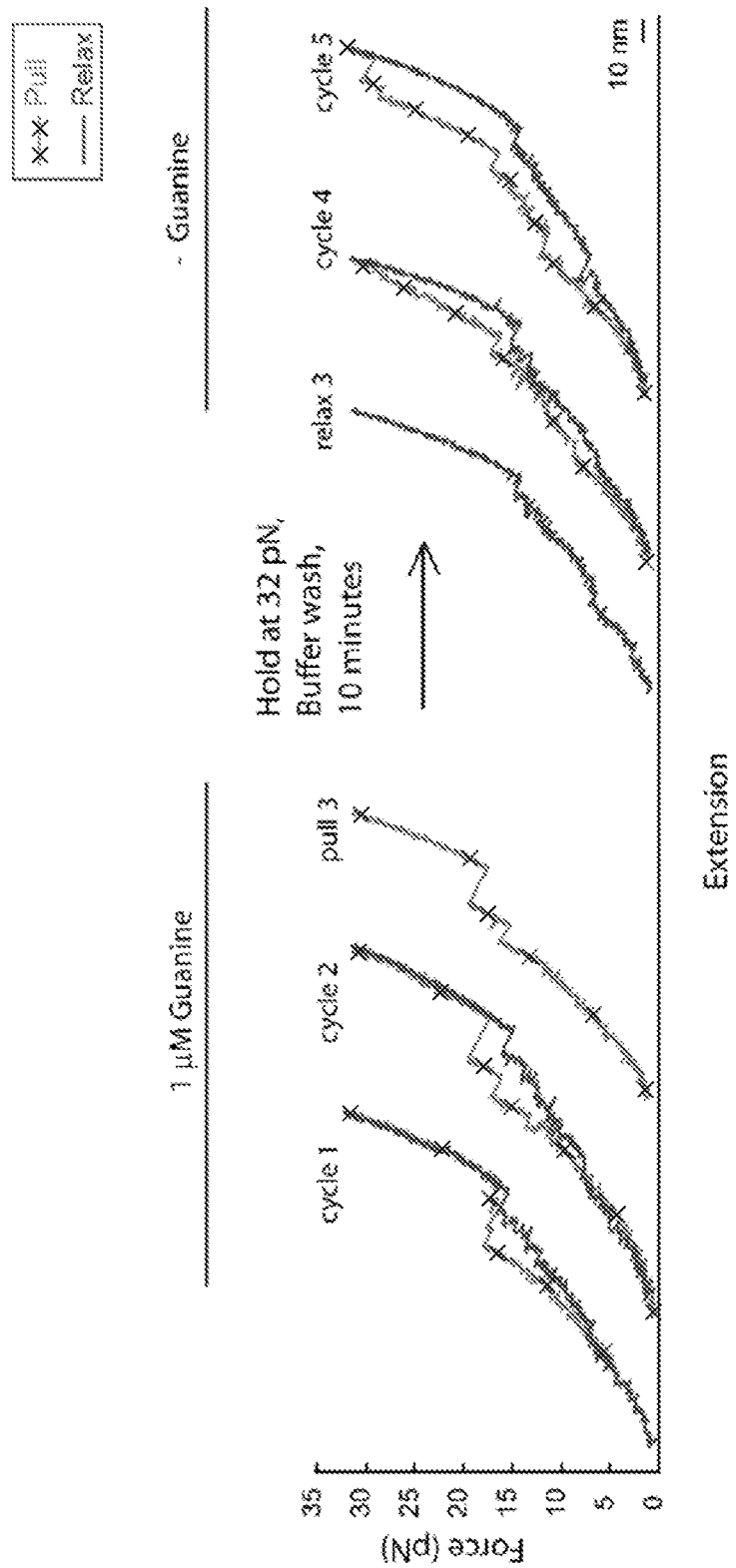
FIG. 20 shows force extension curves (FECs) demonstrating that guanine induces a unique structure to the full-length-xpt leader mRNA.
Figure 21:
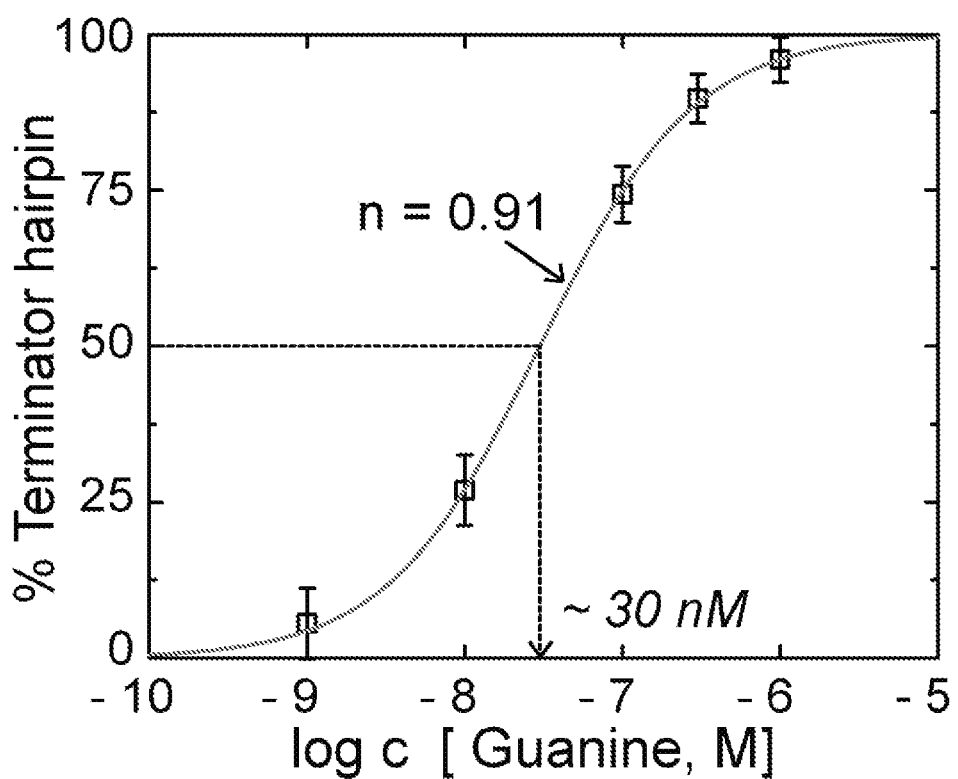
FIG. 21 is a chart showing percentage terminator hairpin (T) plotted as a function of guanine concentration.
Figure 22:
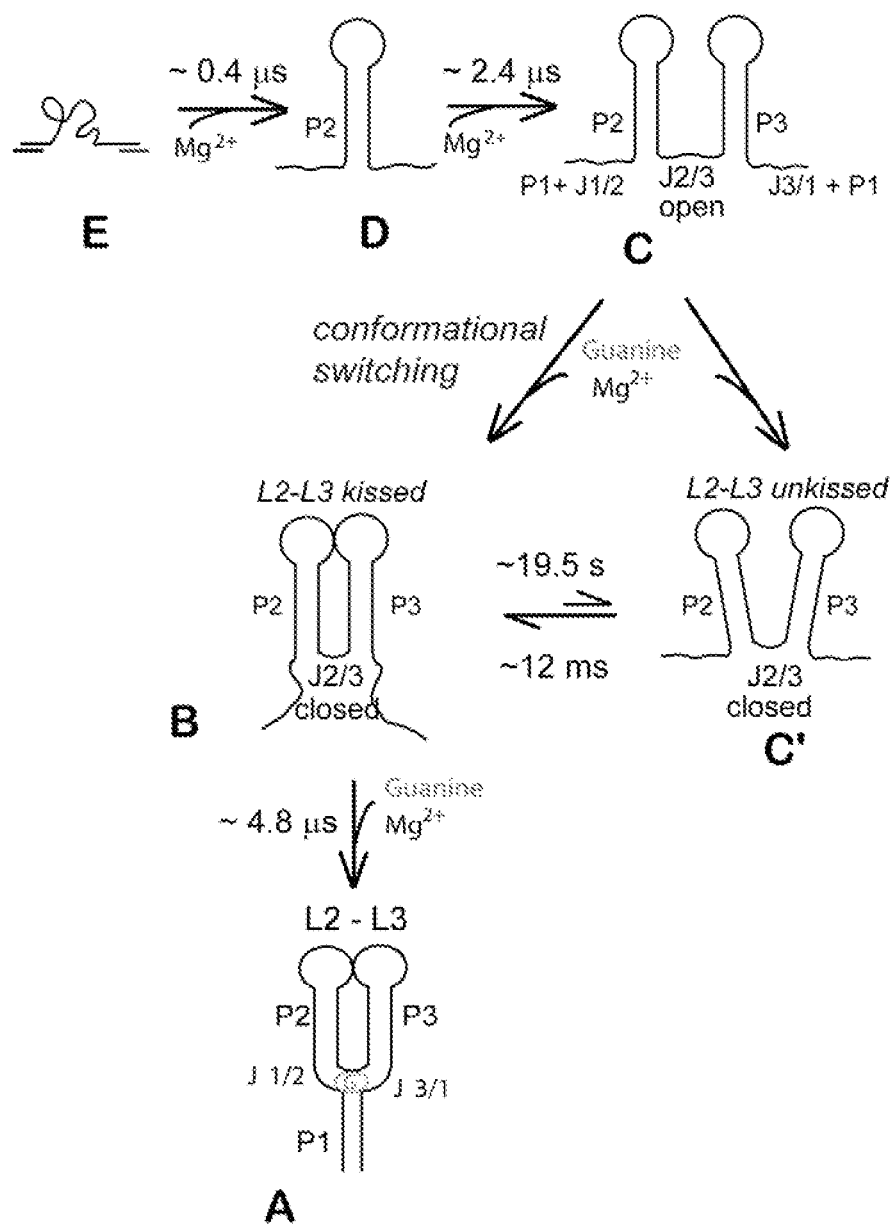
FIG. 22 shows time-resolved structural rearrangements in the aptamer folding.
Figure 23A:
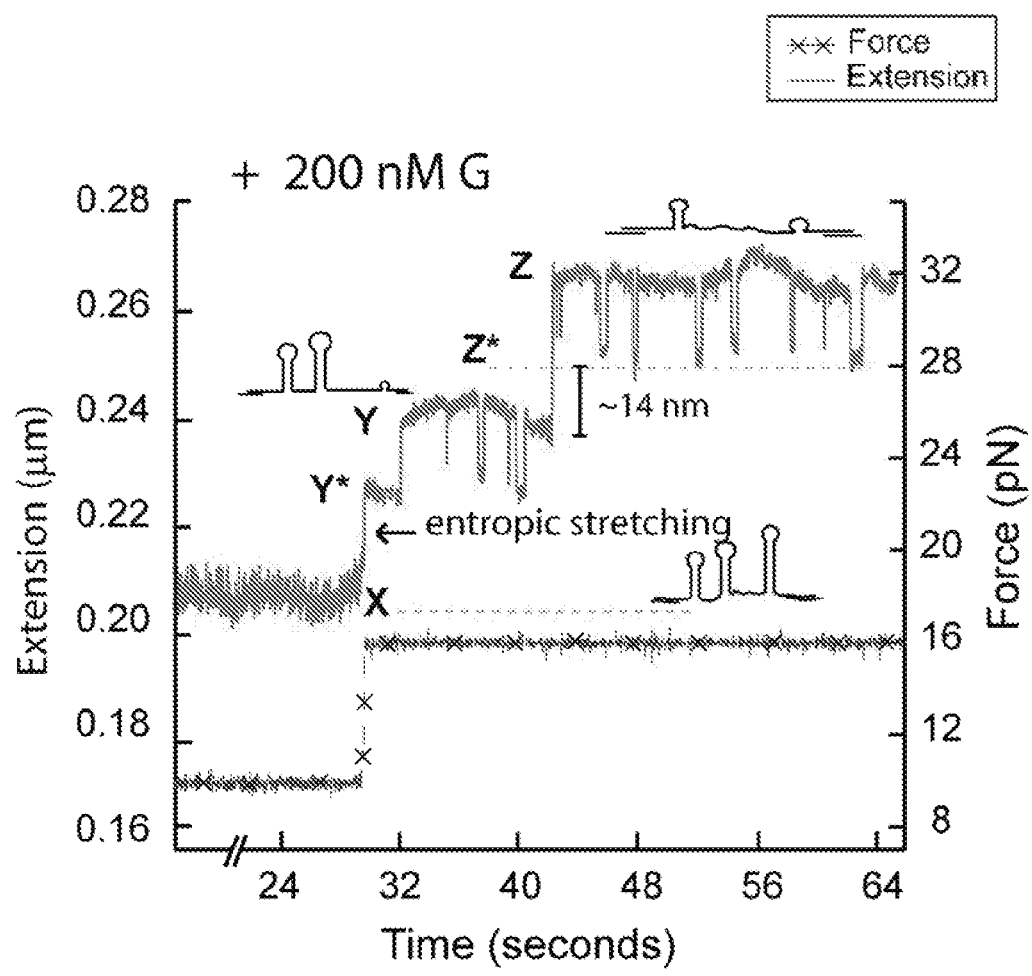
FIG. 23A shows a double Y-plot showing extension and force versus time for full-length (FL) wild-type guanine riboswitch RNA in 200 nM guanine.
Figure 23B:
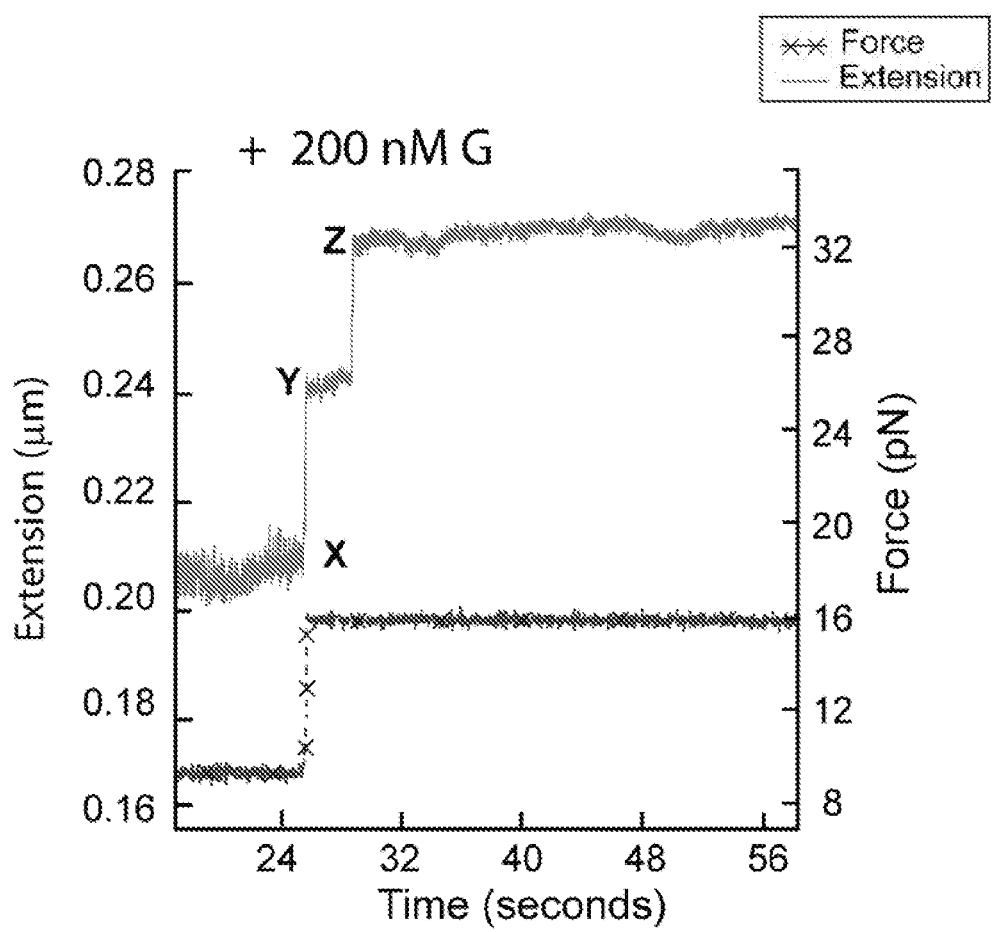
FIG. 23B shows a double Y-plot showing extension and force versus time for full-length (FL) mutant guanine riboswitch RNA in 200 nM guanine.
Figure 23C:
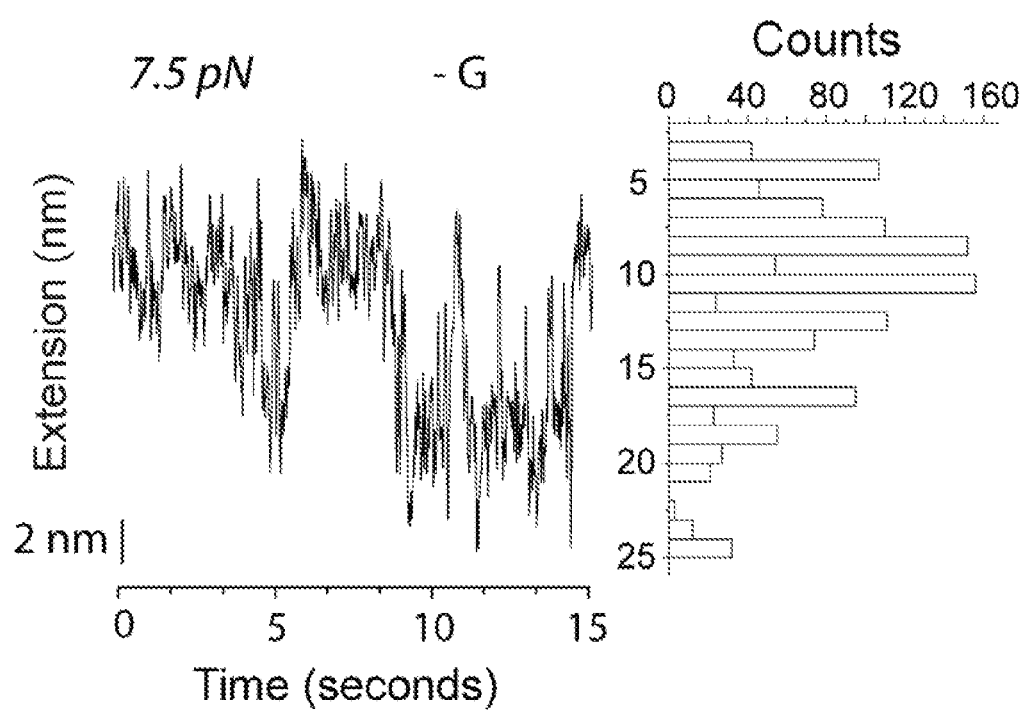
FIG. 23C is a plot showing extension versus time. The plot shows that in the absence of guanine, the aptamer hops with variable extensions indicating random short hairpin structures ranging from 3-25 nts.
Figure 24:
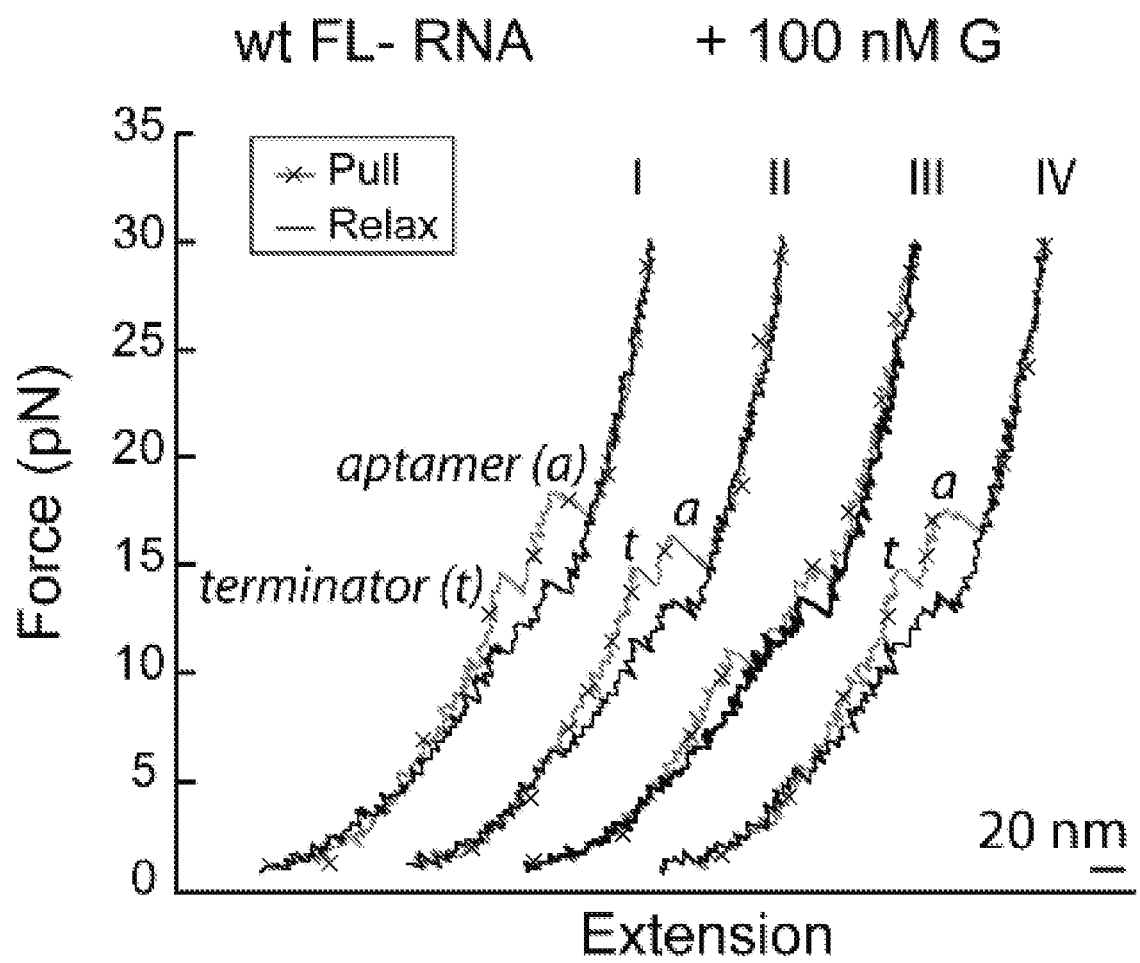
FIG. 24 shows force extension curves (FECs) for full-length (FL) wild-type guanine riboswitch RNA and the assignment of terminator structure for each of the force extension curves in low guanine concentrations.
Figure 25:
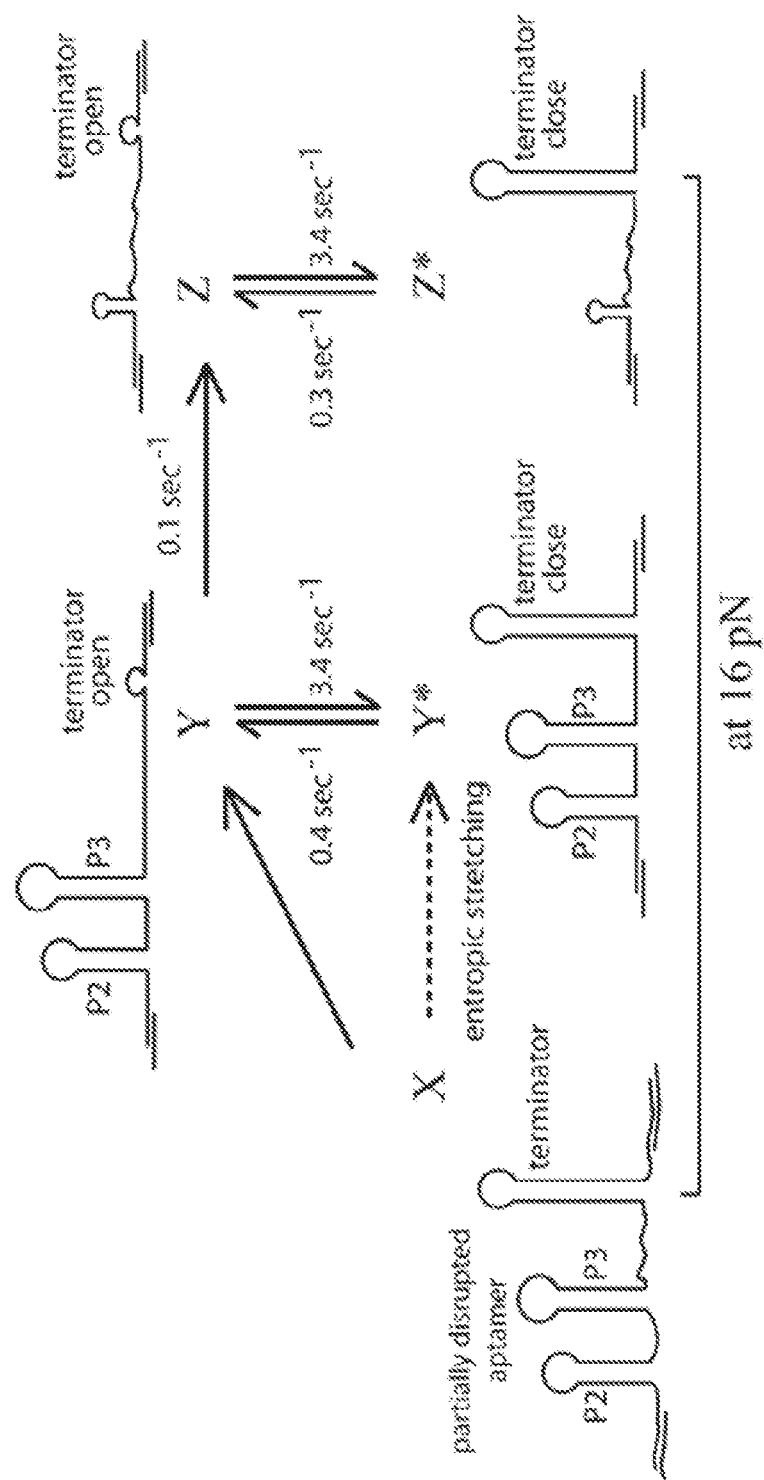
FIG. 25 shows a schematic representation of the unfolding pathways and kinetics in full-length (FL) wild-type guanine riboswitch RNA.
Figure 26:
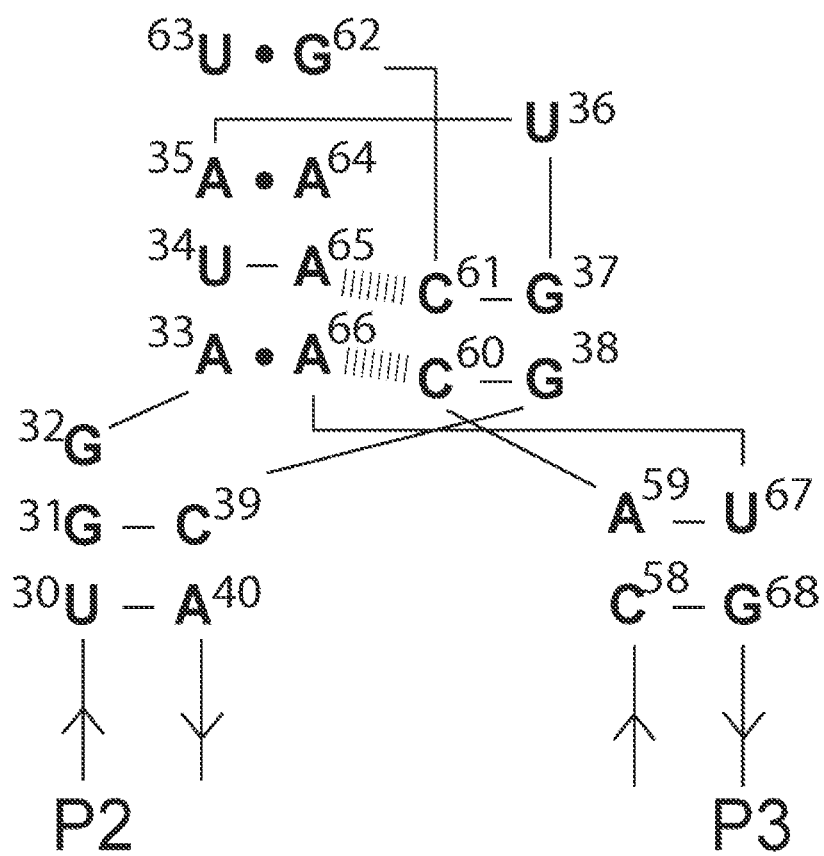
FIG. 26 shows a schematic representation of the L2-L3 hydrogen bonding in the wild-type guanine-aptamer following the crystal structure. Nucleotides 30-40 are included in the sequence of SEQ ID NO: 1. Nucleotides 58-68 are included in the sequence of SEQ ID NO: 1.
Figure 27A:
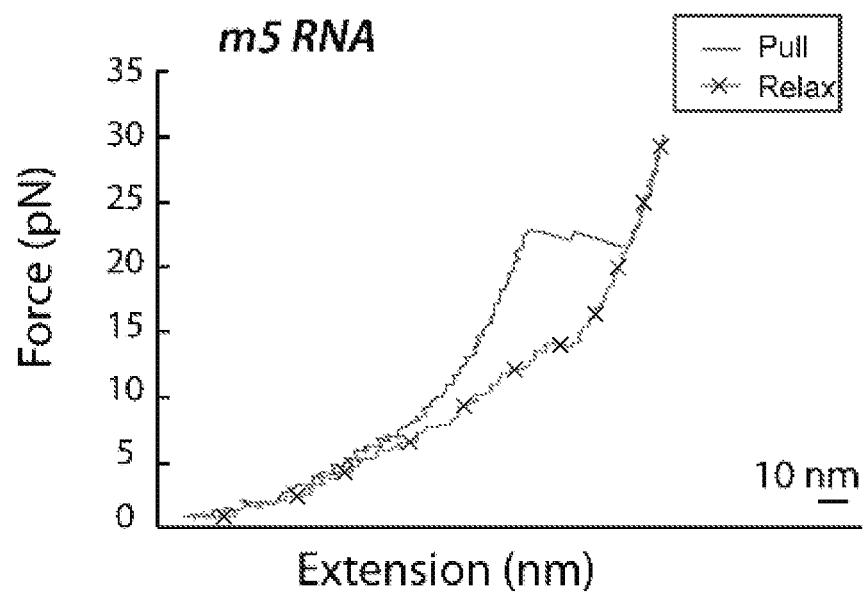
FIG. 27A shows a force extension curve for the m5 RNA in in +1 µM guanine.
Figure 27B:
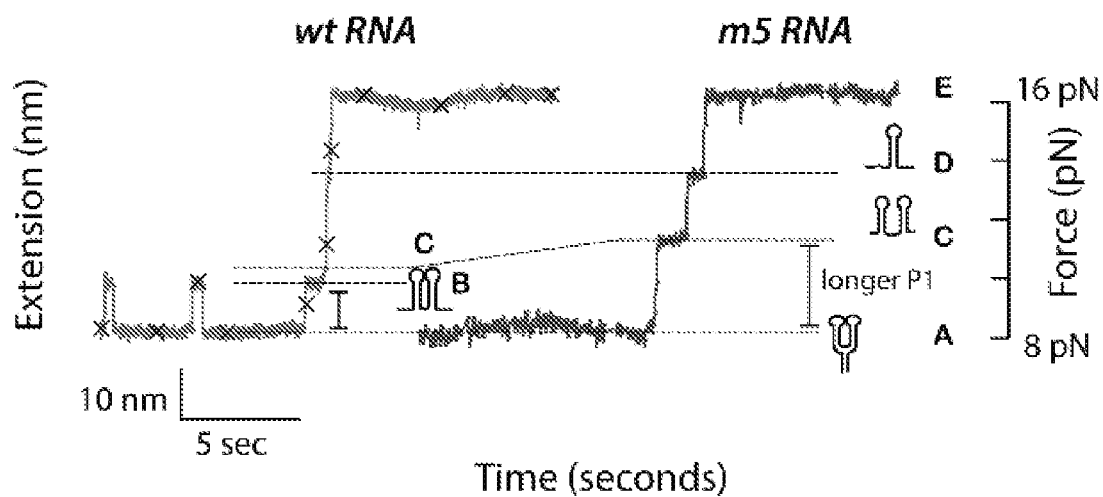
FIG. 27B shows a double Y-plot (force, extension vs. time) to compare the P1 behavior for the wild-type with the m5 RNA.

In the absence of guanine (–G), both the FL-RNA and the aptamer displayed random trajectories (FIGS. 17C, 3, and 5C-D), yielding a distributive force histogram (FIGS. 17C, 3, 5C-D, and 18A-B). Moreover, as the successive traces were not reproducible, the anti-terminator conformation could not be assigned to the transitions. In constant-force (CF) experiments, the FL-RNA showed variable extensions (FIG. 19), indicating that in the absence of guanine, the 5'-leader mRNA can adopt random hairpin structures. The function of the random structures can be presumed to destabilize the terminator hairpin and turn "ON" the gene expression. The un-bound trajectories are referred to as the "non-terminator" conformations to distinguish from the traditionally defined anti-terminator conformation. The same FL-RNA that exhibited the characteristic guanine-bound trajectory, failed to attain any specific conformation once the ligand was washed off the micro-chamber (FIG. 20). To assess the mode of allosteric modulation (tilt-equilibrium or induced-fit), the mechanical unfolding assay was performed in the presence of guanine salts ranging from 1 nM to 1 µM. The percentage terminator unfolding (FIG. 21) follows a 'S-shaped' curve to show that the expression platform changes from a random to a definitive hairpin conformation with increasing guanine. The terminator and the anti-terminator did not co-exist in low guanine, and therefore, the binding of the ligand cannot be described as simple partitioning between the two conformers. Had this been the case, a gradual shift would have been observed in the equilibrium toward the terminator conformation according to the tilt-equilibrium model. Instead, the data indicated that only the addition of the guanine induced a terminator structure from an ensemble of conformations by a modified induced-fit mechanism (FIG. 22). This was further ascertained in CF assay, wherein the expression platform displayed discrete terminator hopping kinetics in +G (FIG. 23A), against a flexible structure in the absence of guanine (FIG. 19). Thus, at 16 pN, the terminator fluctuates between the open and the closed states, observed as Y*↔Y and Z*↔Z in FIG. 23A. The bi-stabilities exhibited identical change in extension, 15±1.7 nm. The $K_{eq}$~0.1

$$\left(K(F) = \frac{\langle \tau_{B \to A} \rangle}{\langle \tau_{A \to B} \rangle} = \frac{k_{A \to B}}{k_{B \to A}} = \frac{k_F}{k_U}\right)$$

implied that the hairpin preferred the open state (90%) at 16 pN (the $K_{eq}$~1 at 15.6 pN). The expression platform dynamics and the unfolding scheme are shown in FIGS. 27A-B. That the bi-stabilities are due to the terminator was further confirmed by subjecting the FL-mutant to similar cycles (FIG. 23B). The RNA unfolded along X→Y→Z, without exhibiting a terminator hopping in 75 traces studied. The findings thus underscore that only the guanine induces a terminator conformation to the expression platform. Transition Y→Z* (ΔX=14±2.5 nm) indicated a complete unfolding of the aptamer (FIGS. 27A-B). Amongst 120 traces analyzed, Y→Z* never exhibited hopping at 16 pN, which would otherwise suggest a bi-stable aptamer.

Modified Induced-Fit Model

The aptamer was held at various constant-forces to investigate its folding dynamics. The tertiary interactions fold only after the secondary elements have formed. It was hypothesized that the barrier to the native receptor conformation must lie prior to the formation of the tertiary interactions.

Figure 28A:
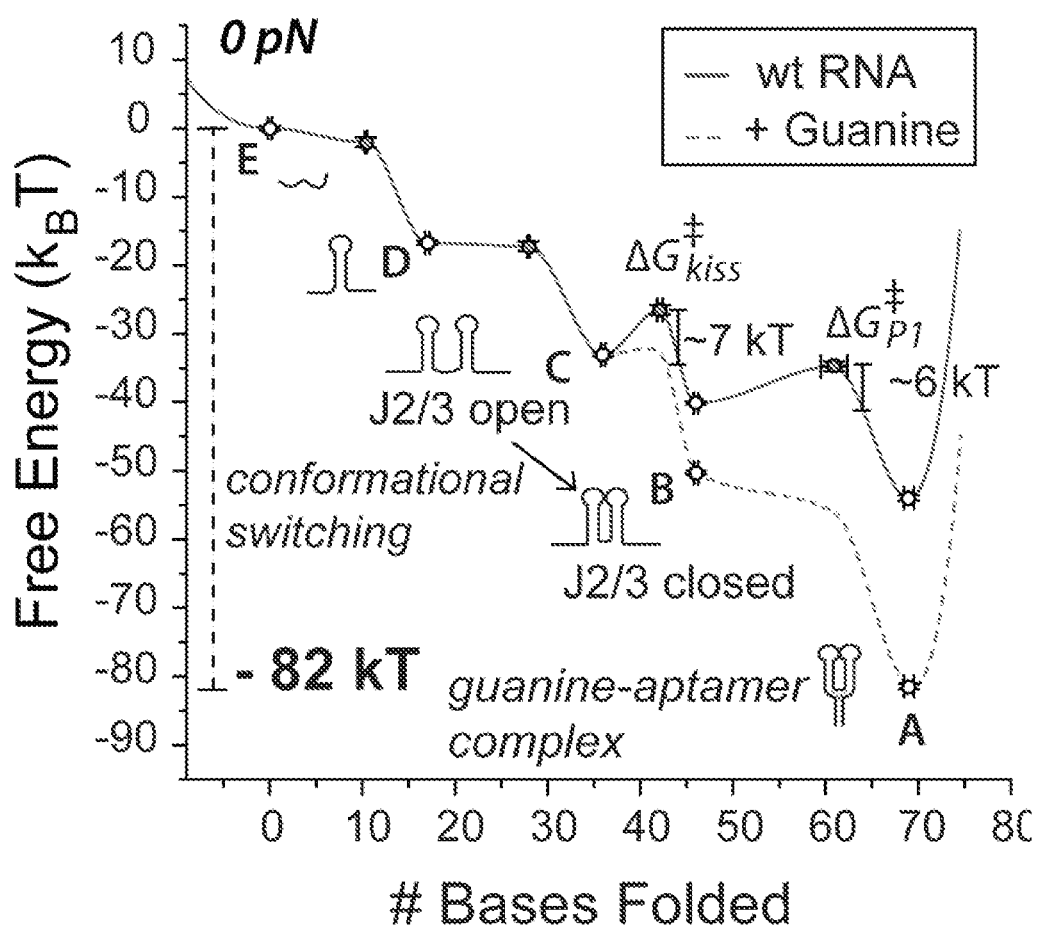
FIG. 28A shows the free energy landscape for wild-type RNA in the absence of force indicating two major barriers, $\Delta G_{Kiss}^{\ddagger}$ and $\Delta G_{P1}^{\ddagger}$.
Figure 28B:
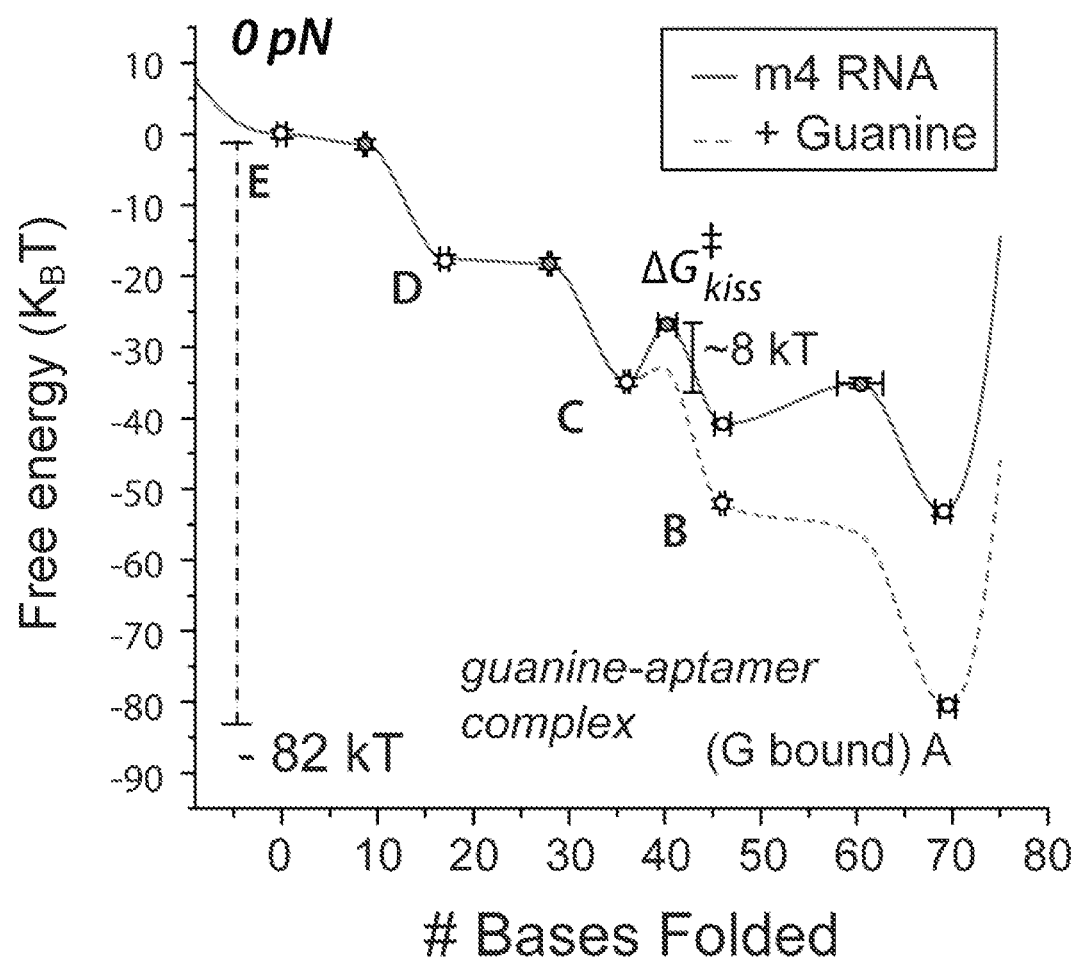
FIG. 28B shows the free energy landscape for m4 RNA in the absence of force indicating two major barriers, $\Delta G_{Kiss}^{\ddagger}$ and $\Delta G_{P1}^{\ddagger}$.

The barrier positions and the heights in the folding of the guanine-aptamer were measured. Based on the distance probability density (nm$^{-1}$), the equilibrium free energy landscape at 8.5 pN shows two barriers, $\Delta G_{kiss}^{\ddagger}$ and $\Delta G_{P1}^{\ddagger}$ (FIGS. 29A-D). A deconvolution procedure ($P^{k+1}(x) = P^k(x) + r (P^k(X)) \times [P^0(X) - PSF(X) \otimes P^k(X)]$ and $R(X) = P^0(X) - PSF(X) \otimes P^n(X)$) was used to extract the actual RNA fluctuations that are often masked by the experimental noises arising from the bead and the handles. The free energy landscape was then transformed to zero force (FIG. 28A, $\Delta G(X, F_2) - \Delta G(X, F_1) = -\int_{F_1}^{F_2} X(F) dF$). The plot clearly indicates that the riboswitch folding is downhill until state C, when P2 and P3 helices are formed. The subsequent folding is not straightforward. The RNA encounters the first barrier, $\Delta G_{kiss}^{\ddagger}$~7 $k_B$ T (or 4.2 kcal mol$^{-1}$) prior to the L2-L3 interactions. A second barrier is located before the folding of the P1-stem ($\Delta G_{P1}^{\ddagger}$~6 $k_B$T). The RNA cannot cross the barriers spontaneously by random fluctuations to form the receptor conformation. A modified induced-fit model was proposed, wherein the nascent RNA harnesses the binding energy ($\Delta G_{binding}$=−11.63±0.20 kcal/mol) to remodel the barriers, which triggers a conformational switching in the riboswitch core and followed by a series of structural rearrangements. The linker J2/3 acts as a molecular switch by undergoing a conformational change from an open to the closed state (C→B) upon binding guanine. The conformational rearrangement selectively positions the key residues in the end loops to facilitate the formation of the L2-L3 interactions. Once the long-range interactions are established, the junctions J1/2, J3/1 close around guanine and the P1 folds. The net free energy change $\Delta\Delta G_{aptamer}$=−81 kT favors the guanine-bound receptor structure (FIG. 28A). In m4 (FIG. 28B), a stable P3/L3 increases the height of the first barrier, $\Delta G_{kiss}^{\ddagger}$~8.4 kT that hinders in establishing the long-range interactions, and results in a slow P1-dynamics.

Figure 28C:
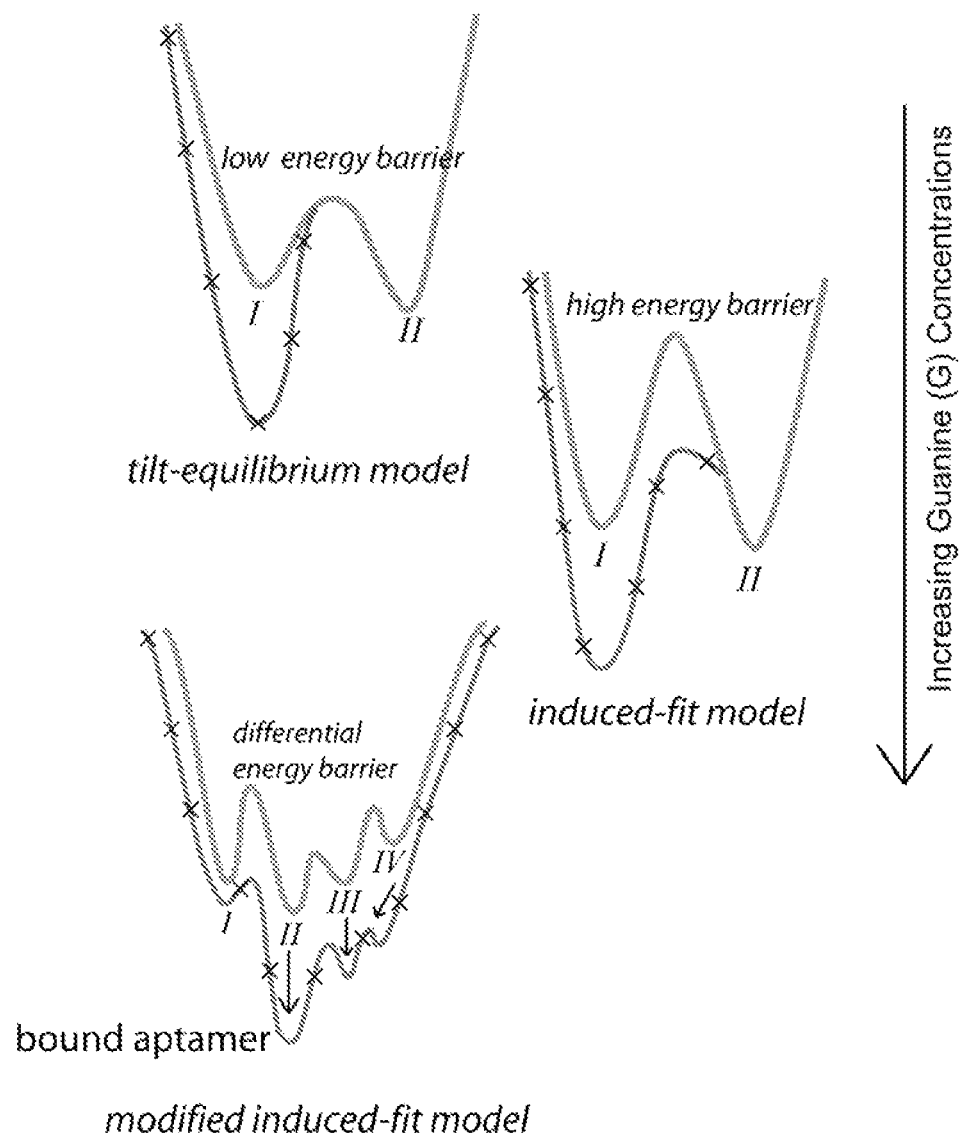
FIG. 28C shows a tilt-equilibrium model, a induced-fit model, and a modified-induced fit model.
Figure 29A:
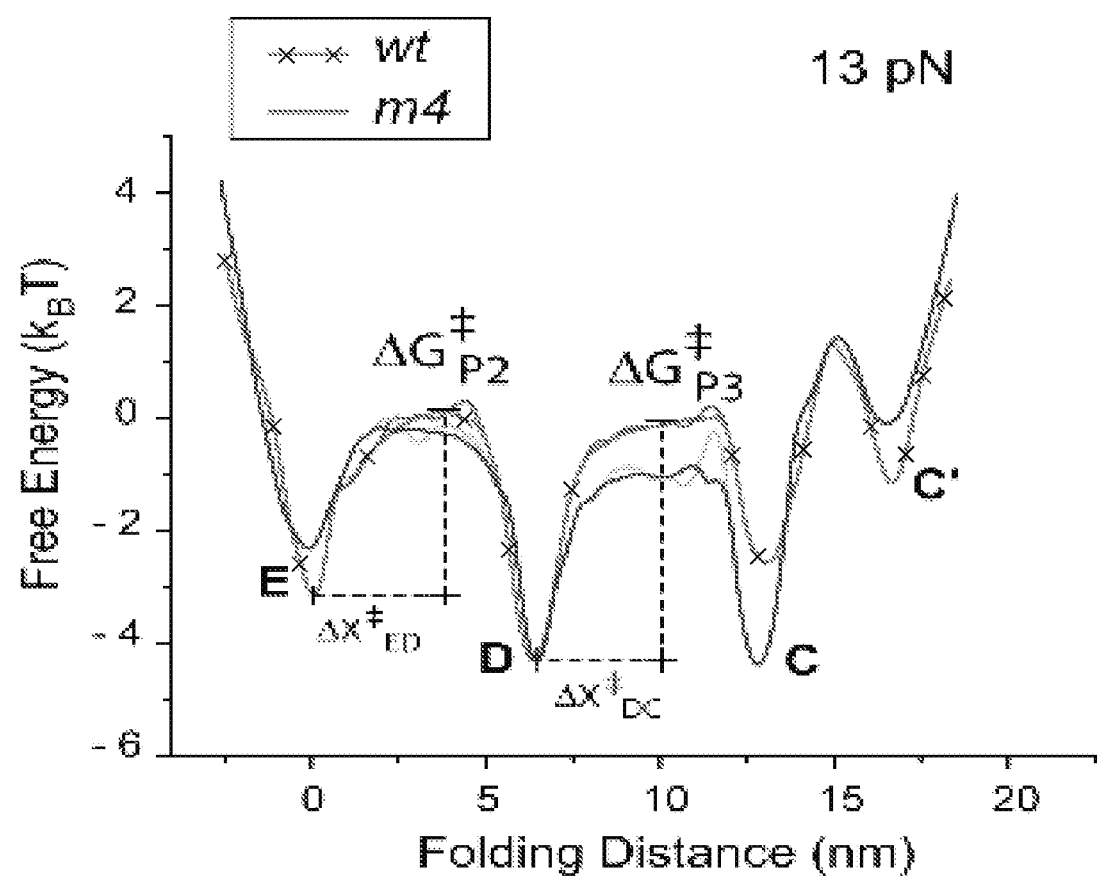
FIG. 29A shows the energy landscape for the wild-type RNA and the m4 RNA at 13 pN.
Figure 29B:
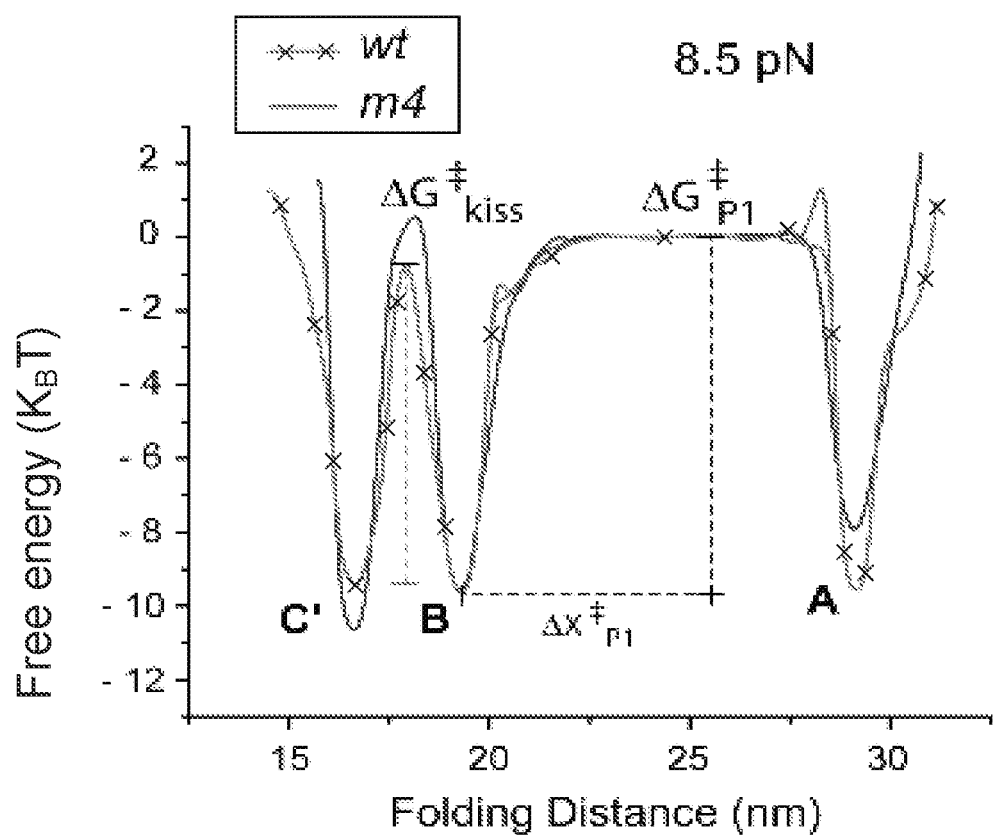
FIG. 29B shows the energy landscape for the wild-type RNA and the m4 RNA at 8.5 pN.
Figure 29C:
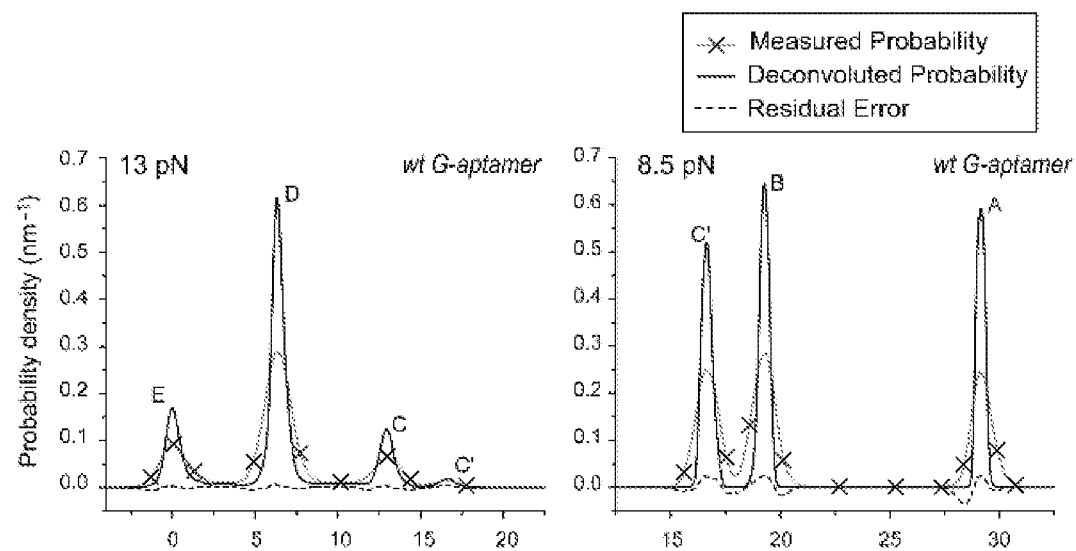
FIG. 29C shows the probability density distributions ($nm^{-1}$) for the wild-type aptamer.
Figure 29D:
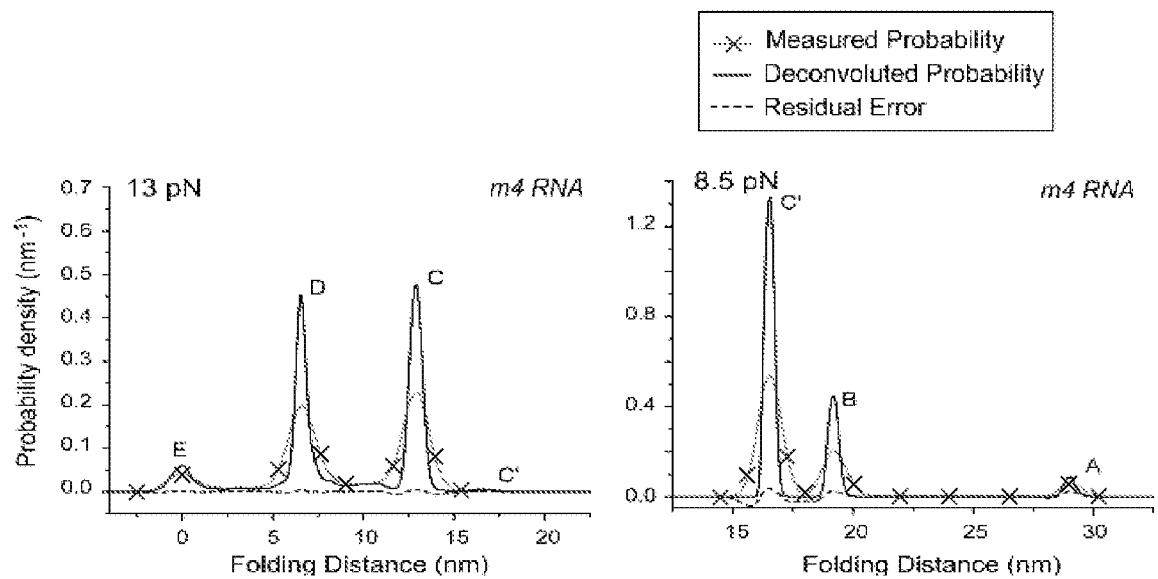
FIG. 29D shows the probability density distributions ($nm^{-1}$) for the m4 aptamer.
Figure 30:
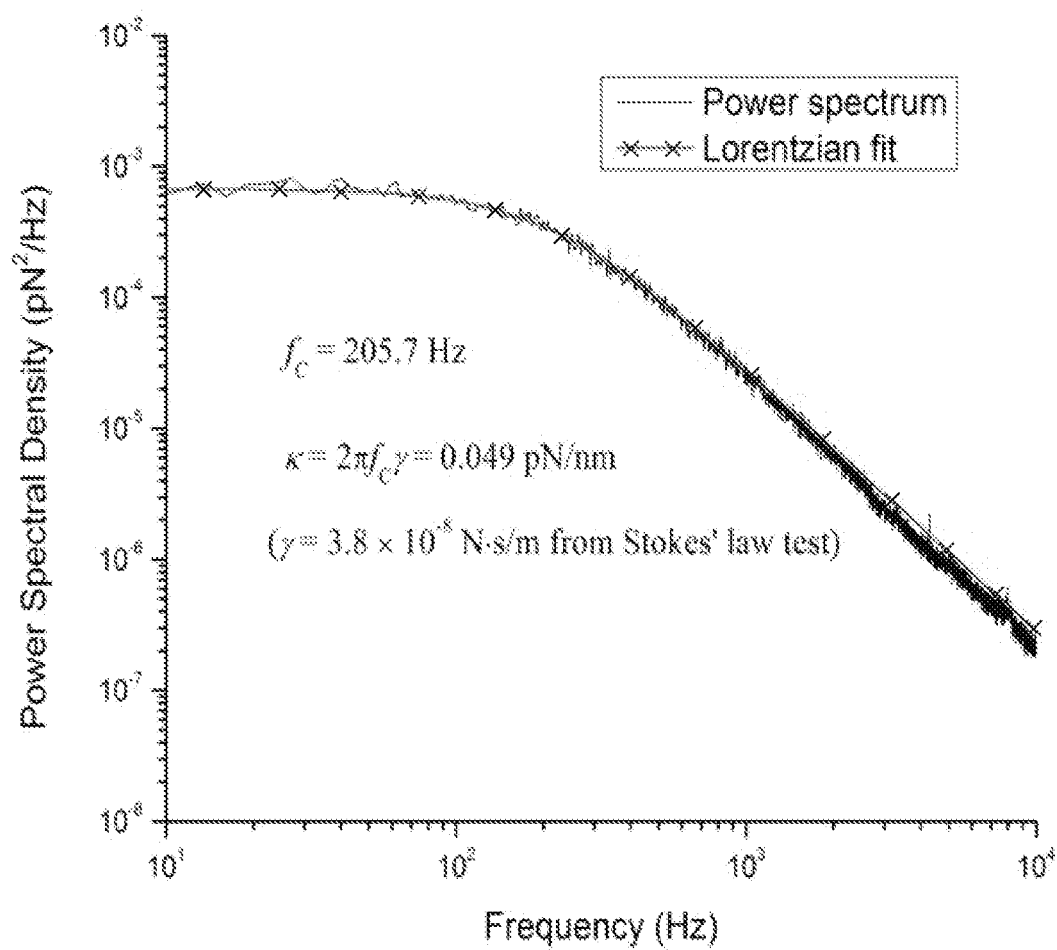
FIG. 30 shows power spectral density fitted with the Lorentzian fit to yield the corner frequency ($f_c$) that was used to calculate the trap stiffness.

By manipulating a single aptamer and the full length construct, it has been shown that the guanine-riboswitch domains exists in an ensemble of different structures, which do not resemble the terminator, anti-terminator or the aptamer conformation in the absence of guanine. It is possible that in this dynamic state, the conformers are separated by a distribution of energy barriers. Binding of the guanine remodeled at-least two such barriers in the guanine-riboswitch core to form the native receptor structure in ~8 μsec (FIG. 22). This model is, thus, not the traditional induced-fit (FIG. 28C), but a modified induced-fit model, which helps rationalize how the RNA structural rearrangements are coordinated with the transcriptional machinery in a timely fashion for gene regulation.

Method of Detecting a Biological Molecule in a Patient

Provided herein is a method of detecting a biological molecule in a patient, the method comprising: obtaining a biological sample from the patient; releasing the biological molecule from the biological sample, wherein the biological molecule comprises one or more riboswitch, wherein the one or more riboswitch comprises one or more aptamer domain; exposing the biological molecule comprising one or more riboswitch to a chemically modified ligand, wherein a binding of the chemically modified ligand to the biological molecule comprising one or more riboswitch is required for optical detection of the biological molecule comprising one or more riboswitch by fluorescence or absorbance; and detecting fluorescence of the chemically modified ligand bound to the biological molecule comprising one or more riboswitch after exposing the biological molecule comprising one or more riboswitch to the chemically modified ligand.

The term "exposing" refers to adding a ligand to any of the biological molecules disclosed herein in this application.

Provided herein is a method of detecting a biological molecule in a patient, the method comprising: releasing the biological molecule from a biological sample, wherein the biological molecule comprises one or more riboswitch, wherein the one or more riboswitch comprises one or more aptamer domain; exposing the biological molecule comprising one or more riboswitch to a chemically modified ligand, wherein a binding of the chemically modified ligand to the biological molecule comprising one or more riboswitch is required for optical detection of the biological molecule comprising one or more riboswitch by fluorescence or absorbance; and detecting fluorescence of the chemically modified ligand bound to the biological molecule comprising one or more riboswitch after exposing the biological molecule comprising one or more riboswitch to the chemically modified ligand.

The term "patient" includes humans and mammals. A patient can be a human suspected of having or having any disease or disorder. A patient can be a human suspected of having or having a bacterial, fungal, protozoan, or viral infection. A patient can be a human suspected of having or having a co-infection including two or more of bacteria, fungus, protozoa, and virus. A patient can be a human suspected of having or having cancer. A patient can be a human suspected of having or having a neurological condition or disorder. A patient can be a human suspected of having or having an immunological condition or disorder.

The biological sample can be blood, blood derivatives, urine, cerebro-spinal fluid, saliva, a tumor biospecimen, a tissue biospecimen, and combinations thereof. The biological sample can comprise a biological molecule.

The biological molecule can comprise one or more of: a bacterium, a virus, a fungus, a protozoan, and combinations thereof. The biological molecule can comprise deoxyribonucleic acid (DNA). The biological molecule can comprise ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more riboswitch. The one or more riboswitch can be one or more purine riboswitch. The one or more purine riboswitch can be one or more guanine riboswitch or one or more adenine riboswitch. The one or more riboswitch can be one or more mutated riboswitch not found in nature. The one or more riboswitch can be one or more mutated purine riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more riboswitch can comprise one or more aptamer domain. The one or more aptamer domain can be one or more mutated aptamer domain. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The chemically modified ligand can be a chemically modified purine, a chemically modified guanine, a chemically modified adenine, derivatives thereof, and combinations thereof.

The releasing step can comprise applying osmotic stress to the biological sample or using chemical and enzymatic methods on the biological sample.

The detecting step can comprise measuring the fluorescence of the chemically modified ligand bound to the biological molecule comprising one or more riboswitch to determine the concentration of the biological molecule comprising one or more riboswitch in the biological sample.

The method can further comprise the step of evaluating the concentration of the biological molecule comprising one or more riboswitch in the biological sample with respect to a threshold. The threshold can be the concentration of the biological molecule comprising one or more riboswitch in the biological sample of a human or mammal not having a disease or disorder. The threshold can be the concentration of the biological molecule comprising one or more riboswitch in the biological sample of a human or mammal not having a bacterial, fungal, protozoan, or viral infection. The threshold can be the concentration of the biological molecule comprising one or more riboswitch in the biological sample of a human or mammal not having a co-infection including two or more of bacteria, fungus, protozoa, and virus. The threshold can be the concentration of the biological molecule comprising one or more riboswitch in the biological sample of a human or mammal not having cancer. The threshold can be the concentration of the biological molecule comprising one or more riboswitch in the biological sample of a human or mammal not having a neurological condition or disorder. The threshold can be the concentration of the biological molecule comprising one or more riboswitch in the biological sample of a human or mammal not having an immunological condition or disorder.

The method can further comprise the step of prescribing a treatment to the patient if the concentration of the biological molecule comprising one or more riboswitch in the biological sample exceeds the threshold. The method can further comprise the step of prescribing a treatment to the patient if the concentration of the biological molecule comprising one or more riboswitch in the biological sample is less than the threshold.

The method can further comprise the step of detecting the fluorescence of the chemically modified ligand before exposing the biological molecule comprising one or more riboswitch to the chemically modified ligand.

The method can further comprise the step of detecting the fluorescence of the chemically modified ligand before exposing the biological molecule comprising one or more mutated riboswitch to the chemically modified ligand, wherein the one or more mutated riboswitch comprises SEQ ID NO: 13.

The method can further comprise the step of detecting the fluorescence of the chemically modified ligand before exposing the biological molecule comprising one or more riboswitch comprising one or more mutated aptamer domain to the chemically modified ligand, wherein the one or more mutated aptamer domain comprises a sequence selected from the group consisting of SEQ ID NOs: 2-9 and combinations thereof.

The method can further comprise a fluorimeter configured to detect said fluorescence or other suitable unit or instrument to detect optically relevant signals. The fluorimeter can comprise a filter fluorimeter. The fluorimeter can comprise a spectrofluorimeter.

Method of Detecting a Biological Molecule

Provided herein is a method of detecting a biological molecule, the method comprising: obtaining a biological sample; releasing the biological molecule from the biological sample, wherein the biological molecule comprises one or more riboswitch, wherein the one or more riboswitch comprises one or more aptamer domain; exposing the biological molecule comprising one or more riboswitch to a chemically modified ligand, wherein a binding of the chemically modified ligand to the biological molecule comprising one or more riboswitch is required for optical detection of the biological molecule comprising one or more riboswitch by fluorescence or absorbance; and detecting fluorescence of the chemically modified ligand bound to the biological molecule comprising one or more riboswitch after exposing the biological molecule comprising one or more riboswitch to the chemically modified ligand.

Provided herein is a method of detecting a biological molecule, the method comprising: releasing the biological molecule from a biological sample, wherein the biological molecule comprises one or more riboswitch, wherein the one or more riboswitch comprises one or more aptamer domain; exposing the biological molecule comprising one or more riboswitch to a chemically modified ligand, wherein a binding of the chemically modified ligand to the biological molecule comprising one or more riboswitch is required for optical detection of the biological molecule comprising one or more riboswitch by fluorescence or absorbance; and detecting fluorescence of the chemically modified ligand bound to the biological molecule comprising one or more riboswitch after exposing the biological molecule comprising one or more riboswitch to the chemically modified ligand.

The biological sample can be contaminated water, contaminated food, contaminated liquid, contaminated solid, and combinations thereof. The biological sample can be a contaminated water sample or contaminated food sample. The biological sample can comprise a biological molecule.

The biological molecule can comprise one or more of: a bacterium, a virus, a fungus, a protozoan, and combinations thereof. The biological molecule can comprise deoxyribonucleic acid (DNA). The biological molecule can comprise ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more riboswitch. The one or more riboswitch can be one or more purine riboswitch. The one or more purine riboswitch can be one or more guanine riboswitch or one or more adenine riboswitch. The one or more riboswitch can be one or more mutated riboswitch not found in nature. The one or more riboswitch can be one or more mutated purine riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more riboswitch can comprise one or more aptamer domain. The one or more aptamer domain can be one or more mutated aptamer domain. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The chemically modified ligand can be a chemically modified purine, a chemically modified guanine, a chemically modified adenine, derivatives thereof, and combinations thereof.

The releasing step can comprise applying osmotic stress to the biological sample or using chemical and enzymatic methods on the biological sample.

The detecting step can comprise measuring the fluorescence of the chemically modified ligand bound to the biological molecule comprising one or more riboswitch to determine the concentration of the biological molecule comprising one or more riboswitch in the biological sample.

The method can further comprise the step of evaluating the concentration of the biological molecule comprising one or more riboswitch in the biological sample with respect to a threshold. The threshold can be the concentration of the biological molecule comprising one or more riboswitch in a biological sample that is uncontaminated water. The threshold can be the concentration of the biological molecule comprising one or more riboswitch in a biological sample that is uncontaminated food. The threshold can be the concentration of the biological molecule comprising one or more riboswitch in a biological sample that is uncontaminated liquid. The threshold can be the concentration of the biological molecule comprising one or more riboswitch in a biological sample that is uncontaminated solid.

The method can further comprise the step of detecting the fluorescence of the chemically modified ligand before exposing the biological molecule comprising one or more riboswitch to the chemically modified ligand.

The method can further comprising the step of detecting the fluorescence of the chemically modified ligand before exposing the biological molecule comprising one or more riboswitch comprising one or more mutated aptamer domain to the chemically modified ligand, wherein the one or more mutated aptamer domain comprises a sequence selected from the group consisting of SEQ ID NOs: 2-9 and combinations thereof.

The method can further comprise a fluorimeter configured to detect said fluorescence or other suitable unit or instrument to detect optically relevant signals. The fluorimeter can comprise a filter fluorimeter. The fluorimeter can comprise a spectrofluorimeter.

Method of Detecting a Biological Molecule in a Patient

Provided herein is a method of detecting a biological molecule in a patient, the method comprising: obtaining a biological sample from the patient; releasing the biological molecule from the biological sample; exposing the biological molecule to a chemically modified ligand, wherein the chemically modified ligand comprises one or more riboswitch comprising one or more aptamer domain, wherein a binding of the chemically modified ligand comprising one or more riboswitch to the biological molecule is required for optical detection of the biological molecule by fluorescence or absorbance; and detecting fluorescence of the chemically modified ligand comprising one or more riboswitch bound to the biological molecule after exposing the biological molecule to the chemically modified ligand comprising one or more riboswitch.

Provided herein is a method of detecting a biological molecule in a patient, the method comprising: releasing the biological molecule from a biological sample; exposing the biological molecule to a chemically modified ligand, wherein the chemically modified ligand comprises one or more riboswitch comprising one or more aptamer domain, wherein a binding of the chemically modified ligand comprising one or more riboswitch to the biological molecule is required for optical detection of the biological molecule by fluorescence or absorbance; and detecting fluorescence of the chemically modified ligand comprising one or more riboswitch bound to the biological molecule after exposing the biological molecule to the chemically modified ligand comprising one or more riboswitch.

The biological sample can be blood, blood derivatives, urine, cerebro-spinal fluid, saliva, a tumor biospecimen, a tissue biospecimen, and combinations thereof. The biological sample can comprise a biological molecule.

The biological molecule can comprise one or more of: a bacterium, a virus, a fungus, a protozoan, and combinations thereof. The biological molecule can comprise deoxyribonucleic acid (DNA). The biological molecule can comprise ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate. The biological molecule can comprise one or more metabolite or ligand capable of binding to the one or more aptamer domain located in the one or more riboswitch of the chemically modified ligand.

The chemically modified ligand can comprise one or more riboswitch. The one or more riboswitch can be one or more purine riboswitch. The one or more purine riboswitch can be one or more guanine riboswitch or one or more adenine riboswitch. The one or more riboswitch can be one or more mutated riboswitch not found in nature. The one or more riboswitch can be one or more mutated purine riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more riboswitch can comprise one or more aptamer domain. The one or more aptamer domain can be one or more mutated aptamer domain. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The releasing step can comprise applying osmotic stress to the biological sample or using chemical and enzymatic methods on the biological sample.

The detecting step can comprise measuring the fluorescence of the chemically modified ligand comprising one or more riboswitch bound to the biological molecule to determine the concentration of the biological molecule in the biological sample.

The method can further comprise the step of evaluating the concentration of the biological molecule in the biological sample with respect to a threshold. The threshold can be the concentration of the biological molecule in the biological sample of a human or mammal not having a disease or disorder. The threshold can be the concentration of the biological molecule in the biological sample of a human or mammal not having a bacterial, fungal, protozoan, or viral infection. The threshold can be the concentration of the biological molecule in the biological sample of a human or mammal not having a co-infection including two or more of bacteria, fungus, protozoa, and virus. The threshold can be the concentration of the biological molecule in the biological sample of a human or mammal not having cancer. The threshold can be the concentration of the biological molecule in the biological sample of a human or mammal not having a neurological condition or disorder. The threshold can be the concentration of the biological molecule in the biological sample of a human or mammal not having an immunological condition or disorder.

The method can further comprise the step of prescribing a treatment to the patient if the concentration of the biological molecule in the biological sample exceeds the threshold. The method can further comprise the step of prescribing a treatment to the patient if the concentration of the biological molecule in the biological sample is less than the threshold.

The method can further comprise the step of detecting the fluorescence of the chemically modified ligand comprising one or more riboswitch before exposing the biological molecule to the chemically modified ligand.

The method can further comprise the step of detecting the fluorescence of the chemically modified ligand comprising one or more mutated riboswitch before exposing the biological molecule to the chemically modified ligand, wherein the one or more mutated riboswitch comprises SEQ ID NO: 13.

The method can further comprising the step of detecting the fluorescence of the chemically modified ligand comprising one or more riboswitch comprising one or more mutated aptamer domain before exposing the biological molecule to the chemically modified ligand, wherein the one or more mutated aptamer domain comprises a sequence selected from the group consisting of SEQ ID NOs: 2-9 and combinations thereof.

The method can further comprise a fluorimeter configured to detect said fluorescence or other suitable unit or instrument to detect optically relevant signals. The fluorimeter can comprise a filter fluorimeter. The fluorimeter can comprise a spectrofluorimeter.

Method of Detecting a Biological Molecule

Provided herein is a method of detecting a biological molecule, the method comprising: obtaining a biological sample; releasing the biological molecule from the biological sample; exposing the biological molecule to a chemically modified ligand, wherein the chemically modified ligand comprises one or more riboswitch comprising one or more aptamer domain, wherein a binding of the chemically modified ligand comprising one or more riboswitch to the biological molecule is required for optical detection of the biological molecule by fluorescence or absorbance; and detecting fluorescence of the chemically modified ligand comprising one or more riboswitch bound to the biological molecule after exposing the biological molecule to the chemically modified ligand comprising one or more riboswitch.

Provided herein is a method of detecting a biological molecule, the method comprising: releasing the biological molecule from a biological sample; exposing the biological molecule to a chemically modified ligand, wherein the chemically modified ligand comprises one or more riboswitch comprising one or more aptamer domain, wherein a binding of the chemically modified ligand comprising one or more riboswitch to the biological molecule is required for optical detection of the biological molecule by fluorescence or absorbance; and detecting fluorescence of the chemically modified ligand comprising one or more riboswitch bound to the biological molecule after exposing the biological molecule to the chemically modified ligand comprising one or more riboswitch.

The biological sample can be contaminated water, contaminated food, contaminated liquid, contaminated solid, and combinations thereof. The biological sample can be a contaminated water sample or contaminated food sample. The biological sample can comprise a biological molecule.

The biological molecule can comprise one or more of: a bacterium, a virus, a fungus, a protozoan, and combinations thereof. The biological molecule can comprise deoxyribonucleic acid (DNA). The biological molecule can comprise ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate. The biological molecule can comprise one or more metabolite or ligand capable of binding to the one or more aptamer domain located in the one or more riboswitch of the chemically modified ligand.

The chemically modified ligand can comprise one or more riboswitch. The one or more riboswitch can be one or more purine riboswitch. The one or more purine riboswitch can be one or more guanine riboswitch or one or more adenine riboswitch. The one or more riboswitch can be one or more mutated riboswitch not found in nature. The one or more riboswitch can be one or more mutated purine riboswitch not found in nature. The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The one or more riboswitch can comprise one or more aptamer domain. The one or more aptamer domain can be one or more mutated aptamer domain not found in nature. The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The releasing step can comprise applying osmotic stress to the biological sample or using chemical and enzymatic methods on the biological sample.

The detecting step can comprise measuring the fluorescence of the chemically modified ligand comprising one or more riboswitch bound to the biological molecule to determine the concentration of the biological molecule in the biological sample.

The method can further comprise the step of evaluating the concentration of the biological molecule in the biological sample with respect to a threshold. The threshold can be based on the concentration of the biological molecule in uncontaminated water. The threshold can be based on the concentration of the biological molecule in uncontaminated food. The threshold can be based on the concentration of the biological molecule in uncontaminated liquid. The threshold can be based on the concentration of the biological molecule in uncontaminated solid.

The method can further comprise the step of prescribing a treatment to the patient if the concentration of the biological molecule in the biological sample exceeds the threshold. The method can further comprise the step of prescribing a treatment to the patient if the concentration of the biological molecule in the biological sample is less than the threshold.

The method can further comprise the step of detecting the fluorescence of the chemically modified ligand comprising one or more riboswitch before exposing the biological molecule to the chemically modified ligand.

The method can further comprise the step of detecting the fluorescence of the chemically modified ligand comprising one or more mutated riboswitch before exposing the biological molecule to the chemically modified ligand, wherein the one or more mutated riboswitch comprises SEQ ID NO: 13.

The method can further comprising the step of detecting the fluorescence of the chemically modified ligand comprising one or more riboswitch comprising one or more mutated aptamer domain before exposing the biological molecule to the chemically modified ligand, wherein the one or more mutated aptamer domain comprises a sequence selected from the group consisting of SEQ ID NOs: 2-9 and combinations thereof.

The method can further comprise a fluorimeter configured to detect said fluorescence or other suitable unit or instrument to detect optically relevant signals. The fluorimeter can comprise a filter fluorimeter. The fluorimeter can comprise a spectrofluorimeter.

Biological Sensor

The term "biological sensor" refers to eukaryotic cells or prokaryotic cells comprising one or more biological molecule not found in nature. The one or more biological molecule not found in nature can comprise one or more riboswitch or one or more mutated riboswitch. The one or more biological molecule not found in nature can comprise one or more aptamer domain or one or more mutated aptamer domain. The biological sensor can comprise one or more ligand capable of binding to the one or more aptamer domain or one or more mutated apatmer domain.

Provided herein is a biological sensor comprising: a biological molecule not found in nature comprising one or more aptamer domain, wherein the one or more aptamer domain comprises: one or more hairpin; one or more loop; and one or more junction. The biological sensor also comprises one or more ligand capable of binding to the one or more aptamer domain, wherein the one or more ligand binds the one or more aptamer domain switching the one or more aptamer domain between one or more structural conformations.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more aptamer domain. The one or more aptamer domain can be one or more purine aptamer domain. The one or more purine aptamer domain can be one or more guanine aptamer domain or one or more adenine aptamer domain.

The one or more aptamer domain can comprise: one or more hairpin; one or more loop; and one or more junction. The one or more hairpin can be P1, P2, or P3. The one or more loop can be L2 or L3. The one or more junction can be J1/2, J2/3, and J3/1. The one or more hairpin, one or more loop, and one or more junction can be modified in length, size, sequence, chemical functional groups, or combinations thereof.

The one or more aptamer domain can form one or more structural conformations, such as a P2 helix conformation, a P2-P3 helix conformation, a L2-L3 unkissed conformation, a L2-L3 kissed conformation, and a guanine-bound conformation.

Provided herein is a microchip comprising the biological sensors described herein. The microchip can comprise eukaryotic cells acting as biological sensors. The microchip can comprise prokaryotic cells acting as biological sensors.

Biological Sensor (Faster Rate of Switching)

Provided herein is a biological sensor comprising: a biological molecule not found in nature comprising one or more mutated aptamer domain, wherein the one or more mutated aptamer domain comprises: one or more hairpin; one or more loop; and one or more junction. The biological sensor also comprises one or more ligand capable of binding to the one or more mutated aptamer domain, wherein the one or more ligand binds the one or more mutated aptamer domain switching the one or more mutated aptamer domain between one or more structural conformations. A rate in which the one or more mutant aptamer domain switches between the one or more structural conformations is faster than a rate in which one or more wild-type aptamer domain switches between the one or more structural conformations.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more mutated aptamer domain. The one or more mutated aptamer domain can be one or more mutated purine aptamer domain. The one or more mutated purine aptamer domain can be one or more mutated guanine aptamer domain or one or more mutated adenine aptamer domain.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The one or more mutated aptamer domain can comprise: one or more hairpin; one or more loop; and one or more junction. The one or more hairpin can be P1, P2, or P3. The one or more loop can be L2 or L3. The one or more junction can be J1/2, J2/3, and J3/1. The one or more hairpin, one or more loop, and one or more junction can be modified in length, size, sequence, chemical functional groups, or combinations thereof.

One or more of the P1, P2, and P3 can comprise a base pair mutation. For example, the P1 can comprise a sequence selected from the group consisting of: SEQ ID NOs: 10-11 of the Sequence Listing and combinations thereof. For example, the P1 can comprise a sequence in Table 5. For example, the P3 can comprise a sequence in Table 5.

One or more of the L2 and L3 can comprise a base pair mutation. For example, the L2 can comprise a sequence in Table 6. For example, the L3 can comprise a sequence in Table 6.

One or more of the J1/2, J2/3, and J3/1 can comprise a base pair mutation. For example, the J1/2 can comprise a sequence in Table 7.

The one or more mutated aptamer domain can form one or more structural conformations, such as a P2 helix conformation; a P2-P3 helix conformation; a L2-L3 unkissed conformation; a L2-L3 kissed conformation; and a guanine-bound conformation.

Provided herein is a microchip comprising the biological sensors described herein. The microchip can comprise eukaryotic cells acting as biological sensors. The microchip can comprise prokaryotic cells acting as biological sensors.

Biological Sensor (Slower Rate of Switching)

Provided herein is a biological sensor comprising: a biological molecule not found in nature comprising one or more mutated aptamer domain, wherein the one or more mutated aptamer domain comprises: one or more hairpin; one or more loop; and one or more junction. The biological sensor also comprises one or more ligand capable of binding to the one or more mutated aptamer domain, wherein the one or more ligand binds the one or more mutated aptamer domain switching the one or more mutated aptamer domain between one or more structural conformations. A rate in which the one or more mutant aptamer domain switches between the one or more structural conformations is slower than a rate in which one or more wild-type aptamer domain switches between the one or more structural conformations.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more mutated aptamer domain. The one or more mutated aptamer domain can be one or more mutated purine aptamer domain. The one or more mutated purine aptamer domain can be one or more mutated guanine aptamer domain or one or more mutated adenine aptamer domain.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The one or more mutated aptamer domain can comprise: one or more hairpin; one or more loop; and one or more junction. The one or more hairpin can be P1, P2, or P3. The one or more loop can be L2 or L3. The one or more junction can be J1/2, J2/3, and J3/1. The one or more hairpin, one or more loop, and one or more junction can be modified in length, size, sequence, chemical functional groups, or combinations thereof.

One or more of the P1, P2, and P3 can comprise a base pair mutation. For example, the P1 can comprise a sequence selected from the group consisting of: SEQ ID NOs: 10-11 of the Sequence Listing and combinations thereof. For example, the P1 can comprise a sequence in Table 5. For example, the P3 can comprise a sequence in Table 5.

One or more of the L2 and L3 can comprise a base pair mutation. For example, the L2 can comprise a sequence in Table 6. For example, the L3 can comprise a sequence in Table 6.

One or more of the J1/2, J2/3, or J3/1 can comprise a base pair mutation. For example, the J1/2 can comprise a sequence in Table 7.

The one or more mutated aptamer domain can form one or more structural conformations, such as a P2 helix conformation; a P2-P3 helix conformation; a L2-L3 unkissed conformation; a L2-L3 kissed conformation; and a guanine-bound conformation.

Provided herein is a microchip comprising the biological sensors described herein. The microchip can comprise eukaryotic cells acting as biological sensors. The microchip can comprise prokaryotic cells acting as biological sensors.

Biological Sensor

Provided herein is a biological sensor comprising: a biological molecule not found in nature comprising one or more aptamer domain, wherein the one or more aptamer domain comprises: one or more hairpin; one or more loop; and one or more junction.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more aptamer domain. The one or more aptamer domain can be one or more purine aptamer domain. The one or more purine aptamer domain can be one or more guanine aptamer domain or one or more adenine aptamer domain.

The one or more aptamer domain can comprise: one or more hairpin; one or more loop; and one or more junction. The one or more hairpin can be P1, P2, or P3. The one or more loop can be L2 or L3. The one or more junction can be J1/2, J2/3, and J3/1. The one or more hairpin, one or more loop, and one or more junction can be modified in length, size, sequence, chemical functional groups, or combinations thereof.

The one or more aptamer domain can form one or more structural conformations, such as a P2 helix conformation, a P2-P3 helix conformation, a L2-L3 unkissed conformation, a L2-L3 kissed conformation, and a guanine-bound conformation. The one or more structural conformations can be formed when a ligand capable of binding to the one or more aptamer domain binds the one or more aptamer domain switching the one or more aptamer domain between one or more structural conformations.

Provided herein is a microchip comprising the biological sensors described herein. The microchip can comprise eukaryotic cells acting as biological sensors. The microchip can comprise prokaryotic cells acting as biological sensors.

Biological Sensor

Provided herein is a biological sensor comprising: a biological molecule not found in nature comprising one or more mutated aptamer domain, wherein the one or more mutated aptamer domain comprise: one or more hairpin; one or more loop; and one or more junction.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more mutated aptamer domain. The one or more mutated aptamer domain can be one or more mutated purine aptamer domain. The one or more mutated purine aptamer domain can be one or more mutated guanine aptamer domain or one or more mutated adenine aptamer domain.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The one or more mutated aptamer domain can comprise: one or more hairpin; one or more loop; and one or more junction. The one or more hairpin can be P1, P2, or P3. The one or more loop can be L2 or L3. The one or more junction can be J1/2, J2/3, and J3/1. The one or more hairpin, one or more loop, and one or more junction can be modified in length, size, sequence, chemical functional groups, or combinations thereof.

One or more of the P1, P2, and P3 can comprise a base pair mutation. For example, the P1 can comprise a sequence selected from the group consisting of: SEQ ID NOs: 10-11 of the Sequence Listing and combinations thereof. For example, the P1 can comprise a sequence in Table 5. For example, the P3 can comprise a sequence in Table 5.

One or more of the L2 and L3 can comprise a base pair mutation. For example, the L2 can comprise a sequence in Table 6. For example, the L3 can comprise a sequence in Table 6.

One or more of the J1/2, J2/3, and J3/1 can comprise a base pair mutation. For example, the J1/2 can comprise a sequence in Table 7.

The one or more mutated aptamer domain can form one or more structural conformations, such as a P2 helix conformation, a P2-P3 helix conformation, a L2-L3 unkissed conformation, a L2-L3 kissed conformation, and a guanine-bound conformation. The one or more structural conformations can be formed when a ligand capable of binding to the one or more mutated aptamer domain binds the one or more mutated aptamer domain switching the one or more mutated aptamer domain between one or more structural conformations.

Provided herein is a microchip comprising the biological sensors described herein. The microchip can comprise eukaryotic cells acting as biological sensors. The microchip can comprise prokaryotic cells acting as biological sensors.

Biological Sensor

Provided herein is a biological sensor comprising a biological molecule not found in nature, wherein the the biological molecule comprises one or more mutated riboswitch.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The one or more mutated riboswitch can be one or more mutated purine riboswitch. The one or more mutated purine riboswitch can be one or more mutated guanine riboswitch or one or more mutated adenine riboswitch.

The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

Provided herein is a microchip comprising the biological sensors described herein. The microchip can comprise eukaryotic cells acting as biological sensors. The microchip can comprise prokaryotic cells acting as biological sensors.

A Method of Making a Biological Sensor

Provided herein is a method of making a biological sensor for one or more metabolite. The method comprises: introducing a biological molecule not found in nature into a cell, the biomolecule comprising one or more riboswitch, wherein the one or more riboswitch comprises one or more aptamer domain.

Provided herein is a method of making a biological sensor for one or more metabolite. The method comprises: introducing a biological molecule not found in nature into a cell, the biomolecule comprising one or more riboswitch, wherein the one or more riboswitch comprises one or more mutated aptamer domain.

Provided herein is a method of making a biological sensor for one or more metabolite. The method comprises: introducing a biological molecule not found in nature into a cell, the biomolecule comprising one or more mutated riboswitch.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more aptamer domain. The one or more aptamer domain can be one or more purine aptamer domain. The one or more purine aptamer domain can be one or more guanine aptamer domain or one or more aptamer domain.

The one or more aptamer domain can form one or more structural conformations, such as a P2 helix conformation, a P2-P3 helix conformation, a L2-L3 unkissed conformation, a L2-L3 kissed conformation, and a guanine-bound conformation.

The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

The biological molecule can comprise one or more mutated aptamer domain. The one or more mutated aptamer domain can be one or more mutated purine aptamer domain. The one or more mutated purine aptamer domain can be one or more mutated guanine aptamer domain or one or more mutated adenine aptamer domain.

The one or more mutated aptamer domain can form one or more structural conformations, such as a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The one or more metabolite can be nucleotides and nucleobases, amino acids, vitamins, ions, cofactors, or combinations thereof.

The cells can be eukaryotic cells or prokaryotic cells.

One or more biological molecule can be introduced into cells by viral or non-viral delivery mechanisms known in the art, such as natural uptake, electroporation, mechanical force, cell deformation (SQZ Biotech), and cell penetrating peptides. The one or more biological molecules can also be introduced into cells by any mechanism known to one of skill in the art.

Electroporation is a delivery technique in which an electrical field is applied to one or more cells in order to increase the permeability of the cell membrane, which allows substances such as drugs, nucleic acids (DNA and RNA), or biomolecules disclosed herein, to be introduced into the cell. In general, electroporation works by passing thousands of volts across a distance of one to two millimeters of suspended cells in an electroporation cuvette (1.0-1.5 kV, 250-750V/cm).

Biomolecules can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011).

Biomolecules can be delivered to a cell by a lipid nanoparticle (LNP). A LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs can also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP—cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

Biological Molecule

Provided herein is a biological molecule not found in nature. The biological molecule can comprise one or more mutated aptamer domain, wherein the one or more mutated aptamer domain comprise: one or more hairpin; one or more loop; and one or more junction.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The one or more mutated aptamer domain can form one or more structural conformations, such as a P2 helix conformation, a P2-P3 helix conformation, a L2-L3 unkissed conformation, a L2-L3 kissed conformation, and a guanine-bound conformation.

The rate in which the one or more mutant aptamer domain switches between the one or more structural conformations is slower than the rate in which one or more wild-type aptamer domain switches between the one or more structural conformations.

The rate in which the one or more mutant aptamer domain switches between the one or more structural conformations is faster than the rate in which one or more wild-type aptamer domain switches between the one or more structural conformations.

The one or more mutated aptamer domain comprises a sequence selected from the group consisting of: SEQ ID NOs: 2-9 of the Sequence Listing and combinations thereof. The one or more mutated aptamer domain comprises a sequence that is at least 95% identical to SEQ ID NOs: 2-9. The one or more mutated aptamer domain comprises a sequence that is at least 90% identical to SEQ ID NOs: 2-9. The one or more mutated aptamer domain comprises a sequence that is at least 85% identical to SEQ ID NOs: 2-9.

Biological Molecule

Provided herein is a biological molecule not found in nature comprising one or more mutated riboswitch.

The one or more mutated riboswitch can comprise SEQ ID NO: 13 of the Sequence Listing. The one or more mutated riboswitch can comprise a sequence that is at least 95% identical to SEQ ID NO: 13. The one or more mutated riboswitch can comprise a sequence that is at least 90% identical to SEQ ID NO: 13. The one or more mutated riboswitch can comprise a sequence that is at least 85% identical to SEQ ID NO: 13.

A Method of Controlling Gene Expression

Provided herein is a method of controlling gene expression. The method comprises: providing a biological molecule comprising one or more aptamer domain; exposing the biological molecule comprising one or more aptamer domain to a first ligand capable of binding to the one or more aptamer domain, wherein the first ligand binds the biological molecule comprising one or more aptamer domain switching the one or more aptamer domain to a first set of one or more structural conformations; and exposing the biological molecule comprising one or more aptamer domain to a second ligand capable of binding to the one or more aptamer domain, wherein the second ligand binds the biological molecule comprising one or more aptamer domain switching the one or more aptamer domain to a second set of one or more structural conformations, thereby terminating gene expression.

Provided herein is a method of controlling gene expression. The method comprises: exposing a biological molecule comprising one or more aptamer domain to a first ligand capable of binding to the one or more aptamer domain, wherein the first ligand binds the biological molecule comprising one or more aptamer domain switching the one or more aptamer domain to a first set of one or more structural conformations; and exposing the biological molecule comprising one or more aptamer domain to a second ligand capable of binding to the one or more aptamer domain, wherein the second ligand binds the biological molecule comprising one or more aptamer domain switching the one or more aptamer domain to a second set of one or more structural conformations, thereby terminating gene expression.

Provided herein is a method of controlling gene expression. The method comprises: providing a biological molecule comprising one or more aptamer domain; exposing the biological molecule comprising one or more aptamer domain to a first ligand capable of binding to the one or more aptamer domain, wherein the first ligand binds the biological molecule comprising one or more aptamer domain switching the one or more aptamer domain to a first set of one or more structural conformations; and exposing the biological molecule comprising one or more aptamer domain to a second ligand capable of binding to the one or more aptamer domain, wherein the second ligand binds the biological molecule comprising one or more aptamer domain switching the one or more aptamer domain to a second set of one or more structural conformations, thereby permitting gene expression.

Provided herein is a method of controlling gene expression. The method comprises: exposing a biological molecule comprising one or more aptamer domain to a first ligand capable of binding to the one or more aptamer domain, wherein the first ligand binds the biological molecule comprising one or more aptamer domain switching the one or more aptamer domain to a first set of one or more structural conformations; and exposing the biological molecule comprising one or more aptamer domain to a second ligand capable of binding to the one or more aptamer domain, wherein the second ligand binds the biological molecule comprising one or more aptamer domain switching the one or more aptamer domain to a second set of one or more structural conformations, thereby permitting gene expression.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more aptamer domain. The one or more aptamer domain can be one or more purine aptamer domain. The one or more purine aptamer domain can be one or more guanine aptamer domain or one or more adenine aptamer domain.

The one or more aptamer domain can comprise one or more hairpin, one or more loop, and one or more junction. The one or more hairpin can be P1, P2, and P3. The one or more loop can be L2 and L3. The one or more junction can be J1/2, J2/3, and J3/1.

The one or more aptamer domain can form one or more structural conformations such as a P2 helix conformation, a P2-P3 helix conformation, a L2-L3 unkissed conformation, a L2-L3 kissed conformation, and a guanine-bound conformation.

The first set of one or more structural conformations can be a P2 helix conformation, a P2-P3 helix conformation, or combinations thereof.

The second set of one or more structural conformations can be a L2-L3 unkissed conformation, a L2-L3 kissed conformation, a guanine-bound conformation, or combinations thereof.

The first ligand can be any monovalent or divalent ion. The first ligand can be magnesium (Mg2+).

The second ligand can be guanine, adenine, or any derivatives thereof.

A Method of Controlling Gene Expression

Provided herein is a method of controlling gene expression. The method comprises: providing a biological molecule comprising one or more mutated aptamer domain; exposing the biological molecule comprising one or more mutated aptamer domain to a first ligand capable of binding to the one or more mutated aptamer domain, wherein the first ligand binds the biological molecule comprising one or more mutated aptamer domain switching the one or more mutated aptamer domain to a first set of one or more structural conformations; and exposing the biological molecule comprising one or more mutated aptamer domain to a second ligand capable of binding to the one or more mutated aptamer domain, wherein the second ligand binds the biological molecule comprising one or more mutated aptamer domain switching the one or more mutated aptamer domain to a second set of one or more structural conformations, thereby terminating gene expression.

Provided herein is a method of controlling gene expression. The method comprises: exposing a biological molecule comprising one or more mutated aptamer domain to a first ligand capable of binding to the one or more mutated aptamer domain, wherein the first ligand binds the biological molecule comprising one or more mutated aptamer domain switching the one or more mutated aptamer domain to a first set of one or more structural conformations; and exposing the biological molecule comprising one or more mutated aptamer domain to a second ligand capable of binding to the one or more mutated aptamer domain, wherein the second ligand binds the biological molecule comprising one or more mutated aptamer domain switching the one or more mutated aptamer domain to a second set of one or more structural conformations, thereby terminating gene expression.

Provided herein is a method of controlling gene expression. The method comprises: providing a biological molecule comprising one or more mutated aptamer domain; exposing the biological molecule comprising one or more mutated aptamer domain to a first ligand capable of binding to the one or more mutated aptamer domain, wherein the first ligand binds the biological molecule comprising one or more mutated aptamer domain switching the one or more mutated aptamer domain to a first set of one or more structural conformations; and exposing the biological molecule comprising one or more mutated aptamer domain to a second ligand capable of binding to the one or more mutated aptamer domain, wherein the second ligand binds the biological molecule comprising one or more mutated aptamer domain switching the one or more mutated aptamer domain to a second set of one or more structural conformations, thereby permitting gene expression.

Provided herein is a method of controlling gene expression. The method comprises: exposing a biological molecule comprising one or more mutated aptamer domain to a first ligand capable of binding to the one or more mutated aptamer domain, wherein the first ligand binds the biological molecule comprising one or more mutated aptamer domain switching the one or more mutated aptamer domain to a first set of one or more structural conformations; and exposing the biological molecule comprising one or more mutated aptamer domain to a second ligand capable of binding to the one or more mutated aptamer domain, wherein the second ligand binds the biological molecule comprising one or more mutated aptamer domain switching the one or more mutated aptamer domain to a second set of one or more structural conformations, thereby permitting gene expression.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The biological molecule can comprise one or more mutated aptamer domain. The one or more mutated aptamer domain can be one or more mutated purine aptamer domain. The one or more mutated purine aptamer domain can be one or more mutated guanine aptamer domain or one or more adenine aptamer domain.

The one or more mutated aptamer domain can comprise one or more hairpin, one or more loop, and one or more junction.

The one or more hairpin can be P1, P2, and P3. One or more of the P1, P2, and P3 can comprise a base pair mutation. The P1 can comprise a sequence selected from the group consisting of: SEQ ID NOs: 10-11 of the Sequence Listing and combinations thereof. For example, the P1 can comprise a sequence in Table 5. For example, the P3 can comprise a sequence in Table 5.

The one or more loop can be L2 and L3. One or more of the L2 and L3 can comprise a base pair mutation. For example, the L2 can comprise a sequence in Table 6. For example, the L3 can comprise a sequence in Table 6.

The one or more junction can be J1/2, J2/3, and J3/1. One or more of the J1/2, J2/3, and J3/1 can comprise a base pair mutation. For example, the J1/2 can comprise a sequence in Table 7.

The one or more mutated aptamer domain can form one or more structural conformations, such as a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

The first set of one or more structural conformations can be a P2 helix conformation, a P2-P3 helix conformation, or combinations thereof.

The second set of one or more structural conformations can be a L2-L3 unkissed conformation, a L2-L3 kissed conformation, a guanine-bound conformation, or combinations thereof.

The first ligand can be any monovalent or divalent ion. The first ligand can be magnesium (Mg2+).

The second ligand can be guanine, adenine, or any derivatives thereof.

The one or more mutant aptamer domain can switch between the second set of one or more structural conformations at a slower rate than wild type aptamer domain switches between a second set of one or more structural conformations.

The one or more mutant aptamer domain can switch between the second set of one or more structural conformations at a faster rate than wild type aptamer domain switches between a second set of one or more structural conformations.

Method of Evaluating Structural Conformational Switching Changes

Provided herein is a method of evaluating structural conformational switching changes of a biological molecule comprising one or more riboswitch in response to one or more metabolite, wherein the one or more metabolite acts as a ligand to induce structural conformational switching. The method comprises: obtaining a biological molecule wherein the biological molecule comprises one or more riboswitch wherein the one or more riboswitch comprises one or more aptamer domain; subjecting the biological molecule comprising one or more riboswitch to optical tweezers for identification of a rate of switching and a barrier in a structural conformational switching rearrangement; adding one or more metabolite to the biological molecule comprising one or more riboswitch; and evaluating the rate of switching and the structural conformational switching changes of the biological molecule comprising one or more riboswitch in response to the one or more metabolite.

Provided herein is a method of evaluating structural conformational switching changes of a biological molecule comprising one or more riboswitch in response to one or more metabolite, wherein the one or more metabolite acts as a ligand to induce structural conformational switching. The method comprises: subjecting the biological molecule comprising one or more riboswitch wherein the one or more riboswitch comprises one or more aptamer domain to optical tweezers for identification of a rate of switching and a barrier in a structural conformational switching rearrangement; adding one or more metabolite to the biological molecule comprising one or more riboswitch; and evaluating the rate of switching and the structural conformational switching changes of the biological molecule comprising one or more riboswitch in response to the one or more metabolite.

The terms "switching", "conformational switching", "structural conformational switching", and "structural rearrangements" can be used interchangeably and refer to a switching between two or more closely related riboswitch conformations in 3-dimensional space under different conditions. The conditions can include a ligand or not include a ligand.

The term "structural conformation" refers to one or more closely related riboswitch conformations in 3-dimensional space under different conditions. The conditions can include a ligand or not include a ligand.

The terms "conformational transition state" and "transition state" can be used interchangeably and refer to any intermediate state that is transient in time.

The terms "rate of switching" and "rate of conformational switching" refer to a frequency of conversion from one state to another state.

The term "barrier in a structural conformational switching rearrangement" refers to one or more conditions that impede upon the structural rearrangements from one state to another state.

The term "optical tweezers" refers to a sophisticated device that can optically trap and micromanipulate small objects by employing the laser light forces. By stable trapping of small microsphere objects in three-dimension, the light force modifies the dynamics of the microscopic particles.

Provided herein is a method of evaluating structural conformational switching changes of a biological molecule comprising one or more riboswitch in response to one or more metabolite, wherein the one or more metabolite acts as a ligand to induce structural conformational switching. The method comprises: obtaining a biological molecule wherein the biological molecule comprises one or more riboswitch wherein the one or more riboswitch comprises one or more aptamer domain; subjecting the biological molecule comprising one or more riboswitch to acoustic tweezers for identification of a rate of switching and a barrier in a structural conformational switching rearrangement; adding one or more metabolite to the biological molecule comprising one or more riboswitch; and evaluating the rate of switching and the structural conformational switching changes of the biological molecule comprising one or more riboswitch in response to the one or more metabolite.

Provided herein is a method of evaluating structural conformational switching changes of a biological molecule comprising one or more riboswitch in response to one or more metabolite, wherein the one or more metabolite acts as a ligand to induce structural conformational switching. The method comprises: subjecting the biological molecule comprising one or more riboswitch wherein the one or more riboswitch comprises one or more aptamer domain to acoustic tweezers for identification of a rate of switching and a barrier in a structural conformational switching rearrangement; adding one or more metabolite to the biological molecule comprising one or more riboswitch; and evaluating the rate of switching and the structural conformational switching changes of the biological molecule comprising one or more riboswitch in response to the one or more metabolite.

The term "acoustic tweezers" refers to the use of highly focused acoustic beams to trap particles toward the beam focus. A steep intensity gradient of the acoustic microbeam is focused to create a net acoustic radiation force (gradient force). A small microparticle can be held at the focal plane, provided a minimal difference in acoustic impendence between the microparticles and the surrounding medium exists. Single beam acoustic tweezers (SBAT) have been demonstrated to trap microparticles under steady flow. SBAT could generate trapping forces at the nanoNewton level, unlike Optical tweezers that can measure forces accurately to sub-picoNewtons. Several uses of acoustic tweezers have been demonstrated to be capable of manipulating a single cell, a bacterium, estimation of the deformability of red blood cells, or breast cancer cells. However, none of the SBAT or acoustic tweezer technology have been used to manipulate subcellular biomolecules, as have been demonstrated with Optical Tweezers.

The biological molecule can comprise deoxyribonucleic acid (DNA). The biological molecule can comprise ribonucleic acid (RNA). The biological molecule can be deoxyribonucleic acid (DNA). The biological molecule can be ribonucleic acid (RNA). The RNA can be human RNA, microbial RNA, parasitic RNA, bacterial RNA, viral RNA, fungal RNA, plant RNA, and combinations thereof. The biological molecule can comprise a protein. The biological molecule can comprise a carbohydrate.

The one or more metabolite can be nucleotides and nucleobases, amino acids, vitamins, ions, cofactors, or combinations thereof.

The method can further comprise the step of constructing a switch, utilizing data obtained during the evaluating step.

The method can further comprise creating a modified biological molecule that has an RNA sequence that has been mutated relative to the RNA sequence of the wild-type biological molecule. The mutated RNA sequence can be a mutated RNA sequence comprising one or more mutated riboswitches. The mutated RNA can be an RNA sequence comprising one or more mutated apatmer domains. The structural conformational switching of the modified biological molecule can be faster than the structural conformational switching of the wild-type biological molecule. The structural conformational switching of the modified biological molecule can be slower than the structural conformational switching of the wild-type biological molecule.

The method can further comprise the step of constructing a switch, utilizing data from the modified biological molecule obtained during the evaluating step.

The structural conformational switching of the RNA sequence comprising one or more mutated riboswitches can be faster than the structural conformational switching of the wild-type RNA sequence. The structural conformational switching of the RNA sequence comprising one or more mutated riboswitches can be slower than the structural conformational switching of the wild-type RNA sequence.

The structural conformational switching of the RNA sequence comprising one or more riboswitches comprising one or more mutated aptamer domains can be faster than the structural conformational switching of the wild-type RNA sequence.

The structural conformational switching of the RNA sequence comprising one or more riboswitches comprising one or more mutated aptamer domains can be slower than the structural conformational switching of the wild-type RNA sequence.

The method can further comprise a step of constructing a modified biological molecule comprising one or more riboswitch with requisite switch, utilizing data obtained during the evaluating step.

The one or more aptamer domain can form one or more structural conformations, such as a P2 helix conformation, a P2-P3 helix conformation, a L2-L3 unkissed conformation, a L2-L3 kissed conformation, and a guanine-bound conformation.

The one or more mutated aptamer domain can form one or more structural conformations, such as a P2 helix conformation, a P2-P3 helix conformation, a L2-L3 unkissed conformation, a L2-L3 kissed conformation, and a guanine-bound conformation.

The one or more mutated aptamer domain can comprise a sequence selected from the group consisting of: SEQ ID NOs: 2-9 of the Sequence Listing and combinations thereof. The one or more mutated aptamer domain can comprise a sequence that is at least 95% identical to SEQ ID NOs: 2-9. The one or more mutated aptamer domain can comprise a sequence that is at least 90% identical to SEQ ID NOs: 2-9. The one or more mutated aptamer domain can comprise a sequence that is at least 85% identical to SEQ ID NOs: 2-9.

A Method of Identifying One or More Transition State of a Biological Molecule

Provided herein is a method of identifying one or more transition state of a biological molecule, the method comprising: obtaining the biological molecule wherein the biological molecule comprises one or more riboswitch wherein the one or more riboswitch comprises one or more aptamer domain; subjecting the biological molecule comprising one or more riboswitch to optical tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: subjecting the biological molecule comprising one or more riboswitch, wherein the one or more riboswitch comprises one or more aptamer domain, to optical tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more riboswitch wherein the one or more riboswitch comprises one or more mutated aptamer domain; subjecting the biological molecule comprising one or more riboswitch to optical tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: subjecting the biological molecule comprising one or more riboswitch, wherein the one or more riboswitch comprises one or more mutated aptamer domain, to optical tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more mutated riboswitch; subjecting the biological molecule comprising one or more mutated riboswitch to optical tweezers to identify one or more transition states of the biological molecule and a rate of conformational switching between the one or more transition state of the biological molecule; adding one or more metabolite to the biological molecule comprising one or more mutated riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: subjecting the biological molecule comprising one or more mutated riboswitch to optical tweezers to identify one or more transition states of the biological molecule and a rate of conformational switching between the one or more transition state of the biological molecule; adding one or more metabolite to the biological molecule comprising one or more mutated riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more riboswitch wherein the one or more riboswitch comprises one or more aptamer domain; subjecting the biological molecule comprising one or more riboswitch to acoustic tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: subjecting the biological molecule comprising one or more riboswitch, wherein the one or more riboswitch comprises one or more aptamer domain, to acoustic tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more riboswitch wherein the one or more riboswitch comprises one or more mutated aptamer domain; subjecting the biological molecule comprising one or more riboswitch to acoustic tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: subjecting the biological molecule comprising one or more riboswitch, wherein the one or more riboswitch comprises one or more mutated aptamer domain, to acoustic tweezers to identify one or more transition states of the biological molecule and a rate of conformational switching between the one or more transition state of the biological molecule; adding one or more metabolite to the biological molecule comprising one or more riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: obtaining the biological molecule wherein the biological molecule comprises one or more mutated riboswitch; subjecting the biological molecule comprising one or more mutated riboswitch to acoustic tweezers to identify one or more transition states of the biological molecule and a rate of conformational switching between the one or more transition state of the biological molecule; adding one or more metabolite to the biological molecule comprising one or more mutated riboswitch; and evaluating the structure of the one or more transition state of the biological molecule and the rate of conformational switching between the one or more transition state in response to the one or more metabolite.

Provided herein is a method of identifying one or more transition state of a biological molecule, the method comprising: subjecting the biological molecule comprising one or more mutated riboswitch to acoustic tweezers to identify one or more transition states of the biological molecule and a rate of conformational switching between the one or more transition state of the biological molecule; adding one or more metabolite to the biological molecule comprising one or more mutated riboswitch; and evaluating the structure of the one or more transition state of the biological molecule and the rate of conformational switching between the one or more transition state in response to the one or more metabolite.

Sequences that are Identical

Computer implementations of mathematical algorithms can be utilized for comparison of sequences to determine sequences that are identical. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, word length=12, to obtain nucleotide sequences homologous to a nucleotide sequence encoding a protein of the invention. BLAST protein searches can be performed with the BLASTX program, score=50, word length=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, and PSI-BLAST, the default parameters of the respective programs (e.g., BLASTN for nucleotide sequences, BLASTX for proteins) can be used. (See the National Center for Biotechnology Information website on the world-wide web at ncbi.nlm.nih.gov.). Alignment may also be performed manually by inspection.

The terms "sequence identical", "sequence identity", and "sequences that are identical" are used interchangeably and are used to describe the sequence relationship between two or more polynucleotides. More specifically, the terms are used to describe the sequence relationship between two riboswitch sequences. Even more specifically, the terms are used to describe the sequence relationship between two aptamer domain sequences.

A polynucleotide sequence that is identical to another polynucleotide sequence is 100% identical. A polynucleotide sequence can be 100% identical to another polynucleotide sequence. A polynucleotide sequence can comprise a sequence that is at least 100% identical to another sequence. A polynucleotide sequence can comprise a sequence that is at least 95% identical to another sequence. A polynucleotide sequence can comprise a sequence that is at least 90% identical to another sequence. A polynucleotide sequence can comprise a sequence that is at least 85% identical to another sequence.

A riboswitch sequence that is identical to another riboswitch sequence is 100% identical. A riboswitch sequence can be 100% identical to another riboswitch sequence. A riboswitch sequence can comprise a sequence that is at least 100% identical to another sequence. A riboswitch sequence can comprise a sequence that is at least 95% identical to another sequence. A riboswitch sequence can comprise a sequence that is at least 90% identical to another sequence. A riboswitch sequence can comprise a sequence that is at least 85% identical to another sequence.

An aptamer domain sequence that is identical to another aptamer domain sequence is 100% identical. An aptamer domain sequence can be 100% identical to another aptamer domain sequence. An aptamer domain sequence can comprise a sequence that is at least 100% identical to another sequence. An aptamer domain sequence can comprise a sequence that is at least 95% identical to another sequence. An aptamer domain sequence can comprise a sequence that is at least 90% identical to another sequence. An aptamer domain sequence can comprise a sequence that is at least 85% identical to another sequence.

Incorporation by Reference

U.S. Patent Application Publication Nos. 2009/0117545 and 2013/0029342 are incorporated by reference herein. In addition, any other patent, publication, or other disclosure material identified herein in the specification are incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

Definitions

The term "comprising" or "comprises" is used in reference to compositions, methods, and respective component(s) thereof, that are essential to the invention, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

EXAMPLES

The invention will be more fully understood by reference to the following examples, which provide illustrative non-limiting aspects of the invention.

Example 1—RNA Synthesis for Single-Molecule and ITC Experiments

The RNA with the Handle A and Handle B for single-molecule optical-tweezers experiments were synthesized as follows. The 188-nucleotide (nt) xpt leader sequence was PCR amplified from *Bacillus subtilis* strain 1A1 (*Bacillus* Genetic Stock Center, Columbus, OH) and cloned into a pBR322 vector as an EcoRI-HindIII insert. The integrity of the construct was confirmed by sequencing (Genewiz) and used as a template to generate the 69-nt wild-type guanine-aptamer and the mutants using Quick Change site-directed mutagenesis kit (Stratagene). To synthesize the "handles", the DNA template flanking the insert (~550 nts on each side), was amplified using suitable DNA primers. Handle A contained biotin at the 5' end that was incorporated by using biotinylated oligos (Integrated DNA Tech. Inc.). Handle B was modified with digoxigenin (generated by klenow filling) at the 3' end. In a separate reaction, the DNA fragment comprising handle-insert-handle sequence was PCR amplified with the oligos containing a T7-RNA polymerase promoter (shown as underlined) sequence:

5'-TAATACGACTCACTATAGGGACTGGTGAGTACTCAACCAAGTC and

5'-TAGGAAGCAGCCCAGTAGTAGG.

RNAs were synthesized by in vitro transcription using Ribomax kit (Stratagene). The RNA and the modified Handles A and B were mixed in the stoichiometric ratio of 10:1:1 in a 100 µl reaction buffer that contained Formamide (400 µl), 0.5 M EDTA (1 µl), 1M PIPES (20 µl), 5M NaCl (40 µl). Annealing of the RNA with the DNA handles were carried out at 85° C. for 10 minutes, 62° C. for 2 hrs, 52° C. for 2 hrs and then, lowering the temperature to 10° C. at a rate of 0.1° C./min. Subsequently, the annealed RNA/DNA hybrid was precipitated and reconstituted in the Tris-NaCl buffer. The reconstituted RNA-Handles hybrid molecule was attached to the streptavidin and the anti-digoxigenin antibody-coated beads (Spherotech Inc.).

Example 2—Isothermal Titration Calorimetry (ITC)

For ITC experiments, wild-type G-aptamer and the mutant RNAs were synthesized by in vitro transcription of the DNA template and purified by denaturing polyacrylamide gel electrophoresis (PAGE). The ligand guanine was introduced in the syringe, while the RNA into the sample cell at a final concentration of 10 µM and 1 µM respectively. The concentrations were determined by absorbance reading using $\varepsilon_{260}$=12010 M$^{-1}$ cm$^{-1}$ (guanine) and $\varepsilon_{260}$=711400 M$^{-1}$ cm$^{-1}$ (RNA). The buffer in the syringe and the sample cell contained 50 mM K$^+$ Hepes (pH 7.5), 100 mM KCl, and 10 mM MgCl$_2$. Binding reactions were performed at 30° C. on a MicroCal iTC200 instrument (Malvern) with a reference power of 6 µcal/sec, an initial delay of 60 secs and a stirring speed of 750 rpm. Guanine was titrated into the sample cell in 16 injections (2.5 µl each). The injection rate was 0.5 µl/sec and the spacing between the injections was maintained at 120 sec. Data was baseline corrected and fitted to a single-site binding model to obtain association constant ($K_A$), stoichiometry (n) and binding enthalpy, $\Delta H$. The dissociation constant ($K_D$) and the binding free energy, $\Delta G$ was obtained from the fitted parameters using the following relations. All data analysis was performed using the Origin ITC software.

$$K_D = \frac{1}{K_A} \quad (S1)$$

$$\Delta G = RT \ln K_D = \Delta H - T\Delta S \quad (S2)$$

The ITC results are reported as mean±standard deviation from three independent experiments.

Example 3—Guanine-Induced Transcriptional Control and β-Galactosidase Reporter Assay To assess if the aptamer mutants can exert a transcriptional control similar to the previously reported wild-type xpt-pbuX riboswitch, a xpt-lacZ fusion was constructed as described by Mandal et al., "Riboswitches control fundamental biochemical pathways in *Bacillus subtilis* and other bacteria". Cell 113, 577-586 (2003). Briefly, nts −121 to +197 relative to the transcriptional start site of the xpt-pbuX operon from *B. subtilis* 1A1 (BGSC, Columbus, Ohio) was PCR amplified and cloned upstream of the lacZ reporter gene into pDG1661 vector. After confirming the cloned sequence, plasmid variants were integrated into the amyE locus of the 1A1 strain. Transformants were selected for double markers, specifically for chloramphenicol (5 µg/ml) resistance and sensitivity to spectinomycin (100 µg/ml). Selected *B. subtilis* colonies were subsequently grown in minimal media (25 g/L K$_2$HPO$_4$·3H$_2$O, 6 g/L KH$_2$PO$_4$, 1 g/L sodium citrate, 0.2 g/l MgSO$_4$·7H$_2$O, 2 g/L Na$_2$SO$_4$, 50 µM FeCl$_3$, 2 µM MnCl$_2$, 50 µg/ml L-Tryptophan, 50 µg/ml L-Lysine, 50 µg/ml L-Methionine, 0.4 g/100 ml glucose, and 0.2 g/100 ml glutamate) at 37° C. with vigorous shaking. Purines were added at a final concentration of 0.1 mg/ml. Cells were harvested at mid-logarithmic growth phase ($A_{600}$~0.1-0.4), and resuspended in the above buffer for the reporter assay. The color development was recorded by measuring absorbance, $A_{420}$ at the end of the reaction with appropriate controls. Data is represented in Miller Units calculated from the following relation:

$$\text{Miller Units} = \frac{(1000 \times A_{420})}{\Delta t(\min.) \times \text{volume of cell suspension (ml)} \times A_{600}},$$

where $\Delta t$ is the total duration taken in the substrate cleavage by ß-galactosidase, measured as absorbance, $A_{420}$. The Miller Units shown in FIG. 4A represents mean±standard deviation from 3 independent experiments, wherein each independent experiment was performed in duplicate.

Example 4—Optical Tweezers

Figure 16C:
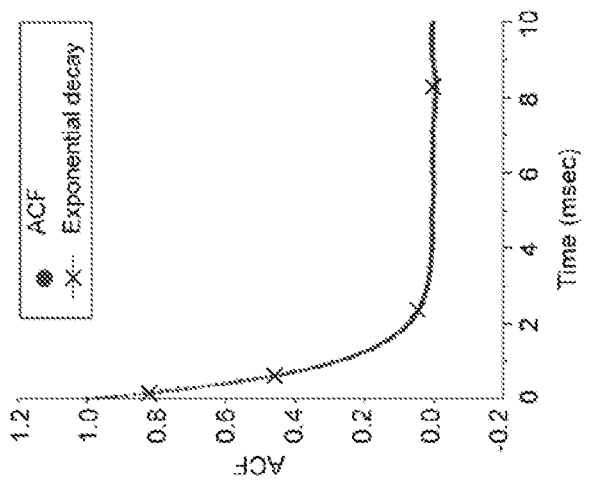
FIG. 16C is a chart showing the power spectrum recorded for a certain bead #9 with diameter 4.6 um at 40 kHz and 0.4 kHz sampling frequencies.
Figure 16B:
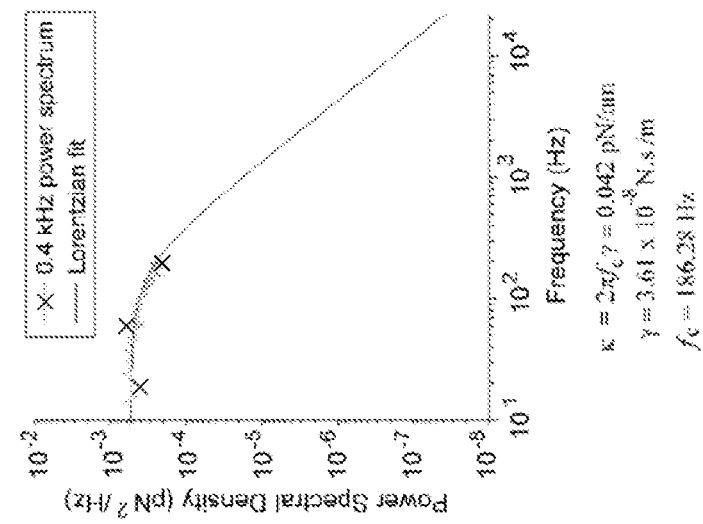
FIG. 16B is a chart showing the power spectrum recorded for a certain bead #9 with diameter 4.6 um at 40 kHz and 0.4 kHz sampling frequencies.
Figure 16A:
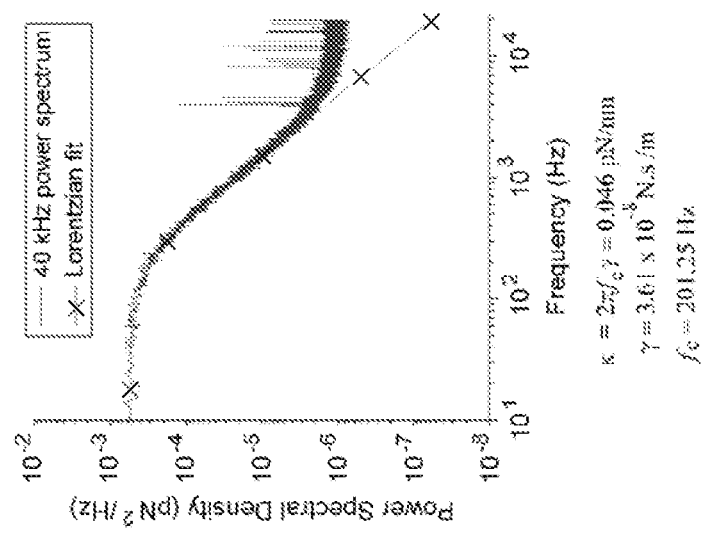
FIG. 16A is a chart showing the power spectrum recorded for a certain bead #9 with diameter 4.6 um at 40 kHz and 0.4 kHz sampling frequencies.

A miniaturized dual beam optical tweezers instrument was constructed with a sampling rate of 0.4, 4 and 40 kHz. Typically, in the tweezers set up (FIGS. 2A-E), a single-molecule of RNA is held between two beads via ~550 nucleotide (nt) long Handles A and B. Preparation of Handles and the RNA is described in the section above. The streptavidin coated polystyrene bead (diameter 1.5-1.9 µm, Spherotech Inc.) is fixed on a micropipette via suction, and the anti-digoxigenin coated bead (diameter 4.0-4.9 µm, Spherotech Inc.) is held in the dual counter-propagating laser beam. The trap stiffness, K is measured at 0.04-0.06 pN/nm from the power spectrum analysis of the Brownian motion of the trapped bead. For power spectrum analysis, a polystyrene bead with diameter ~4.6 µm is trapped in the counter-propagating laser beam in aqueous buffer with a fixed trap position. The trap stiffness was calculated from 10 independent beads at low and high data acquisition rates that exhibited a near similar value. The average from 10 beads yielded K~0.049±0.0008 pN/nm, and the stoke's drag coefficient, y=0.0364±0.0002 pN. s/µm. The calibration of force was also ascertained by pulling a dsDNA that showed an overstretch transition between 63-pN. The $f_c$ obtained from the Lorentzian fit for a certain bead #9 in 40 and 0.4 kHz sampling rate is shown in the FIGS. 16A-C. However, the autocorrelation time ($\tau_0$) defined as the $\tau_1 = 1/2\pi f_c$ as described by Zoldak et al., "Ultrafast folding kinetics and cooperativity of villin headpiece in single-molecule force spectroscopy". Proc. Natl. Acad. Sci. U.S.A 110, 18156 (2013) sets the detection limit for the observable kinetics, which is different from the sampling frequencies. The plot in Figure c shows the autocorrelated function (ACF) with respect to time. The ACF for the time series of force signal, $F_i$, with sampling rate δ and N data points, is calculated as, $$ACF\left(\tau = \frac{j}{\delta}\right) = \frac{\sum_{i=0}^{N-1}(F_i - \mu)(F_{i-j} - \mu)}{\sum_{i=0}^{N-1}(F_i - \mu)^2},$$

where μ is the mean of F signal. ACF is fitted by the single exponential decay equation, $$ACF(\tau) = \exp\left(-\frac{\tau}{\tau_0}\right),$$

where $\tau_0$ the fitted parameter, shown in red. Thus, by analyzing the autocorrelation time for the same 10 independent beads, the average $\tau_0$ is 0.77±0.005 msec (mean±std. error). This means that it is possible to measure accurately the RNA folding and unfolding kinetics as fast as 0.77 msec in our counter-propagating dual beam trapping system, although a higher sampling frequency such as 40 kHz will set the temporal resolution at 25 μsec for constant-force assay.

Thus, in the folding kinetics of the guanine riboswitch, the rates for the two hairpins P2 and P3 are fast, ranging from 8.5-32.3 s$^{-1}$ as shown in Table 1. This indicates that the lifetimes (τ) of the rapidly interconverting states range from 0.12-0.031 sec, which is 155-40 fold higher than the average $\tau_0$~0.77 msec. For the slow interconverting states such as the L2-L3, P1 and the junctions, the lifetimes range from 2.5-1 sec, which is ~1300 times higher than the cut-off limit. Therefore, from all analyses, it can be confirmed that the sampling frequencies of 4 and 40 kHz are well above the cut-off limits for the temporal resolution of our instrument, and hence the rates measured for the individual secondary and tertiary structural elements are reliable and accurate within the error limits.

The forces on the bead were recorded at an acquisition rate of 44 kHz. Data was collected from the stereo phone jacks on the ADC boards of the Tweezers instrument and sent to the host computer audio input for analysis by SignalScope program (Faber Acoustical, LLC). As shown in the plot, power spectral density is fitted with the Lorentzian fit to yield the corner frequency ($f_c$) that was used to calculate the trap stiffness. This setup was used to perform three different mechanical reactions: force-ramp (FR), constant-force (CF) and force-jump (FJ) under a controlled force. In the force-ramp (FR) experiment, the trap was moved at 200 nm/s, which corresponded to a loading rate 7-8 pN/s. This resulted in a tension to the ends of the RNA, measured by the change in the light momentum caused by the movement of the bead in the trap. The force-ramp data is plotted as force vs. extension curves (FEC).

In a constant-force (CF) experiment, the RNA is held at a preset force through feedback control. The preset force typically fluctuated around the mean with a standard deviation ±0.15 pN. In this mode, data is recorded from 4-40 kHz to capture the fast intermediates. The plots are shown as extension vs. time (as in FIG. 6A). In force-jump (FJ) assay, the force is suddenly jumped from one force to another, and then held constant thereafter, as shown in FIGS. 23A-B.

All FR, CF and FJ experiments were carried out at an ambient temperature, 25±0.5° C. The buffer in the microfluidics contained 10 mM Tris-HCl, pH 7.5 at 25° C., 250 mM NaCl, 3 mM MgCl$_2$, and purine concentrations as indicated in wild-type aptamer. Unless stated otherwise, Mg$^{2+}$ concentration in the buffer was maintained at 3 mM in all experiments. The buffer in mutant m1 contained 5 mm Mg$^{2+}$ and 1 μM G, and in m3 contained 5 mM Mg$^{2+}$ and 200 nM Guanine. For the remaining m2, m4, m5 and m6 mutants, the buffer in single-molecule experiments was supplemented only with 3 mM Mg$^{2+}$ and 200 nM Guanine.

Example 5—Establishing a Single-Molecule Connection

As shown in FIGS. 2A-E, a single molecule of guanine aptamer RNA was held between two beads. The larger anti-digoxigenin coated polystyrene bead (diameter ~4.6 μm) was trapped in the potential well formed by the dual counter-propagating laser beams (λ, 845 nm). The smaller streptavidin coated polystyrene bead (diameter ~1.9 μm) was fixed on a stationary micropipette by suction. Mechanical unfolding experiments were conducted only on the bead pairs that were connected by a single-molecule attachment. To establish a single-molecule connectivity between the bead pairs, the trap was moved along with the anti-dig bead to a close vicinity of the micropipette bead. The micropipette bead attaches to the free end of one RNA molecule. To assess that the connection is due to a single molecule, $$F = \frac{k_B T}{P}\left[\frac{1}{4}\left(1 - \frac{X}{L} + \frac{F}{K}\right)^{-2} - \frac{1}{4} + \frac{X}{L} - \frac{F}{K}\right]$$

was used in the graphical user interface to fit the force-extension trace. The fitted parameters agree with the previously reported values for the hybrid handles and the ssRNA. Once the fitting was established for a given tether, further force-ramp and constant-force experiments were performed. At the end of the experiment, the tethered RNA was stretched to a higher force in order to observe an overstretch transition between 63-65 pN, which is indicative of a single molecule connectivity. Multiple connections that hold the bead pair cannot be fitted with $$F = \frac{k_B T}{P}\left[\frac{1}{4}\left(1 - \frac{X}{L} + \frac{F}{K}\right)^{-2} - \frac{1}{4} + \frac{X}{L} - \frac{F}{K}\right].$$

Such connections withstand the high forces.

Example 6—Force-Ramp and Constant-Force Experiment

In the force-ramp experiment, the trap was moved away (pull cycle) from the micropipette at 200 nm/sec, which corresponded to a loading rate of 7-8 pN/sec. This movement of the trap exerted a tension at the ends of the tethered RNA aptamer. The applied tension resulted in the unfolding of the RNA, shown as the blue curve in Figure Next, as the trap was moved closer to the micropipette (relax cycle), the RNA refolded back to its initial state (red curve in FIG. 5A). In the constant-force (CF) experiment, the RNA was held at a preset force (FIG. 6A). The loading rate in CF experiments was zero. The preset force typically fluctuated around the mean with standard deviation ±0.15 pN. The force-ramp and the CF experiments were carried out at an ambient temperature 25±0.5° C. in buffer containing 10 mM Tris-HCl, pH 7.5 at 250 mM NaCl, 3 mM MgCl$_2$ unless mentioned otherwise. The Mg$^{2+}$ and the purine concentrations for the mutants were indicated in FIGS. 7A-B.

Example 7—Method of Detecting a Biological Molecule in a Patient

A biological sample is isolated from a patient suspected of having a bacterial, fungal, parasitic, protozoan, or viral infection. RNA is released from the biological sample using chemical and enzymatic methods. The RNA is added to wells of a 96-well microplate, which are previously coated with bound fluorescently labeled guanine or its chemical derivatives. The guanine aptamer domain of the RNA binds to the fluorsecently labeled guanine coated on the 96-well plate. The level of fluoresence is measured using a fluorimeter to determine the concentration of guanine aptamer domain RNA that is present in the biological sample This result is compared to the threshold.

Example 8—Method of Detecting a Biological Molecule

A water sample suspected of being contaminated with microbial growth is obtained. RNA is released from the water sample containing pathogenic or non-pathogenic microbes using chemical and enzymatic methods. The RNA is added to wells of a 96-well microplate, which are previously coated with bound fluorescently labeled guanine or its chemical derivatives. The guanine aptamer domain of the RNA binds to the fluorsecently labeled guanine coated on the 96-well plate. The level of fluoresence is measured using a fluorimeter to determine the concentration of guanine aptamer domain RNA that is present in the water sample.

Example 9—Method of Detecting a Biological Molecule in a Patient

A biological sample is isolated from a patient suspected of having a disease caused by bacterial, fungal, parasitic, protozoan, or viral infection or metabolic or other disease. The sensing metabolite, guanine or its analogs, is released from the biological sample using chemical and/or enzymatic methods. The released metabolite (i.e. guanine or its analogs) is added to a 96-well microplate, which are previously coated with fluorescently labeled guanine aptamer domain. The metabolite, guanine, binds to the fluorsecently labeled RNA comprising a guanine aptamer domain coated on the 96-well plate. The level of fluoresence is measured using a fluorimeter to determine the concentration of metabolite that is present in the biological sample, which will provide the presence of disease causing microbe or the disorder.

Example 10—Method of Detecting a Biological Molecule

A water sample suspected of being contaminated with microbial growth is obtained. Guanine is released from the water sample using chemical and enzymatic methods. The guanine is added to wells of a 96-well microplate, which are previously coated with bound fluorescently labeled RNA comprising a guanine aptamer domain. The guanine binds to the fluorsecently labeled RNA comprising a guanine aptamer domain coated on the 96-well plate. The level of fluoresence is measured using a fluorimeter to determine the concentration of guanine that is present in the water sample.

Note Regarding Illustrative Examples

While the present disclosure provides descriptions of various specific aspects for the purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

What is claimed is:

1. A biological sensor comprising:
a biological molecule not found in nature comprising one or more mutated aptamer domain, wherein the one or more mutated aptamer domain comprises: one or more hairpin; one or more loop; and one or more junction; and
one or more ligand capable of binding to the one or more mutated aptamer domain, wherein the one or more ligand binds the one or more mutated aptamer domain switching the one or more aptamer domain between one or more structural conformations;
wherein a rate in which the one or more mutant aptamer domain switches between the one or more structural conformations is faster than a rate in which one or more wild-type aptamer domain switches between the one or more structural conformations, and
wherein the one or more mutated aptamer domain comprises a sequence selected from the group consisting of: SEQ ID NOs: 2-9 of the Sequence Listing and combinations thereof.

2. A biological sensor comprising:
a biological molecule not found in nature comprising one or more mutated aptamer domain, wherein the one or more mutated aptamer domain comprises: one or more hairpin; one or more loop; and one or more junction, wherein the one or more mutated aptamer domain is switchable between one or more structural conformations in response to one or more ligand binding to the one or more mutated aptamer domain,
wherein a rate in which the one or more mutant aptamer domain switches between the one or more structural conformations is faster than a rate in which one or more wild-type aptamer domain switches between the one or more structural conformations, and
wherein the one or more mutated aptamer domain comprises a sequence selected from the group consisting of: SEQ ID NOs: 2-9 of the Sequence Listing and combinations thereof.

* * * * *